(12) United States Patent
Lopez et al.

(10) Patent No.: US 10,314,764 B2
(45) Date of Patent: Jun. 11, 2019

(54) FLUID TRANSFER DEVICES AND METHODS OF USE

(71) Applicant: ICU Medical, Inc., San Clemente, CA (US)

(72) Inventors: George A. Lopez, Laguna Beach, CA (US); Thomas F. Fangrow, Mission Viejo, CA (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

(21) Appl. No.: 15/877,190

(22) Filed: Jan. 22, 2018

(65) Prior Publication Data

US 2018/0161244 A1    Jun. 14, 2018

Related U.S. Application Data

(63) Continuation of application No. 14/310,942, filed on Jun. 20, 2014, now Pat. No. 9,883,987, which is a
(Continued)

(51) Int. Cl.
*A61J 1/20*    (2006.01)
*A61M 5/142*    (2006.01)
(Continued)

(52) U.S. Cl.
CPC ........... *A61J 1/2089* (2013.01); *A61J 1/1406* (2013.01); *A61J 1/2096* (2013.01);
(Continued)

(58) Field of Classification Search
CPC ...... A61J 1/2089; A61J 1/2096; A61J 1/1406; A61J 1/1481; A61J 1/1487; A61J 1/2062;
(Continued)

(56) References Cited

U.S. PATENT DOCUMENTS 1,923,501 A    8/1933  Perry
D222,956 S    2/1972  Sato
(Continued)

FOREIGN PATENT DOCUMENTS

DE    20 2004 014 868    11/2004
EP         0 974 330    1/2000
(Continued)

OTHER PUBLICATIONS

U.S. Appl. No. 29/571,547, filed Jul. 19, 2016, Shauver et al.
(Continued)

*Primary Examiner* — Jason K Niesz
(74) *Attorney, Agent, or Firm* — Knobbe Martens Olson & Bear, LLP

(57) ABSTRACT

Fluid transfer systems are disclosed that can be configured to transfer precise amounts of fluid from a source container to a target container. The fluid transfer system can have multiple fluid transfer stations for transferring fluids into multiple target containers or for combining different types of fluids into a single target container to form a mixture. The fluid transfer system can include a pump and a destination sensor, such as a weight sensor. The fluid transfer system can be configured to flush remaining fluid out of a connector to reduce waste, using air or a flushing fluid.

23 Claims, 45 Drawing Sheets

Related U.S. Application Data continuation of application No. PCT/US2012/071493, filed on Dec. 21, 2012.

(60) Provisional application No. 61/579,622, filed on Dec. 22, 2011.

(51) Int. Cl.
  *A61M 5/168* (2006.01)
  *A61J 1/14* (2006.01)
  *A61J 1/10* (2006.01)
  *A61J 1/16* (2006.01)

(52) U.S. Cl.
  CPC .... *A61M 5/14228* (2013.01); *A61M 5/16845* (2013.01); *A61J 1/10* (2013.01); *A61J 1/1481* (2015.05); *A61J 1/1487* (2015.05); *A61J 1/16* (2013.01); *A61J 1/201* (2015.05); *A61J 1/2037* (2015.05); *A61J 1/2051* (2015.05); *A61J 1/2055* (2015.05); *A61J 1/2058* (2015.05); *A61J 1/2062* (2015.05); *F04C 2270/0421* (2013.01)

(58) Field of Classification Search
  CPC ........ A61J 1/201; A61J 1/2051; A61J 1/2037; A61J 1/2058; A61J 1/2055; A61J 1/16; A61J 1/10; A61M 1/1406; A61M 5/16845; A61M 5/14228; F04C 2270/0421
  See application file for complete search history.

(56) References Cited

U.S. PATENT DOCUMENTS

| | | |
|---|---|---|
| D222,957 S | 2/1972 | Sato |
| D236,163 S | 7/1975 | Manno |
| 4,005,710 A | 2/1977 | Zeddies et al. |
| 4,084,606 A | 4/1978 | Mittlerman |
| 4,190,048 A | 2/1980 | Sampson |
| 4,262,671 A | 4/1981 | Kersten |
| 4,306,705 A | 12/1981 | Svensson |
| 4,336,802 A | 6/1982 | Stone et al. |
| 4,367,736 A | 1/1983 | Gupton |
| D268,206 S | 3/1983 | Kosako |
| D268,284 S | 3/1983 | Manno et al. |
| 4,410,321 A | 10/1983 | Pearson et al. |
| 4,519,792 A | 5/1985 | Dewe |
| 4,559,043 A | 12/1985 | Whitehouse et al. |
| 4,561,856 A | 12/1985 | Cochran |
| 4,666,429 A | 5/1987 | Stone |
| 4,670,007 A | 6/1987 | Wheeldon et al. |
| 4,683,916 A | 8/1987 | Raines |
| 4,755,172 A | 7/1988 | Baldwin |
| 4,768,568 A | 9/1988 | Fournier et al. |
| 4,778,450 A | 10/1988 | Kamen |
| 4,819,684 A | 4/1989 | Zaugg et al. |
| 4,863,429 A | 9/1989 | Baldwin |
| D305,165 S | 12/1989 | Rudolph et al. |
| 4,922,975 A | 5/1990 | Polaschegg |
| 4,969,874 A | 11/1990 | Michel et al. |
| 4,976,590 A | 12/1990 | Baldwin |
| 4,995,268 A | 2/1991 | Ash et al. |
| 5,024,347 A | 6/1991 | Baldwin |
| 5,037,390 A | 8/1991 | Raines et al. |
| 5,114,580 A | 5/1992 | Ahmad et al. |
| D328,952 S | 8/1992 | Arioka |
| 5,176,658 A | 1/1993 | Ranford |
| 5,224,937 A | 7/1993 | van der Heiden et al. |
| 5,256,155 A | 10/1993 | Yerlikaya et al. |
| 5,300,044 A | 4/1994 | Classey et al. |
| D348,101 S | 6/1994 | Poli et al. |
| 5,334,211 A | 8/1994 | Shiber |
| 5,336,201 A | 8/1994 | von der Decken |
| D352,778 S | 11/1994 | Irvin |
| 5,378,231 A | 1/1995 | Johnson et al. |
| 5,405,333 A | 4/1995 | Richmond |
| 5,423,791 A | 6/1995 | Bartlett |
| 5,431,201 A | 6/1995 | Torchia et al. |
| 5,439,451 A | 8/1995 | Collinson et al. |
| 5,609,572 A | 3/1997 | Lang |
| 5,645,538 A | 7/1997 | Richmond |
| 5,676,346 A | 10/1997 | Leinsing |
| 5,685,866 A | 11/1997 | Lopez |
| 5,776,345 A | 7/1998 | Truitt et al. |
| 5,782,816 A | 7/1998 | Werschmidt et al. |
| 5,807,312 A | 9/1998 | Dzwonkiewicz |
| 5,871,500 A | 2/1999 | Jepson et al. |
| D408,079 S | 4/1999 | Ellis |
| 5,897,526 A | 4/1999 | Vaillancourt |
| 5,904,666 A | 5/1999 | DeDecker et al. |
| 5,935,106 A | 8/1999 | Olsen |
| 5,947,951 A | 9/1999 | Ortiz et al. |
| 5,968,014 A | 10/1999 | Neftel et al. |
| 5,989,237 A | 11/1999 | Fowles et al. |
| 6,059,747 A | 5/2000 | Bruggeman et al. |
| 6,110,153 A | 8/2000 | Davis et al. |
| RE36,871 E | 9/2000 | Epstein et al. |
| 6,123,685 A | 9/2000 | Reynolds |
| 6,132,404 A | 10/2000 | Lopez |
| 6,152,900 A | 11/2000 | Mayer |
| 6,179,823 B1 | 1/2001 | Niedospial, Jr. |
| 6,202,708 B1 | 3/2001 | Bynum |
| 6,221,041 B1 | 4/2001 | Russo |
| 6,245,048 B1 | 6/2001 | Fangrow, Jr. et al. |
| 6,287,289 B1 | 9/2001 | Niedospial, Jr. |
| 6,302,864 B1 | 10/2001 | Nowosielski |
| 6,425,497 B1 | 7/2002 | Chu et al. |
| 6,474,375 B2 | 11/2002 | Spero et al. |
| 6,485,472 B1 | 11/2002 | Richmond |
| 6,551,299 B2 | 4/2003 | Miyoshi et al. |
| 6,572,256 B2 | 6/2003 | Seaton et al. |
| 6,585,229 B2 | 7/2003 | Cote, Sr. et al. |
| 6,590,167 B2 | 7/2003 | Clare |
| 6,599,273 B1 | 7/2003 | Lopez |
| 6,623,455 B2 | 9/2003 | Small et al. |
| 6,629,956 B1 | 10/2003 | Polidoro et al. |
| 6,651,956 B2 | 11/2003 | Miller |
| 6,663,586 B2 | 12/2003 | Verkaart et al. |
| 6,689,108 B2 | 2/2004 | Lavi et al. |
| 6,726,672 B1 | 4/2004 | Hanly et al. |
| 6,793,651 B1 | 9/2004 | Bennett et al. |
| 6,813,868 B2 | 11/2004 | Baldwin et al. |
| 6,854,620 B2 | 2/2005 | Ramet |
| 6,877,530 B2 | 4/2005 | Osborne et al. |
| 6,908,459 B2 | 6/2005 | Harding et al. |
| 6,915,823 B2 | 7/2005 | Osborne et al. |
| 6,948,522 B2 | 9/2005 | Newbrough et al. |
| 6,953,450 B2 | 10/2005 | Baldwin et al. |
| 6,985,870 B2 | 1/2006 | Martucci et al. |
| 6,991,002 B2 | 1/2006 | Osborne et al. |
| 6,994,315 B2 | 2/2006 | Ryan et al. |
| 6,997,917 B2 | 2/2006 | Niedospial, Jr. et al. |
| 7,017,623 B2 | 3/2006 | Tribble et al. |
| 7,086,431 B2 | 8/2006 | D'Antonio et al. |
| 7,117,902 B2 | 10/2006 | Osborne |
| 7,128,105 B2 | 10/2006 | Tribble et al. |
| 7,163,035 B2 | 1/2007 | Khan et al. |
| 7,194,336 B2 | 3/2007 | DiGianfilippo et al. |
| 7,317,967 B2 | 1/2008 | DiGianfilippo et al. |
| 7,343,224 B2 | 3/2008 | DiGianfilippo et al. |
| 7,343,943 B2 | 3/2008 | Khan et al. |
| 7,351,226 B1 | 4/2008 | Herskowitz |
| 7,392,638 B2 | 7/2008 | Baldwin et al. |
| 7,396,051 B2 | 7/2008 | Baldwin et al. |
| 7,418,981 B2 | 9/2008 | Baker et al. |
| 7,442,186 B2 | 10/2008 | Blomquist |
| 7,488,311 B2 | 2/2009 | Domkowski et al. |
| 7,499,581 B2 | 3/2009 | Tribble et al. |
| 7,527,619 B2 | 5/2009 | Domkowski et al. |
| 7,530,974 B2 | 5/2009 | Domkowski et al. |
| 7,538,858 B2 | 5/2009 | Mackey |
| D594,120 S | 6/2009 | Berberich et al. |
| D596,291 S | 7/2009 | Berberich et al. |

(56) References Cited

U.S. PATENT DOCUMENTS

| | | |
|---|---|---|
| 7,566,326 B2 | 7/2009 | Duchon et al. |
| 7,610,115 B2 | 10/2009 | Rob et al. |
| 7,632,261 B2 | 12/2009 | Zinger et al. |
| 7,654,976 B2 | 2/2010 | Peterson et al. |
| 7,681,606 B2 | 3/2010 | Khan et al. |
| 7,703,483 B2 | 4/2010 | Hartman et al. |
| D616,092 S | 5/2010 | Domkowski et al. |
| 7,717,897 B2 | 5/2010 | Burg et al. |
| D620,108 S | 7/2010 | Eitenmueller et al. |
| 7,758,560 B2 | 7/2010 | Connell et al. |
| 7,789,850 B2 | 9/2010 | Roger |
| 7,814,731 B2 | 10/2010 | Bender et al. |
| 7,850,051 B2 | 12/2010 | Py et al. |
| 7,882,863 B2 | 2/2011 | Pestotnik et al. |
| 7,900,658 B2 | 3/2011 | Osborne et al. |
| 7,913,720 B2 | 3/2011 | Tribble et al. |
| 7,963,954 B2 | 6/2011 | Kavazov |
| 7,967,202 B2 | 6/2011 | Durrell et al. |
| 7,981,381 B2 | 7/2011 | Lurvey et al. |
| 7,997,304 B2 | 8/2011 | Ranalletta et al. |
| 8,034,041 B2 | 10/2011 | Domkowski et al. |
| 8,075,545 B2 | 12/2011 | Moy et al. |
| 8,091,727 B2 | 1/2012 | Domkowski |
| 8,091,860 B2 | 1/2012 | Thompson et al. |
| 8,104,644 B2 | 1/2012 | Py et al. |
| 8,140,351 B2 | 3/2012 | Tribble et al. |
| 8,141,601 B2 | 3/2012 | Fehr et al. |
| 8,151,835 B2 | 4/2012 | Khan et al. |
| 8,162,903 B2 | 4/2012 | Reilly et al. |
| 8,162,914 B2 | 4/2012 | Kraushaar et al. |
| D660,423 S | 5/2012 | Hermle |
| 8,197,459 B2 | 6/2012 | Jansen et al. |
| 8,206,367 B2 | 6/2012 | Warren et al. |
| D664,647 S | 7/2012 | Becker |
| D664,648 S | 7/2012 | Becker |
| D664,649 S | 7/2012 | Becker |
| 8,216,207 B2 | 7/2012 | Moy et al. |
| 8,220,504 B2 | 7/2012 | Hartman et al. |
| 8,221,382 B2 | 7/2012 | Moy et al. |
| 8,225,824 B2 | 7/2012 | Eliuk et al. |
| 8,225,826 B2 | 7/2012 | Horppu et al. |
| 8,231,567 B2 | 7/2012 | Tennican et al. |
| 8,241,265 B2 | 8/2012 | Moy et al. |
| 8,267,912 B2 | 9/2012 | Ferris |
| 8,287,513 B2 | 10/2012 | Ellstrom et al. |
| 8,328,082 B1 | 12/2012 | Bochenko et al. |
| 8,336,587 B2 | 12/2012 | Rosenquist et al. |
| 8,350,645 B2 | 1/2013 | Chong et al. |
| 8,353,318 B2 | 1/2013 | Ranalletta et al. |
| 8,356,644 B2 | 1/2013 | Chong et al. |
| 8,357,137 B2 | 1/2013 | Yandell |
| 8,381,776 B2 | 2/2013 | Horppu |
| 8,382,696 B2 | 2/2013 | Beiriger et al. |
| 8,403,905 B2 | 3/2013 | Yow |
| 8,409,165 B2 | 4/2013 | Niedospial, Jr. et al. |
| 8,414,554 B2 | 4/2013 | Garfield et al. |
| 8,425,487 B2 | 4/2013 | Beiriger et al. |
| 8,449,521 B2 | 5/2013 | Thorne, Jr. et al. |
| 8,506,548 B2 | 8/2013 | Okiyama |
| 8,522,832 B2 | 9/2013 | Lopez et al. |
| 8,551,037 B2 | 10/2013 | Suchecki et al. |
| 8,567,235 B2 | 10/2013 | Bojan et al. |
| 8,562,584 B2 | 11/2013 | Beiriger et al. |
| 8,602,067 B2 | 12/2013 | Kuhni et al. |
| 8,608,723 B2 | 12/2013 | Lev et al. |
| 8,622,985 B2 | 1/2014 | Ellstrom |
| 8,679,075 B2 | 3/2014 | Lurvey et al. |
| 8,684,994 B2 | 4/2014 | Lev et al. |
| 8,701,696 B2 | 4/2014 | Guala |
| 8,702,675 B2 | 4/2014 | Imai |
| 8,720,496 B2 | 5/2014 | Huwiler et al. |
| 8,721,612 B2 | 5/2014 | Domkowski et al. |
| 8,721,614 B2 | 5/2014 | Takemoto et al. |
| 8,763,326 B2 | 6/2014 | Lev et al. |
| 8,795,231 B2 | 8/2014 | Chong et al. |
| 8,821,436 B2 | 9/2014 | Mosler et al. |
| 8,834,444 B2 | 9/2014 | Domkowski |
| 8,852,147 B2 | 10/2014 | Callan et al. |
| 8,863,788 B2 | 10/2014 | Ranalletta et al. |
| 8,864,725 B2 | 10/2014 | Ranalletta et al. |
| 8,864,737 B2 | 10/2014 | Hasegawa et al. |
| 8,870,832 B2 | 10/2014 | Raday et al. |
| 8,882,739 B2 | 11/2014 | Domkowski et al. |
| 8,911,421 B2 | 12/2014 | Domkowski et al. |
| D721,803 S | 1/2015 | Dubach |
| 8,926,554 B2 | 1/2015 | Okuda et al. |
| 8,958,112 B2 | 2/2015 | Matsui et al. |
| D724,198 S | 3/2015 | Oostman et al. |
| 8,973,622 B2 | 3/2015 | Lopez et al. |
| 8,979,792 B2 | 3/2015 | Lev et al. |
| 9,043,019 B2 | 5/2015 | Eliuk et al. |
| 9,056,164 B2 | 6/2015 | Tate et al. |
| 9,057,363 B2 | 6/2015 | Capone |
| 9,057,370 B2 | 6/2015 | Mundt et al. |
| 9,060,923 B2 | 6/2015 | Hossainy |
| 9,061,130 B2 | 6/2015 | Truitt et al. |
| 9,079,686 B2 | 7/2015 | Domkowski et al. |
| 9,089,474 B2 | 7/2015 | Cederschiöld |
| 9,101,717 B2 | 8/2015 | Mansour et al. |
| 9,132,063 B2 | 9/2015 | Lev et al. |
| 9,139,316 B2 | 9/2015 | Husnu et al. |
| 9,144,646 B2 | 9/2015 | Barron, III et al. |
| 9,149,576 B2 | 10/2015 | Bullington et al. |
| 9,198,832 B2 | 12/2015 | Moy et al. |
| 9,211,231 B2 | 12/2015 | Mansour et al. |
| 9,212,762 B2 | 12/2015 | Duncan |
| 9,242,039 B2 | 1/2016 | Valk et al. |
| 9,345,641 B2 | 5/2016 | Krause et al. |
| 9,345,643 B2 | 5/2016 | Okiyama |
| 9,381,135 B2 | 7/2016 | Reynolds et al. |
| 9,381,137 B2 | 7/2016 | Garfield et al. |
| 9,402,786 B2 | 8/2016 | Petrone |
| D774,192 S | 12/2016 | Fuchs |
| D775,325 S | 12/2016 | Larson et al. |
| 9,511,989 B2 | 12/2016 | Lopez et al. |
| D803,396 S | 11/2017 | Oberkircher et al. |
| 9,827,163 B2 | 11/2017 | Lopez et al. |
| D804,651 S | 12/2017 | Loonan |
| 9,883,987 B2 | 2/2018 | Lopez et al. |
| 2002/0179544 A1 | 12/2002 | Johnson et al. |
| 2003/0236500 A1 | 12/2003 | Scheu |
| 2004/0035743 A1 | 2/2004 | Tighe et al. |
| 2004/0087888 A1 | 5/2004 | Digianfilippo et al. |
| 2004/0116891 A1 | 6/2004 | Curutcharry |
| 2005/0059952 A1 | 3/2005 | Giuliano et al. |
| 2005/0096627 A1 | 5/2005 | Howard |
| 2005/0131357 A1 | 6/2005 | Denton et al. |
| 2005/0230575 A1 | 10/2005 | Zelenski et al. |
| 2005/0252572 A1 | 11/2005 | Khan et al. |
| 2005/0252574 A1 | 11/2005 | Khan et al. |
| 2006/0064053 A1 | 3/2006 | Bollish et al. |
| 2006/0259195 A1 | 11/2006 | Eliuk et al. |
| 2007/0007478 A1 | 1/2007 | Leinsing et al. |
| 2007/0088252 A1 | 4/2007 | Pestotnik et al. |
| 2007/0106244 A1 | 5/2007 | Mosler et al. |
| 2008/0065006 A1 | 3/2008 | Roger et al. |
| 2008/0086094 A1 | 4/2008 | Peters |
| 2008/0114328 A1 | 5/2008 | Doherty et al. |
| 2008/0125897 A1 | 5/2008 | DiGianfilippo et al. |
| 2008/0169043 A1 | 7/2008 | Osborne et al. |
| 2008/0169044 A1 | 7/2008 | Osborne et al. |
| 2008/0177222 A1 | 7/2008 | De Marco et al. |
| 2008/0195416 A1 | 8/2008 | Tribble et al. |
| 2008/0199353 A1 | 8/2008 | Mlodzinski et al. |
| 2008/0287920 A1 | 11/2008 | Fangrow et al. |
| 2009/0012449 A1 | 1/2009 | Lee et al. |
| 2009/0050216 A1 | 2/2009 | Trocki et al. |
| 2009/0067973 A1 | 3/2009 | Eliuk et al. |
| 2009/0069743 A1 | 3/2009 | Krishnamoorthy et al. |
| 2009/0082649 A1 | 3/2009 | Muller et al. |
| 2009/0088687 A1 | 4/2009 | Yardimci et al. |
| 2009/0099547 A1 | 4/2009 | Radmer |
| 2009/0101576 A1 | 4/2009 | Rohde et al. |
| 2009/0126825 A1 | 5/2009 | Eliuk et al. |

(56) References Cited

U.S. PATENT DOCUMENTS

| | | |
|---|---|---|
| 2009/0145509 A1 | 6/2009 | Baker et al. |
| 2009/0149743 A1 | 6/2009 | Barron et al. |
| 2009/0163860 A1 | 6/2009 | Patrick et al. |
| 2009/0177149 A1 | 7/2009 | Childers et al. |
| 2009/0198215 A1 | 8/2009 | Chong et al. |
| 2009/0254031 A1 | 10/2009 | Lee |
| 2009/0306621 A1 | 12/2009 | Thome, Jr. et al. |
| 2010/0024904 A1 | 2/2010 | Hoffman et al. |
| 2010/0049157 A1 | 2/2010 | Fangrow |
| 2010/0121246 A1 | 5/2010 | Peters et al. |
| 2010/0245056 A1 | 9/2010 | Braun et al. |
| 2010/0276034 A1 | 11/2010 | Gonnelli et al. |
| 2010/0280430 A1 | 11/2010 | Caleffi et al. |
| 2011/0062703 A1 | 3/2011 | Lopez et al. |
| 2011/0087164 A1 | 4/2011 | Mosler et al. |
| 2011/0112501 A1 | 5/2011 | Garfield et al. |
| 2011/0178493 A1 | 7/2011 | Okiyama |
| 2011/0196304 A1 | 8/2011 | Kramer et al. |
| 2012/0157914 A1 | 1/2012 | Stroup |
| 2012/0041391 A1 | 2/2012 | Fangrow et al. |
| 2012/0067429 A1 | 3/2012 | Mosler et al. |
| 2012/0078091 A1 | 3/2012 | Suchecki et al. |
| 2012/0109077 A1 | 5/2012 | Ryan |
| 2012/0123298 A1 | 5/2012 | Mendels et al. |
| 2012/0197184 A1 | 8/2012 | Okuda et al. |
| 2012/0298254 A1 | 11/2012 | Brem et al. |
| 2012/0302986 A1 | 11/2012 | Brem et al. |
| 2013/0006214 A1 | 1/2013 | Garfield et al. |
| 2013/0053815 A1 | 2/2013 | Mucientes et al. |
| 2013/0180618 A1 | 7/2013 | Py |
| 2013/0218121 A1 | 8/2013 | Waller et al. |
| 2013/0220484 A1 | 8/2013 | De Marco |
| 2013/0292002 A1 | 11/2013 | Lopez |
| 2014/0124087 A1 | 5/2014 | Anderson et al. |
| 2014/0124092 A1 | 5/2014 | Gonnelli et al. |
| 2014/0135732 A1 | 5/2014 | Spronken et al. |
| 2014/0150925 A1 | 6/2014 | Sjogren et al. |
| 2014/0174596 A1 | 6/2014 | Lopez |
| 2014/0261727 A1 | 9/2014 | Mansour et al. |
| 2014/0261860 A1 | 9/2014 | Heath |
| 2014/0261877 A1 | 9/2014 | Ivosevic et al. |
| 2014/0263614 A1 | 9/2014 | Keefe et al. |
| 2014/0276386 A1 | 9/2014 | Mansour et al. |
| 2014/0323970 A1 | 10/2014 | Duncan |
| 2015/0008664 A1 | 1/2015 | Tachizaki |
| 2015/0025453 A1 | 1/2015 | Ledford et al. |
| 2015/0068640 A1 | 3/2015 | Garfield et al. |
| 2015/0101707 A1 | 4/2015 | Ranalletta et al. |
| 2015/0119820 A1 | 4/2015 | Kanamoto |
| 2015/0133879 A1 | 5/2015 | Kanamoto et al. |
| 2015/0151041 A1 | 6/2015 | Yodfat et al. |
| 2015/0161354 A1 | 6/2015 | Biomquist |
| 2015/0209230 A1 | 7/2015 | Lev et al. |
| 2015/0209233 A1 | 7/2015 | Fukuoka |
| 2015/0209495 A1 | 7/2015 | Biset et al. |
| 2015/0209572 A1 | 7/2015 | Garfield et al. |
| 2015/0250680 A1 | 9/2015 | Browka et al. |
| 2015/0250681 A1 | 9/2015 | Lev et al. |
| 2015/0257977 A1 | 9/2015 | Bochenko et al. |
| 2015/0265500 A1 | 9/2015 | Russo et al. |
| 2015/0283322 A1 | 10/2015 | Hachey et al. |
| 2015/0297881 A1 | 10/2015 | Sanders et al. |
| 2015/0314066 A1 | 11/2015 | Shimizu |
| 2016/0081879 A1 | 3/2016 | Garfield et al. |
| 2016/0250102 A1 | 9/2016 | Garfield et al. |
| 2016/0256632 A1 | 9/2016 | Fangrow |
| 2017/0079883 A1 | 3/2017 | Lopez |
| 2017/0129763 A1 | 5/2017 | Fangrow, Jr. |
| 2018/0055735 A1 | 3/2018 | Lopez |
| 2018/0177940 A1 | 6/2018 | Hachey |
| 2018/0207063 A1 | 7/2018 | Lopez |
| 2018/0272117 A1 | 9/2018 | Fangrow |

FOREIGN PATENT DOCUMENTS

| | | |
|---|---|---|
| EP | 1 563 819 | 8/2005 |
| EP | 1 997 471 | 12/2008 |
| JP | 55-173339 | 12/1980 |
| JP | 06-343706 | 12/1994 |
| JP | 2002-355318 | 12/2002 |
| JP | 2003-144546 | 5/2003 |
| WO | WO 1997/14493 | 4/1997 |
| WO | WO 1999/63547 | 12/1999 |
| WO | WO 2001/03757 | 1/2001 |
| WO | WO 2001/039874 | 6/2001 |
| WO | WO 2002/04065 | 1/2002 |
| WO | WO 2005/041846 | 5/2005 |
| WO | WO 2005/110007 | 11/2005 |
| WO | WO 2005/123162 | 12/2005 |
| WO | WO 2007/033013 | 3/2007 |
| WO | WO 2007/061424 | 5/2007 |
| WO | WO 2007/079305 | 7/2007 |
| WO | WO 2007/148708 | 12/2007 |
| WO | WO 2008/052140 | 5/2008 |
| WO | WO 2008/128074 | 10/2008 |
| WO | WO 2009/060419 | 5/2009 |
| WO | WO 2010/111546 | 9/2010 |
| WO | WO 2011/012313 | 2/2011 |
| WO | WO 2011/058545 | 5/2011 |
| WO | WO 2011/058548 | 5/2011 |
| WO | WO 2011/091542 | 8/2011 |
| WO | WO 2011/091543 | 8/2011 |
| WO | WO 2011/104711 | 9/2011 |
| WO | WO 2011/104712 | 9/2011 |
| WO | WO 2011/150037 | 12/2011 |
| WO | WO 2012/119225 | 9/2012 |
| WO | WO 2013/096911 | 6/2013 |
| WO | WO 2014/122643 | 8/2014 |
| WO | WO 2014/181320 | 11/2014 |
| WO | WO 2015/029020 | 3/2015 |
| WO | WO 2015/077184 | 5/2015 |
| WO | WO 2015/077466 | 5/2015 |
| WO | WO 2016/010909 | 1/2016 |
| WO | WO 2017/096072 | 6/2017 |
| WO | WO 2018/022640 | 2/2018 |

OTHER PUBLICATIONS

U.S. Appl. No. 29/586,575, filed Dec. 5, 2016, Fangrow.
Autoyec 50, from KRZ, Dec. 6, 2007.
B. Braun Medical Inc. Two-Bag Irrigation Set, Two Non-vented Spikes, dated Jul. 2012, in 1 page.
BioExpert International Inc., Company overview, credentials for Rabin Jamaleddine, Nabil Kereknawi, and Danica Robillard Corso, copyright 2010 BioExpert Internationai Inc. in 3 pages [retrieved on Jan. 6, 2015; Publication Date Unknown]; accessed on the world wide web at http://bioexpert.ca/about.html.
Cato (Computer Aided Therapy For Oncology)—Reference Manual—Vienna, May 2005, 255 pgs.
ISO/Tech Design, QC, Canada, "CHEMOSPHERE," product brochure, in 2 pages [Publication Date Unknown].
Clearlink Needleless IV Access System, dated Aug. 2007, in 2 pages.
CytoCare, by Health Robotics, Brochure, Date Unknown, downloaded on May 25, 2012 from http://www.health-robotics.com/smartedit/downloads/en/cytocare7.pdf, 6 pages.
European Extend Search Report, re EP Application No. 12859749.9, dated Nov. 17, 2015.
Exacta-Mix 2400, from Baxa, which appears to have a date of 2007, 2 pages.
Flickinger, Bruce, "Misperceptions Cloud the Issue of Sterile Drug Compounding," Jun. 2007.
Fox, Brent I., "Pharmacy Automation and Technology: Automated Intravenous Preparation: Robots for the Pharmacy," Hospital Pharmacy, vol. 44, Mar. 2009, pp. 255-257.

(56) References Cited

OTHER PUBLICATIONS

Healthmark, "Hospital Medication Preparation, Packaging and Dispensing," Chemo Drug Preparation/Administration in 2 pages [retrieved on Jan. 6, 2015; Publication Date Unknown]; accessed on the world wide web at http://www.healthmark.ca/2-36-88-Chemo-Drug-Preparation-Administration_en.html.
Healthmark, "Hospital Medication Preparation, Packaging and Dispensing," Chemosphere, Sterile Chemo Compounding (Isolator) in 1 page [retrieved on Jan. 6, 2015; Publication Date Unknown]; accessed on the world wide web at http://www.healthmark.ca/2-36-10-ChemoSphere_en.html?ProduitID=244.
Healthmark, "Hospital Medication Preparation, Packaging and Dispensing" in 1 page [retrieved on Jan. 6, 2015; Publication Date Unknown]; accessed on the world wide web at http://www.healthmark.ca/2-en-Hospital-Medication-Preparation-Packaging-and-Dispensing.html.
Healthmark, "Hospital Medication Preparation, Packaging and Dispensing," Oncology Preparation and Administration in 1 page [retrieved on Jan. 6, 2015; Publication Date Unknown]; accessed on the world wide web at http://www.healthmark.ca/2-36-10-COMPANY-PROFILEHospital-en.html.
Healthmark, "Hospital Medication Preparation, Packaging and Dispensing," Phocus RX (Camera Verification System), Remote Rx Checking of admixtures in 2 pages [retrieved on Jan. 6, 2015; Publication Date Unknown]; accessed on the world wide web at http://www.healthmark.ca/2-36-10-PHOCUS-Rx-Camera-Verification-System-_en.html?ProduitID=229.
Healthmark, "New Product Items" in 1 page [retrieved on Jan. 6, 2015; Publication Date Unknown]; accessed on the world wide web at http://www.healthmark.ca/home.html.
Healthmark, "Introducing the Precifill Dispensing Pump" product brochure in 2 pages [Publication Date Unknown].
Integra Brochure, from Eurospital, Brochure acquired in Mar. 2012.
International Preliminary Report on Patentability re PCT Application No. PCT/US2012/071493, dated Jun. 24, 2014.
International Report on Patentability and Written Opinion re PCT Application No. PCT/US2010/043451, dated Feb. 9, 2012.
Neo Care Medical Products: Product Catalog, dated Jun. 2008, in 38 pages.
Grifols International, S.A., "PHOCUS Rx, Remote IV Compounding Validation" product brochure and "Product Description Sheet" in 13 pages [Publication Date unknown but may be May 29, 2013].
Pinnacle TPN Management System, from B Braun. downloaded May 5, 2009 from http://www.bbraunusa.com/index.cfm?uuid=7386ADF065B05CD0D22AF700339AA4092, 1 page.
"Precifill," Trademark search (TESS) in 1 page, [retrieved on Jan. 6, 2015; Application Filing Date of Sep. 30, 2011]; accessed on the world wide web at http://tmsearch.uspto.gov/bin/showfield?f=doc&state=4807:gz67gx.3.1.
Product detail for "NAMIC® Closed Fluid Systems" from Navilyst Medical, downloaded on May 11, 2010 from http://www.navilystmedical.com/Products/index.cfm/19, 2 pages.
Product detail for "RapidFill™ Automated Syringe Filler," from Baxa, downloaded on Mar. 31, 2010 from http://www.baxa/com/PharmacyProducts/AutomatedFillingSystems/ProductDetail/?id=B1, 2 pages.
Product detail for "Summit Medical DirectFlow" micro infusion extension set from Summit Medical Technologies, downloaded on May 10, 2010 from http://summitmedtech.com/p6line.php, 1 page.
Riva, downloaded in Apr. 2009 from http://www.rivasystem.com, 6 pages.
SmartSite Safety Disposables, with copyright notice dated 2004.
Smith. "Lifesaving Cancer Drugs May Put Workers' Lives at Risk," downloaded on Jul. 12, 2010 from http://www.msnbc.msn.com/id/38114586/ns/health-cancer, 7 pages.
Spiros—Closed Male Connector, published Jan. 22, 2008.
Technical Data sheet for Analog Amplifiers Type VA, models V8-C and V8-D, STM Sensors dated Dec. 2007, 4 pages.
Technical Data sheet for Through Beam Sensors Type G2, 1480 nm, STM Sensors dated Dec. 2009, 2 pages.
Technical Data sheet for Through Beam Sensors Type G2, 645 nm, STM Sensors dated Sep. 2008, 2 pages.
User Guide for medOC 1xx Basic, Neo Care Medical Products GmbH, Version Jun. 2008, 23 pages.
User Manual for medOC 3xx /6xx 18xx, Neo Care Medical Products GmbH, Version May 2008, 44 pages.

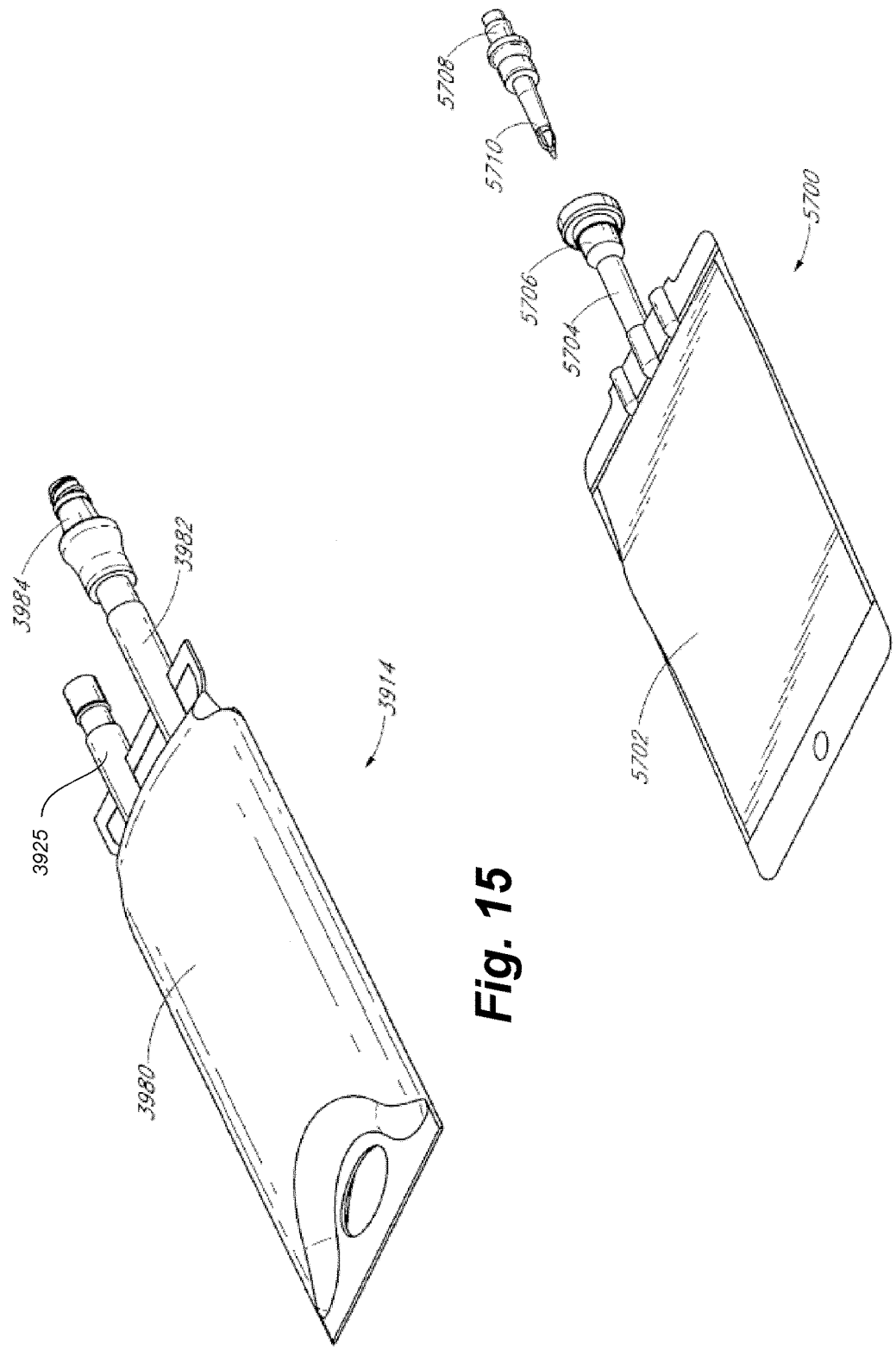

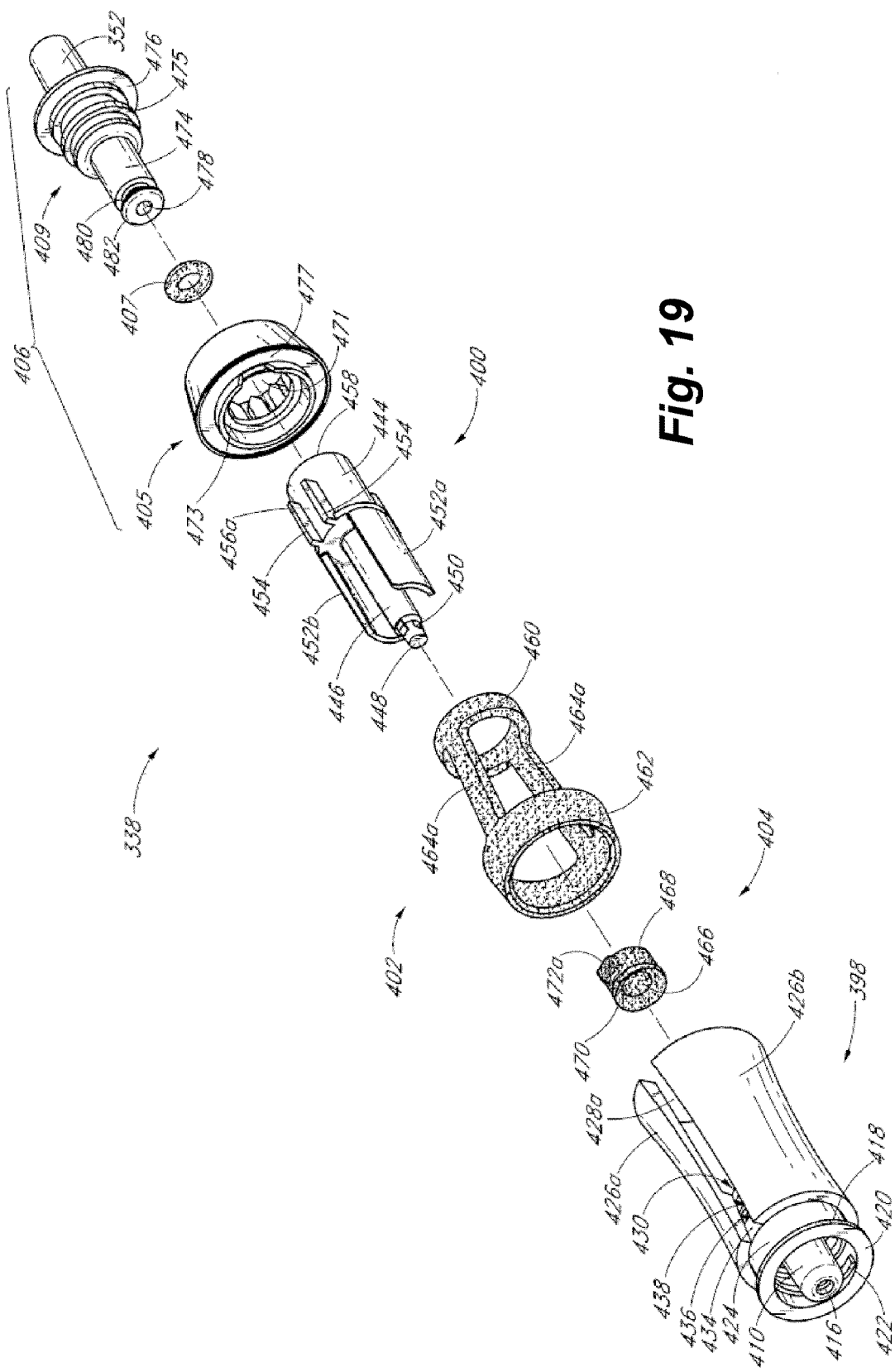

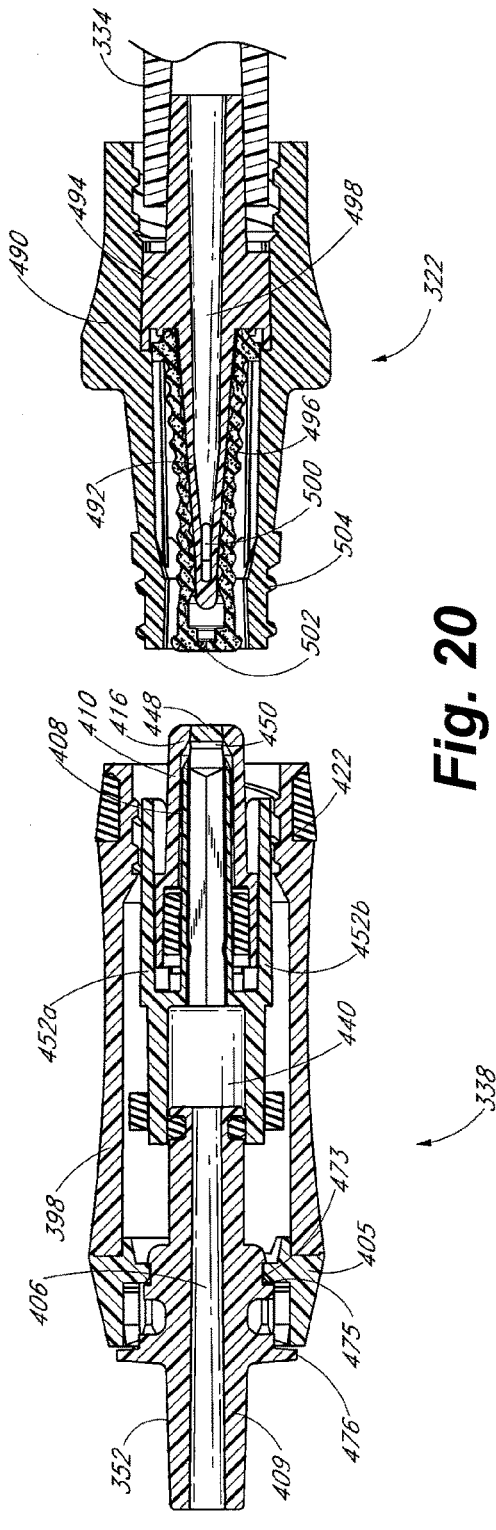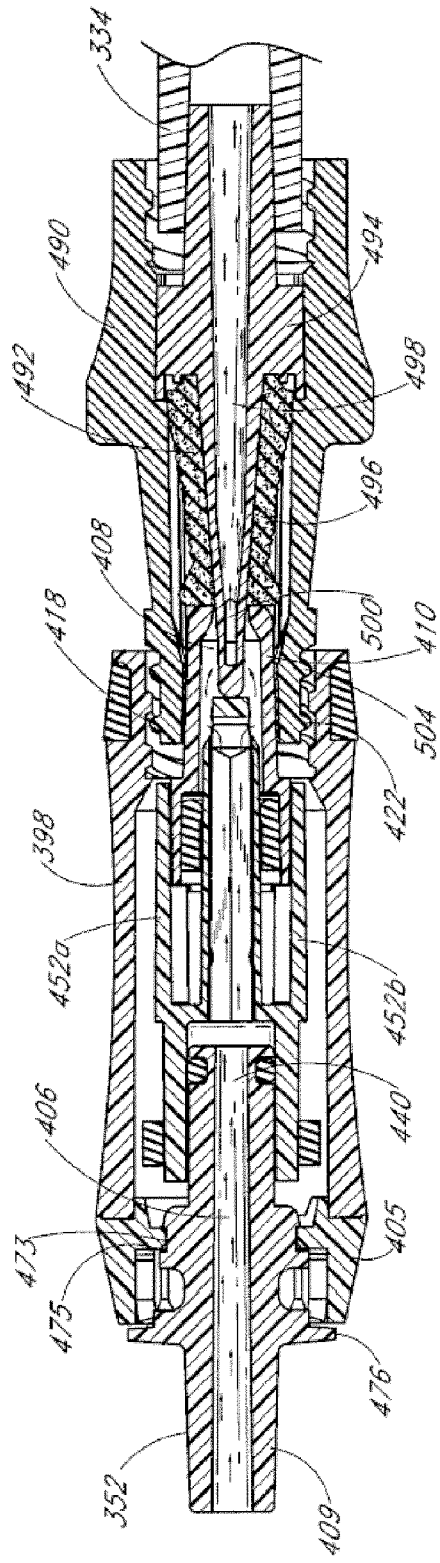

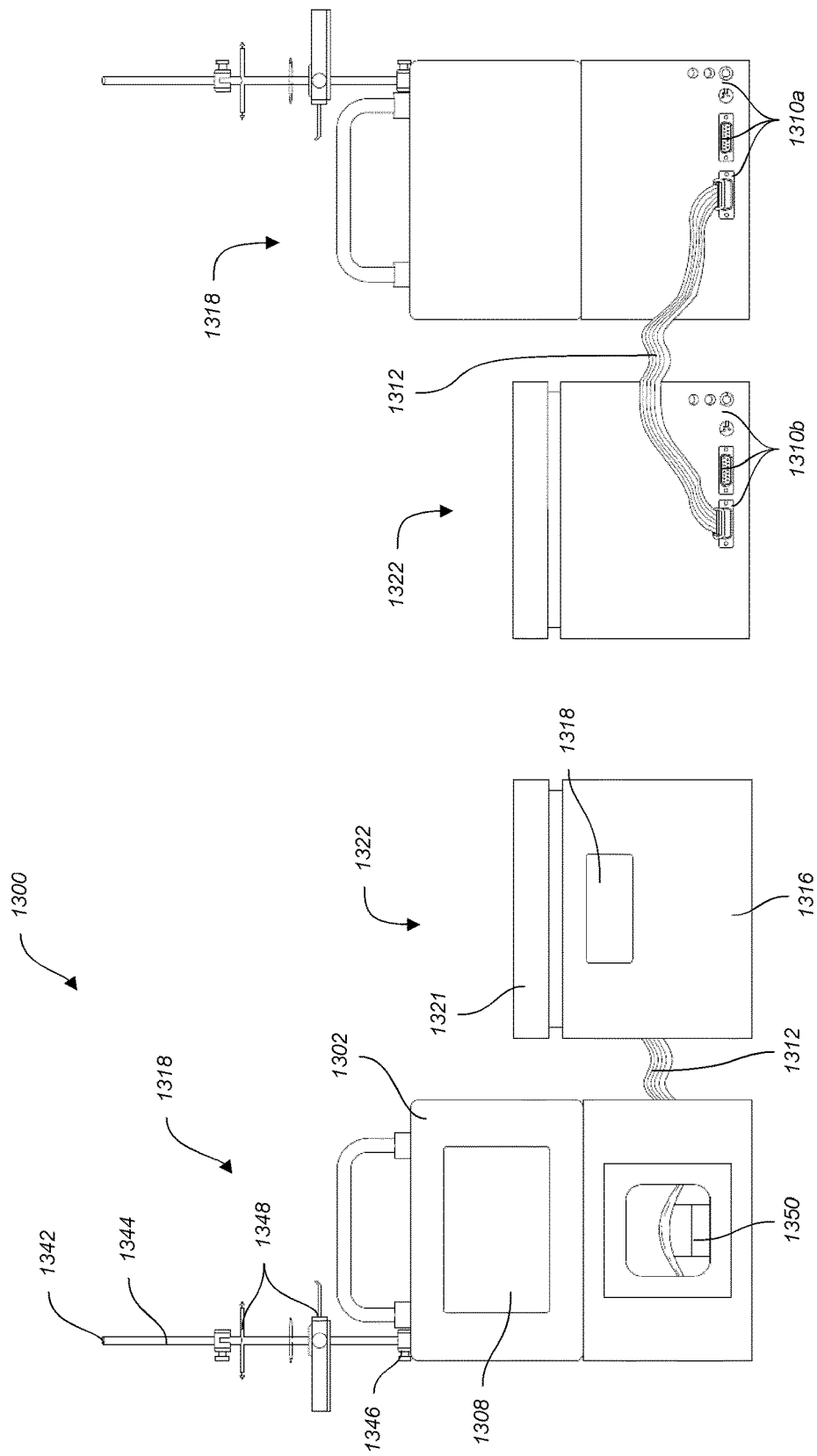

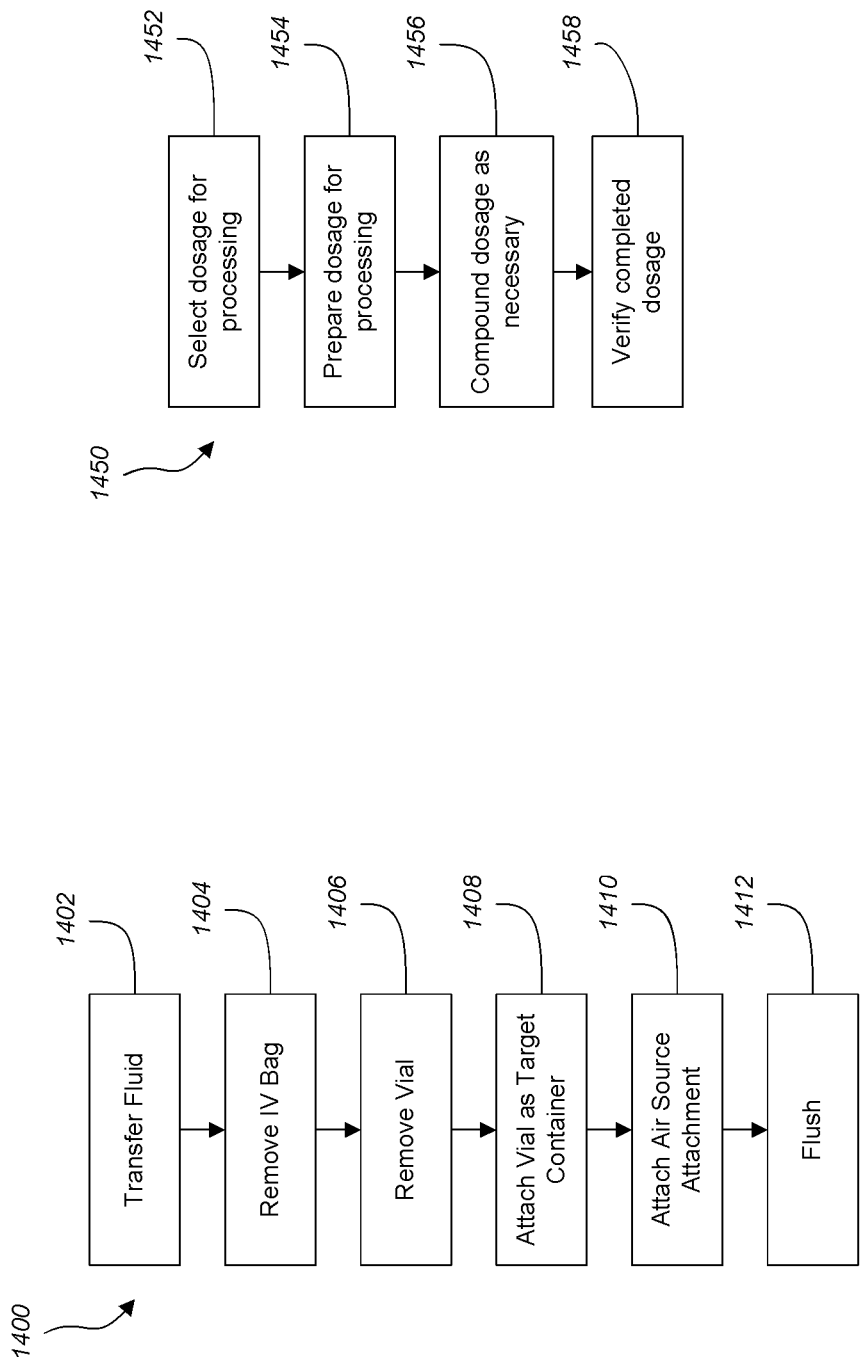

FLUID TRANSFER DEVICES AND METHODS OF USE

CROSS-REFERENCE TO RELATED APPLICATIONS

This application is a continuation of U.S. patent application Ser. No. 14/310,942, titled "FLUID TRANSFER DEVICES AND METHODS OF USE," filed Jun. 20, 2014, which is a continuation of PCT Patent Application No. PCT/US2012/071493, titled "FLUID TRANSFER DEVICES AND METHODS OF USE," filed Dec. 21, 2012, which claims the benefit of U.S. Provisional Patent Application No. 61/579,622, titled "FLUID TRANSFER DEVICES AND METHODS OF USE," filed Dec. 22, 2011. The entire contents of each of the above-referenced patent applications are incorporated by reference herein and made a part of this specification. Any and all applications for which a foreign or domestic priority claim is identified in the Application Data Sheet as filed with the present application are incorporated by reference under 37 CFR 1.57 and made a part of this specification.

INCORPORATION BY REFERENCE

U.S. Patent Publication No. 2011/0062703 (the "'703 Publication"), titled "FLUID TRANSFER DEVICES AND METHODS OF USE," filed on Jul. 28, 2010 as U.S. patent application Ser. No. 12/845,548, and published on Mar. 17, 2011 is hereby incorporated by reference in its entirety and made a part of this specification for all that it discloses.

U.S. Pat. No. 5,685,866 (the "'866 Patent"), titled "MEDICAL VALVE AND METHOD OF USE," filed on Nov. 4, 1994 as U.S. patent application Ser. No. 08/334,846, and granted on Nov. 11, 1997, is hereby incorporated by reference in its entirety and made a part of this specification for all that it discloses.

U.S. Patent Publication No. 2008/0287920 (the "'920 Publication"), titled "MEDICAL CONNECTOR WITH CLOSEABLE MALE LUER," filed on May 8, 2008 as U.S. patent application Ser. No. 12/117,568, and published on Nov. 20, 2008, is incorporated by reference in its entirety and made a part of this specification for all that it discloses.

U.S. Patent Publication No. 2010/0049157 (the "'157 Publication"), titled "ANTI-REFLUX VIAL ADAPTORS," filed on Aug. 19, 2009 as U.S. patent application No. 12/543,776, and published on Feb. 25, 2010, is hereby incorporated by reference in its entirety and made a part of this specification for all that it discloses.

U.S. Provisional Patent Application No. 61/557,793 (the "'793 Application"), filed Nov. 9, 2011, and titled "MEDICAL CONNECTORS WITH FLUID-RESISTANT MATING INTERFACES," is hereby incorporated by reference in its entirety and made a part of this specification for all that it discloses.

PCT Patent Application No. PCT/US2012/054289, filed Sep. 7, 2012, and titled "MEDICAL CONNECTORS WITH FLUID-RESISTANT MATING INTERFACES," is hereby incorporated by reference in its entirety and made a part of this specification for all that it discloses.

U.S. Patent Publication No. 2011/0282302 (the "'302 Publication"), titled "MEDICAL CONNECTORS AND METHODS OF USE," filed on May 12, 2011 as U.S. patent application Ser. No. 13/106,781, and published on Nov. 17, 2011, is hereby incorporated by reference in its entirety and made a part of this specification for all that it discloses.

BACKGROUND

Field of the Disclosure

Some embodiments of the invention relate generally to devices and methods for transferring fluid and specifically to devices and methods for transferring medical fluids.

Description of the Related Art

In some circumstances it can be desirable to transfer one or more fluids between containers. In the medical field, it is often desirable to dispense fluids in precise amounts and to store and to transport potentially dangerous fluids. Current fluid transfer devices and methods in the medical field suffer from various drawbacks, including high cost, low efficiency, intensive labor demands, and excessive fluid or vapor leakage. Some embodiments disclosed herein overcome one or more of these disadvantages.

SUMMARY OF SOME EMBODIMENTS

Some embodiments disclosed herein relate to systems and methods for transferring fluid from source containers to target containers.

In one embodiment a medical fluid transfer system includes a hose assembly having a first closable connector configured to couple to a source container and a second closable connector configured to couple to a target container. The system also includes a pump configured to transfer fluid through the hose assembly. The system also includes a destination sensor configured to output information about the second container. The system also includes a control system configured to receive instructions, including a fluid transfer instruction, operate the pump based on the fluid transfer instructions, receive information about the second container from the destination sensor, and operate the pump based on the information received from the destination sensor.

In some embodiments of the medical fluid transfer system, the destination sensor can be a weight sensor. The pump can be a positive displacement pump or a peristaltic pump. The control system can be configured to operate the peristaltic pump at variable speeds.

In some embodiments the hose assembly can have an elastomeric portion. The hose assembly can have a first connector and a second connector. The first connector can be configured to removably couple to the first container and the second connector can be configured to removably couple to the second container. The first connector can be a closable male connector and the second connector can be a closable male connector. The medical fluid transfer system can further include a sensor configured to detect whether the second connector is open.

In some embodiments the medical fluid transfer system can include a reservoir container. The reservoir container includes a reservoir body having an outer wall forming an internal cavity, the outer wall can be flexible. The reservoir container also includes a first engagement interface configured to couple to the first container. The reservoir container also include a second engagement interface coupled to the hose assembly. The reservoir container can be operable to transfer fluid from the first container to the internal cavity by compressing and decompressing the outer wall.

In some embodiments the control system can be configured to receive instructions from a remote source. The medical fluid transfer system can further include a scanner configured to scan information on the first container and the second container. The control system can be configured to receive information from the scanner and store the information received from the scanner.

In an embodiment of a method of transferring fluid using a medical fluid transfer system, the method includes receiving instructions, the instructions identifying a specified volume of fluid to transfer from a source container to a target container. The method also includes transferring fluid from the source container to the target container, wherein fluid is transferred via a hose assembly by a pump, wherein the hose assembly has a first closable connector coupled to the target container and a second closable connector coupled to the target container. The method also includes receiving information from a destination sensor, wherein the information identifies the amount of fluid transferred to the source container. The method also includes stopping the transfer of fluid when the specified volume of fluid is transferred to the target container based on the information received from the destination sensor.

In some embodiments the pump can be a peristaltic pump. The destination sensor can be a weight sensor and the information is the weight of the fluid transferred to the source container.

In some embodiments the method also includes preparing the weight sensor for the transfer of fluid by accounting for the weight of the target container prior to transferring fluid from the source container to the target container. In some embodiments the method also includes receiving an indication from the destination sensor that fluid is not being transferred to the target container, determining based on the information received from the destination sensor that the fluid from the source container has been depleted, and notifying a user that the source container has been depleted.

In some embodiments, the method can also include determining a threshold amount of fluid transferred from the source container to the target container, the threshold is an amount of fluid less than specified volume of fluid to transfer to the target container, identifying when the threshold has been satisfied based on information received from the destination sensor, and adjusting operational parameters of the pump to slow down the rate at which fluid is transferred from the source container after the threshold has been satisfied. The method can also include prompting a user to decouple the source container from the fluid transfer system when the fluid from the source container is depleted.

An embodiment of a hose assembly for the transfer of medical fluids includes a hose having a proximal end and a distal end. An elastomeric portion can be disposed between the proximal end and the distal end, the elastomeric portion can have a first portion and a second portion. The second portion can be more flexible than the first portion. The second portion is configured to couple to a peristaltic pump. The hose assembly also includes a first closable male connector coupled to the proximal end of the hose, the first connector configured to couple to a source container. The hose assembly also includes a second closable male connector coupled to the distal end of the hose, the second connector configured to couple to a target container. The hose assembly is configured to form a fluid flow path from the source container to the target container.

In an embodiment of a medical fluid transfer system for flushing a connector having a residual fluid contained therein, the system includes a fluid transfer station having a connector and a control system. The connector has a source connection portion and a target connection portion. The connector has a residual volume of a transfer fluid contained therein. The control system can be configured to draw a flushing fluid into the connector through the source connection portion, and drive at least a portion of the flushing fluid towards the target connection portion to expel at least a portion of the residual fluid from the connector.

In some embodiments of the medical fluid transfer system, the portion of residual fluid can be substantially all the residual fluid from the connector. The flushing fluid can be air. The control system can be configured to provide a prompt to a user to attach or confirm attachment of a flush receiving container to the target connection portion of the connector. The target connection portion of the connector can be configured to couple to a flush receiving container, the flush receiving container can be a source container for use during a fluid transfer operation. The flush receiving container can use the same type of fluid as the residual fluid. The control system can be further configured to receive instructions. The instructions can include fluid transfer instructions for transferring a specified volume of the transfer fluid. The control system can be further configured to actuate a fluid switch to close a fluid connection between the source connection portion of the connector and the transfer fluid and to establish a fluid connection between the source connection portion of the connector and the flushing fluid.

In some embodiments the medical fluid transfer system can also include a pump and the connector can be a hose assembly. The control system can be further configured control operation of the pump to draw a flushing fluid into the connector through the source connection portion and to drive at least a portion of the flushing fluid towards the target connection portion to expel at least a portion of the residual fluid from the connector.

In some embodiments the medical fluid transfer system can also include a syringe having a plunger and coupled to the connector. The control system can be further configured to retract the plunger on the syringe wherein retracting the plunger is configured to draw a flushing fluid into the connector through the source connection portion and advance the plunger to drive at least a portion of the flushing fluid towards the target connection portion to expel at least a portion of the residual fluid from the connector. The control system can be further configured to retract the plunger a second time to draw additional flushing fluid into the connector through the source connection portion, and advance the plunger a second time to drive at least a portion of the flushing fluid towards the target connection portion to expel at least a portion of the remaining residual fluid from the connector. The control system can be further configured to receive instructions, including fluid transfer instructions for transferring a specified volume of the transfer fluid. The control system can be further configured to calculate a transfer fluid sub-volume, the transfer fluid sub-volume being smaller than the specified volume of the transfer fluid, transfer the transfer fluid sub-volume from a source container to a target container by actuating the syringe plunger, and stop the fluid transfer to leave the residual volume of the transfer fluid in the connector as the residual fluid. Advancing the plunger can drive an expelled volume of the residual fluid into the target container, and the transfer fluid sub-volume and the expelled volume combine to substantially equal the specified volume of the transfer fluid. The fluid transfer instructions can further include a specified volume of a diluting fluid. The system can be further configured to calculate a diluting fluid sub-volume, the diluting fluid sub-volume being smaller than the specified volume of the diluting fluid and transfer the diluting fluid sub-volume into the target container. The diluting fluid can be configured to be used as the flushing fluid. When advanced, the plunger can expel a diluting fluid flush volume of the diluting fluid into the target container, and the diluting fluid sub-volume and the diluting fluid flush volume combine to substantially equal the specified volume of the diluting fluid.

BRIEF DESCRIPTION OF THE DRAWINGS

Certain embodiments of the invention will now be discussed in detail with reference to the following figures. These figures are provided for illustrative purposes only, and the embodiments are not limited to the subject matter illustrated in the figures.

FIG. 15 shows an example embodiment of an IV bag assembly that can be used with the fluidics system of FIG. 5.

FIG. 16 shows another example embodiment of an IV bag assembly that can be used with the fluidics system of FIG. 5.

FIG. 19 is an exploded view of the male connector portion of FIG. 17.

FIG. 20 is a cross sectional view of the male connector portion of FIG. 17 with a female connector in an unengaged configuration.

FIG. 21 is a cross sectional view of the male connector portion of FIG. 17 with a female connector in an engaged configuration.

FIG. 62 is a front view of the system of FIG. 61.

FIG. 63 is a back view of the system of FIG. 61.

FIG. 70 is an example embodiment of a method of flushing a fluid.

FIG. 71 is an example embodiment of a method for using a workflow and/or data management system.

DETAILED DESCRIPTION OF SOME EXAMPLE EMBODIMENTS

The following detailed description is now directed to certain specific example embodiments of the disclosure. In this description, reference is made to the drawings wherein like parts are designated with like numerals throughout the description and the drawings.

In many circumstances fluid is transferred from a source container to a target container. In some instances, it can be desirable to transfer precise amounts of a fluid, such as a medication, into the target container. For example, in some embodiments a medication can be stored in a vial or other container, and a precise dosage amount of the medication can be extracted and transferred to a target device so that the dosage amount can be delivered to a patient. In some embodiments, fluid from multiple source containers can be combined, or compounded, into a single target container. For example, in some embodiments a mixture of medications can be created in the target container, or a concentrated medication can be combined with a diluent in the target container. To achieve the desired proportions of fluids, it can be desirable to precisely measure the amounts of fluids transferred into the target container. Also, precisely measuring the amount of fluid transferred from the source container to the target container can reduce the amount of fluid wasted (e.g., when more fluid than necessary is withdrawn from the source container). Reduction of waste is desirable because, for example, in some instances the fluid being transferred can be expensive.

Some embodiments disclosed herein provide fluid transfer devices for transferring precise amounts of fluid from one or more source containers into one or more target containers.

In some embodiments, it can be desirable to transfer fluids from a source container to a target container using a sealed system. In some embodiments, exposing the fluid to ambient air can allow contaminants to enter the fluid or cause an undesirable reaction with the fluid. Some medications (e.g., chemotherapy medications) can be harmful to an unintended recipient. Therefore, it can be desirable to prevent or reduce exposure of the fluid being transferred to the ambient air or area outside the fluid transfer system. In some embodiments, a fluid transfer system that prevents or reduces exposure of the fluid to the area outside the fluid transfer system can render other expensive equipment (e.g., a clean room) unnecessary, thereby reducing the cost associated with transferring the fluids.

Some embodiments disclosed herein provide a fluid transfer device for transferring fluid while preventing, reducing, or minimizing the amount of contact the fluid has with the ambient air or area outside the fluid transfer system.

Figure 1:
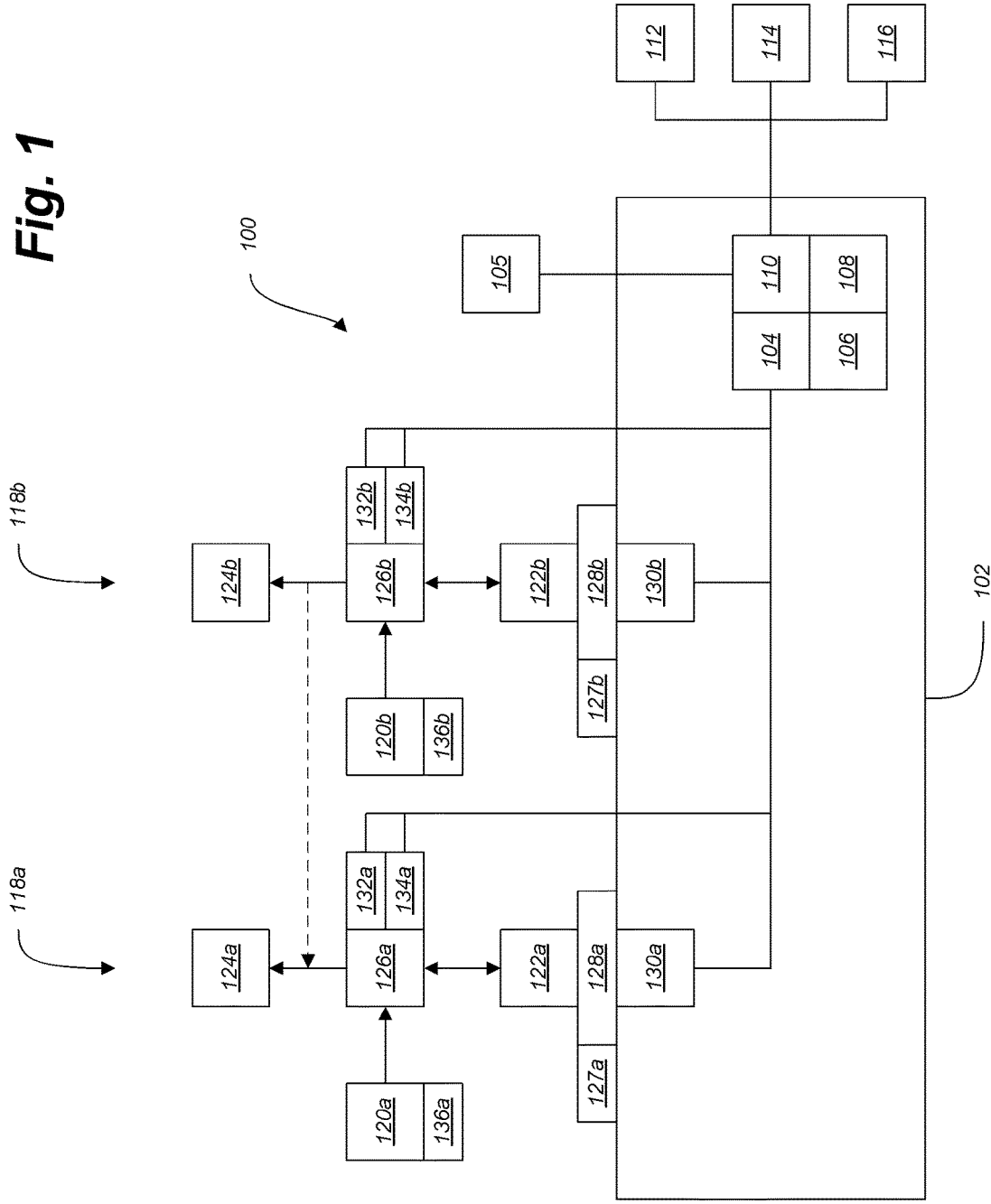
FIG. 1 schematically shows an example embodiment of an automated system for transferring fluid.

FIG. 1 schematically shows an embodiment of an automated fluid transfer system 100. The system 100 can include a housing 102 enclosing a controller 104 and a memory module 106. The system 100 can also include a user interface 108, which can be, for example, external to the housing 102. The user interface 108 can also be integrated into the housing 102 in some cases. The user interface 108 can include, for example, a display, a keypad, and/or a touch screen display. The user interface 108 can be configured to receive instructions from the user, for example, regarding the amounts of fluid to be transferred and the types of fluids to be transferred. The user interface can also be configured to provide information to the user, such as error messages, alerts, or instructions (e.g., to replace an empty vial). Although in the embodiment shown, the controller 104 and memory module 106 are contained within the housing 102, a variety of other configurations are possible. For example, controller 104 can be external to the housing 102, and can be, for example contained within a second housing, which may also contain the user interface 108. In some embodiments, the system 100 can include a communication interface 110 configured to receive information (e.g., instructions) from a remote source such as an external controller 112, a terminal (such as a computer) 114, or an automated management system (such as a hospital information system (HIS)) 116, etc. In some embodiments, the communication interface can also send information (e.g., results or alerts) to the remote source. The communication interface can include one or more connection types and can be configured to allow connectivity to multiple remote sources at once. In some embodiments, the system 100 does not include a communication interface 105 and does not communicate with a remote source.

The system 100 can include multiple transfer stations 118a-b. In the embodiment shown, the system 100 includes two transfer stations 118a-b, but a different number of transfer stations can be used. For example, in some embodiments, the system may include a single transfer station. In other embodiments, the system may include two, three, four, five, six, seven, eight, or more transfer stations depending on the number of different fluid types the system is designed to handle and the amount of fluid to be transferred.

Each transfer station 118a-b can include a fluid source container 120a-b, which can be, for example, a medical vial or other suitable container such as a bag, a bottle, or a vat, etc. Although many embodiments disclosed herein discuss using a vial as the source container, it will be understood the other containers can be used even when not specifically mentioned. In some embodiments, each of the source containers 120a-b can contain a unique fluid, providing a variety of fluids that the user can select for transfer. In other embodiments, two or more of the source containers 120a-b can contain the same fluid. In some embodiments, the source containers 120a-b include bar codes that identify the types of fluid contained therein. The bar codes can be scanned by a bar code scanner 105 that is in communication with the controller 104 and/or the memory 106 (e.g., via the communication interface 110) so that the identities of the fluids contained by source containers 120a-b can be stored within the memory module 106. In some embodiments, the fluid transfer stations 118a-b are configured to transfer precise amounts of fluid from source containers 120a-b to target containers 124a-b, which can be, for example IV bags. It will be understood that in various embodiments described herein, a different type of target connector or destination container can be used instead of an IV bag (e.g., a syringe, a bottle, a vial, an elastomeric pump, etc.) even when not specifically mentioned. In some embodiments the fluid can first be transferred from source containers 120a-b to intermediate measuring containers 122a-b so that a precise amount of fluid can be measured. The intermediate measuring containers 122a-b can be, for example, syringes. After being measured, the fluid can be transferred from intermediate measuring containers 122a-b to the target containers 124a-b.

The fluid transfer system 100 can be used to transfer individual fluids from the source containers 120a-b to separate target containers 124a-b, or to transfer and combine fluids from multiple source containers 120a-b into a common target container (e.g., 124a in FIG. 1). In the embodiment shown in FIG. 1, when combining fluids from both fluid source containers 120a-b into a common target container 124a, the other target container 124b can be omitted, and the fluid can be driven along the path shown by the dotted line from the connector 126b to the target container 124a. Thus, system 100 can be used for compounding mixtures of fluids. For example, the system 100 can be used to combine multiple medications together or to combine feeding fluids (e.g., water, dextrose, lipids, vitamins, minerals). The system 100 can also be used to dilute a medication or other fluid to a desired concentration level. Thus, in some embodiments, a first fluid transfer station 118a can include a concentrated medication or other fluid, and a second fluid transfer station 118b can include saline or other diluent. The system 100 can be configured to receive input (e.g., from a user or from a HIS) indicating a desired amount and concentration of medication, and the system 100 can be configured to transfer the precise amounts of the concentrated medication and the diluent required to fill the source container 124a with the desired amount and concentration of the medication.

In some embodiments, a single system can be configured both for compounding mixtures of fluids and for the transfer of individual fluids from a single-source container to a single-target container. For example, a system containing six fluid transfer stations can be configured so that transfer stations 1-3 are dedicated to compounding mixtures of fluids into a single common target container, while fluid transfer stations 4-6 can be configured to each transfer fluid from a single source container to a single target container. Other configurations are possible.

In some embodiments, one or more of the transfer stations 118a-b can include one or more pairs of male and female fluid connectors configured to be attached to each other to selectively permit the passage of fluid. The connectors can be detached or disconnected, for example, so that the target container 124a-b can be removed once the fluid has been transferred. In some embodiments, the connectors can be configured to automatically close when disconnected from a corresponding connector, thereby preventing fluid from escaping when the connectors are detached. Thus, the fluid transfer system 100 can be used to transfer fluid while retaining substantially entirely, or entirely, all of the fluid within the system, permitting the fluid transfer to occur in a substantially entirely, or entirely, closed system. The fluid transfer system 100 can thereby reduce or eliminate the risk of injury, waste, or damage caused by liquid or vapor leakage when connecting and disconnecting the components of the fluid transfer system 100.

In some embodiments, the system 100 can be configured to be compatible with a variety of sizes of syringes (e.g., 10 ml, 20 ml, 50 ml, and 100 ml). For example, larger volume syringes can be used to transfer larger volumes of fluid in shorter amounts of time. Smaller volume syringes can be used to increase the accuracy and precision with which amounts of fluid can be transferred. In some embodiments, the syringes can include a bar code which identifies the volume of the syringe. The bar code can be scanned by a bar code scanner 105, so that the sizes of the syringes used by the different transfer stations 118a-b can be stored within memory module 106 for use by the controller 104.

In some embodiments, connectors 126a-b connects the source containers 120a-b, the intermediate containers 122a-b, and the target containers 124a-b. In some embodiments, the connectors 126a-b can include first check valves (not shown) configured to allow fluid to flow from the source container 120a-b into the connector 126a-b, and block fluid from flowing from the connector 126a-b into the source container 120a-b, as shown by single-headed arrows. The connectors 126a-b can also include second check valves (not shown) configured to allow fluid to flow from the connector 126a-b into the target container 124a-b, but block fluid from flowing from target container 124a-b into connector 126a-b, as shown by single-headed arrows. In some embodiments, the connectors 126a-c can be in two-way fluid communication with the intermediate containers 122a-b, as shown by double-headed arrows.

In some embodiments, the system 100 can include mounting modules 128a-b for mounting the transfer stations 118a-b onto the housing 102. For example, in some embodiments the mounting modules 128a-b can be configured to receive intermediate measuring containers 122a-b, as shown in FIG. 1, to secure the transfer stations 118a-b onto the housing. The mounting modules 128a-b can also engage the connectors 126a-b or other portions of the fluid transfer stations 118a-b. For example, in some embodiments, the connectors 126a-b can include a ridge or channel that is configured to interface with a corresponding channel or ridge in the mounting modules 128a-b, to facilitate precise positioning of the fluid transfer stations with respect to the housing 102 and other components. The system 100 can also include motors 130a-b, which can be for example, contained within the housing 102. The motors 130a-b can be configured to actuate the intermediate measuring containers 122a-b to draw fluid into the containers (from the source containers 120a-b) and to dispel fluid therefrom (into the target containers 124a-b). The motors 130a-b can be in communication with the controller 104 and can receive actuation instructions from the controller 104. For example, the intermediate containers 122a-b can operate as precision syringe pumps to transfer precise amounts of fluid with the motors configured in some embodiments to actuate plungers on the syringes to draw fluid into the syringes. The motors 130a-b and automated system 100 allow for precise transfer of fluids at a faster and more consistent rate than using a syringe pump by hand. For example, a large syringe (e.g., 50 ml or 100 ml) can require significant effort to manipulate the plunger, which can be difficult to perform by hand, especially if done repeatedly. The motors 130a-b and automated system 100 can increate the precision, consistency, and rate of fluid transfer.

In some embodiments, the system can include fluid detectors 132a-b configured to detect a presence or absence of fluid in connectors 120a-c or at other locations in the fluid transfer stations 118a-b. The fluid detectors 132a-b can be in communication with the controller 104 so that when the detectors 132a-b detect an absence of fluid, which can indicate that source fluid containers 120a-b have run dry, the detectors 132a-b can send a signal to the controller 104 indicating that a source container 120a-b may need to be replaced. The fluid detectors 132a-b can be, for example, infrared LEDs and photo detectors, or other types of electronic eyes, as will be discussed in more detail below. In the embodiment shown, fluid detectors 132a-b are shown connected to connectors 126a-b, but other configurations are possible. For example, fluid detectors 132a-b can be connected to fluid source containers 120a-b themselves. In some embodiments, multiple fluid detectors can be used in the same general location of a single transfer station 118a-b. For example, a first sensor can be configured to detect a first type of fluid (e.g., alcohol-based fluids), and a second sensor can be configured to detect a second type of fluid (e.g., non-alcohol-based fluids).

In some embodiments, the system 100 can include compatibility modules 127a-b for preventing connectors other than approved connector 126a-b from being placed in communication with the system 100. By allowing only approved connectors 126a-b to be used with the system 100, the compatibility modules 127a-b can prevent inaccuracies in fluid transfers which may occur if an unapproved connector is used (e.g., which may have an internal volume different than approved connectors 126a-b). The compatibility modules 127a-b can be, for example, a specifically shaped mounting feature (e.g., on the mounting modules 128a-b) that is configured to interface with a corresponding portion of the connector 126a-b. The compatibility modules 127a-b can be one or more sensors configured to detect the presence of an approved connector 126a-b or to align with a specific portion of the connector 126a-b during operation.

In some embodiments, the system 100 can include source adapters 136a-b configured to receive the source containers 120a-b and removably connect to the connectors 126a-b. Thus, when a source container 120a-c runs out of fluid, the empty source container 120a-b and its corresponding adapter 136a-b can be removed and replaced without disengaging the associated connector 126a-b from the housing 102. In some embodiments, source adapters 136a-b can be omitted, and the source containers 120a-b can be directly received by the connectors 126a-b.

In some embodiments the system 100 can include sensors 134a-b for detecting the presence of target containers 124a-b. Sensors 134a-b can be in communication with the controller 104 so as to prevent the system 100 from attempting to transfer fluid when no target container 124a-b is connected. A variety of sensor types can be used for sensors 134a-b. For example, sensors 134a-b can be weight sensors, sensor pads, infrared sensors, or other forms of electronic eyes. In some embodiments, weight sensors 134a-b can also be used to measure the weight of the target containers 124a-b after fluid has been transferred. The final weight of a target container 124a-b can be compared to an expected weight by the controller 104 to confirm that the proper amount of fluid was transferred into the target container 124a-b. In some embodiments, the sensor 134a-b can align with a substantially transparent portion of the connector 126a-b to detect whether a valve on the connector 126a-b leading to target container 124a-b is open. If open, the sensor 134a-b can send a signal to the controller 104 so that fluid transfer is permitted. The sensors 134a-b can be configured to align properly with only approved connectors 126a-b so that the sensors 134a-b do not allow fluid transfer if an unapproved connector is used. Thus, the sensors 134a-b can be used as the compatibility modules 127a-b in some embodiments.

The fluid transfer system 100 can be modified in many ways. For example, as mentioned above, the system 100 can have a different number of transfer stations than the two shown in the illustrated embodiment. Also, in some embodiments, certain features shown in FIG. 1 can be omitted for some or all of the transfer stations. For example, in some embodiments, a fluid transfer station that is dedicated to the transfer of fluids that are not dangerous, expensive, or sensitive to ambient air (e.g., saline or water) can have fewer leak-preventing features than the fluid transfer stations dedicated to the transfer of fluids that are dangerous, expensive, or sensitive to ambient air. Thus, if fluid transfer station 118b were dedicated to the transfer of saline (e.g., to be used as a diluent), the sensor 134b could be omitted, in some cases. Without the sensor 134b, the system 100 could permit fluid to be expelled from the connector 126b when no target container 124a-b is attached, which could cause the fluid to leak. However, because saline is not a dangerous, expensive, or sensitive fluid, the possibility of leaking saline can be tolerated.

Figure 2:
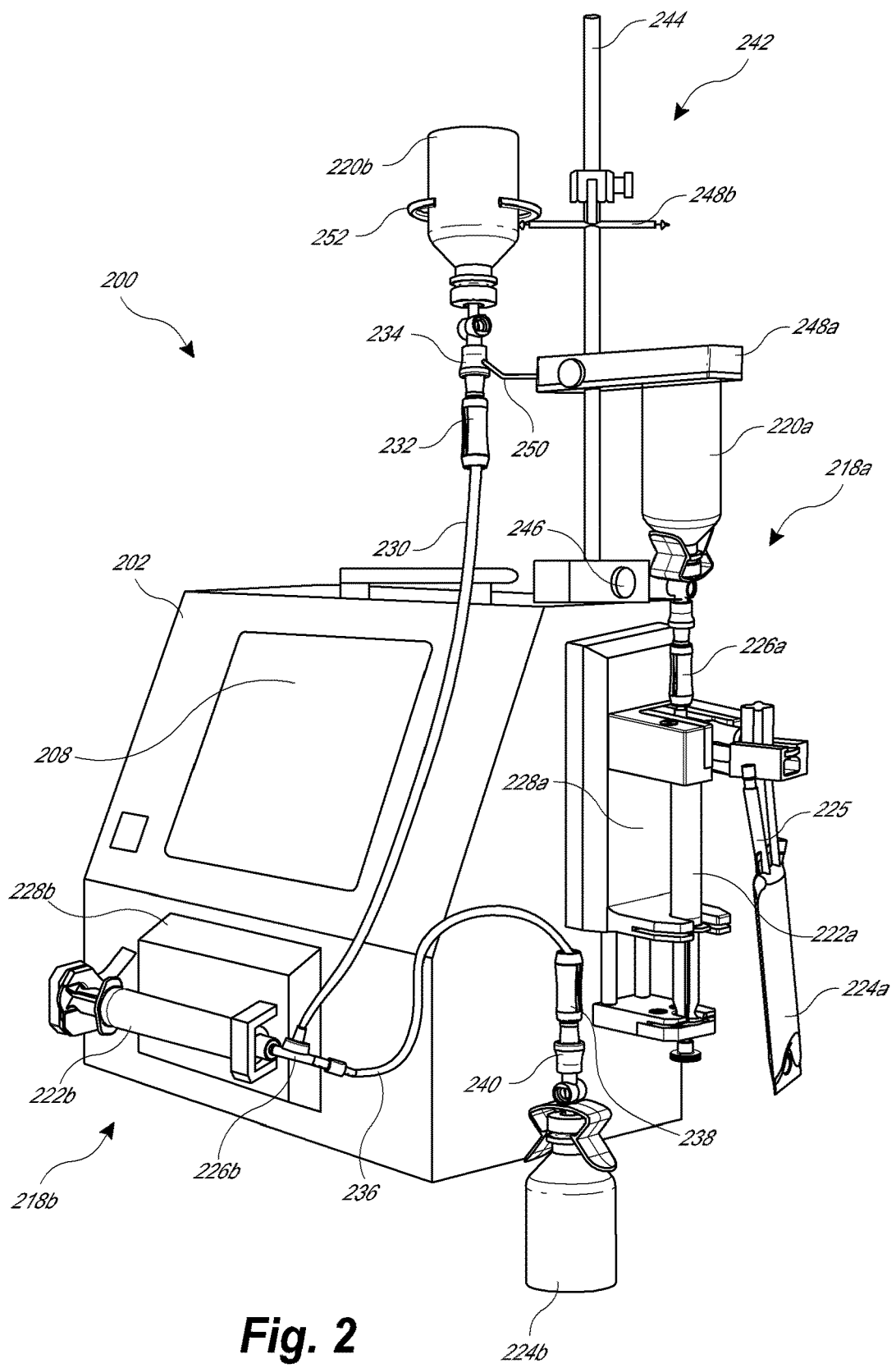
FIG. 2 is a perspective view of an example embodiment of an automated system for transferring fluid.
Figure 4:
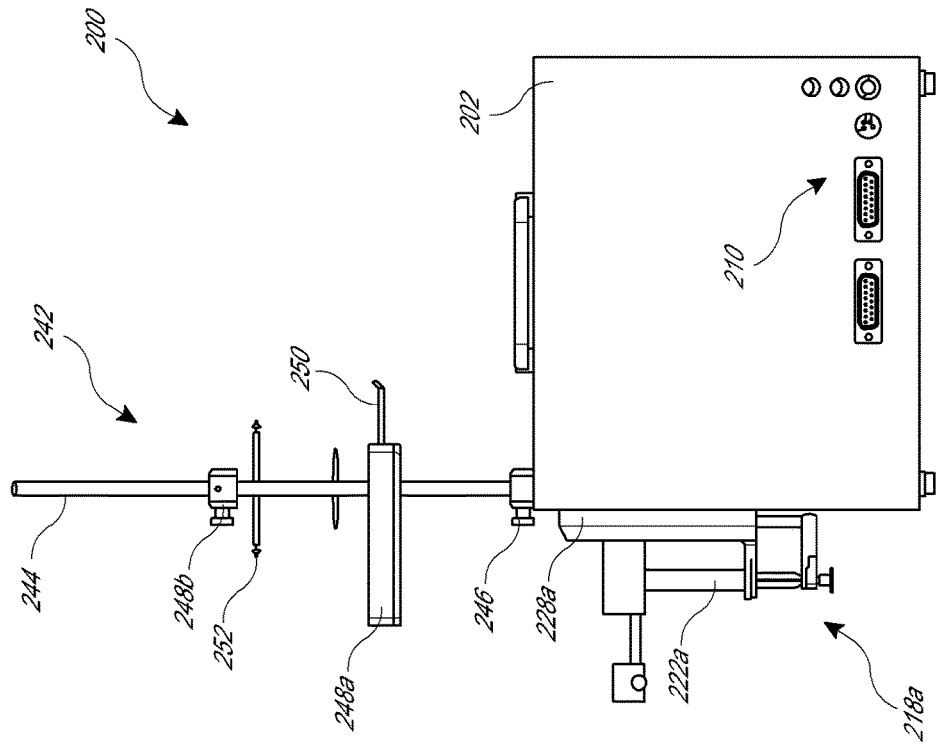
FIG. 4 is a back view of the system of FIG. 2.
Figure 3:
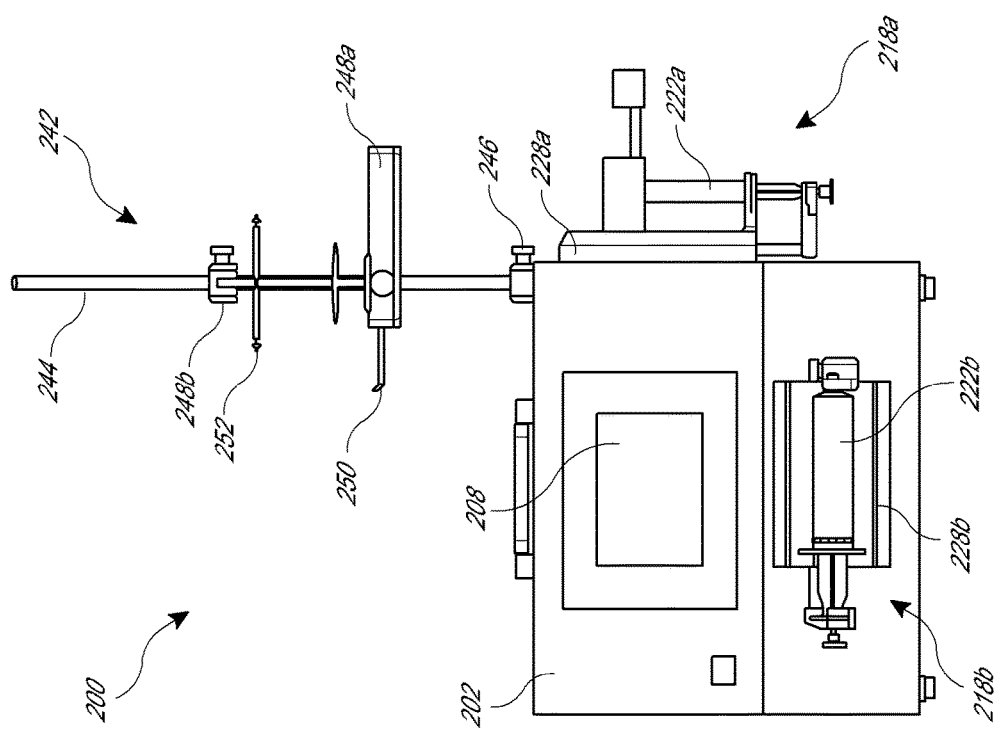
FIG. 3 is a front view of the system of FIG. 2.

FIG. 2 is a perspective view of an example embodiment of a fluid transfer system 200, which can have features similar to, or the same as, the system 100 described above or any other fluid transfer system described herein. FIG. 3 is a front view of the fluid transfer system 200 and FIG. 4 is a back view of the fluid transfer system 200. In FIGS. 3 and 4, certain features (e.g., the target and source containers and tubing) are omitted from view. The system 200 can include a housing 202, and a user interface 208 can be incorporated into the housing. The user interface 208 can include a touchscreen, a keypad, a display, or other suitable interface devices for providing information to a user and/or for providing input from the user to a controller (not shown).

As can be seen in FIG. 4, the system 100 can have a communication interface 210 which can include one or more connection points to receive cables from one or more remote sources such as a remote terminal (e.g., a computer) or an automated management system (e.g., a hospital information system (HIS)). The communication interface 210 can be configured to provide a communication link between the system 200 and a remote source. The communication link can be provided by a wireless signal (e.g., using an antenna) or by one or more cables or a combination thereof. The communication link can make use of a network such as a WAN, a LAN, or the internet. In some embodiments, the communication interface 210 can be configured to receive input (e.g., fluid transfer commands) from the remote source and/or can provide information (e.g., results or alerts) from the system to the remote source.

In the illustrated embodiment, the system 200 has two fluid transfer stations 218a-b. In some embodiments, the first transfer station 218a can be configured to provide a closed fluidics system suitable transferring dangerous, expensive, or sensitive fluids without, or substantially without, leakage or exposure to ambient air. In some embodiments, the second transfer station 218*b* can be configured differently than the first transfer station 218*a*. For example, the second transfer station 218*b* can be configured to transfer a fluid that is not dangerous, expensive, or sensitive (e.g., saline or water), which in some cases can be used as a diluent for diluting fluids transferred by the first transfer station 218*a*. Thus, in some cases the second fluid transfer station 218*b* can include fewer leak-prevention features than the first fluid transfer station 218*a*, as will be described herein, which can provide less complexity and reduced cost.

The first fluid transfer station 218*a* can be configured to transfer fluid from a vial 220*a*, through a connector 226*a*, and into a syringe 222*a* when the syringe plunger is retracted. When the syringe plunger is advanced, the fluid can be driven out of the syringe 222*a*, through the connector 226*a*, and into an IV bag 224*a*. The first fluid transfer station 218*a* can include a mounting module 228*a* configured to receive the syringe 222*a*, the connector 226*a*, the vial 220*a*, the IV bag 224*a*, or some combination thereof for mounting to the housing 202. The mounting module 228*a* can engage the syringe 222*a* so that a motor (e.g., a step motor) can precisely retract and advance the syringe plunger to transfer the fluid from the vial 220*a* to the IV bag 224*a*.

In the configuration shown in FIG. 2, the second fluid transfer station 218*b* is configured to transfer fluid from a second fluid source container 220*b* (e.g., a vial or fluid bag) to a second fluid target container 224*b* (e.g., a vial). In some embodiments, the second fluid transfer station can be used to transfer a reconstituting fluid or a diluent (e.g., saline or water). For example, in the configuration shown in FIG. 2, the fluid from vial 220*b* can be used to reconstitute a medication (e.g., in powdered form) contained in the vial 224*b*, or can be used to dilute a concentrated medication in the vial 224*b*. In some embodiments, the second fluid transfer station 218*b* can be used to transfer fluid to the same IV bag 224*a* used by the first fluid transfer station 218*a*, for example, to dilute the medication transferred into the IV bag 224*a* from the vial 220*a*. The second fluid transfer station 218*b* can include a syringe 222*b* which can be mounted onto the housing 202 by a mounting module 228*b* so that a motor can precisely retract and advance the plunger of the syringe 222*b* to transfer fluid. When the syringe plunger is retracted, fluid can be drawn from the vial 220*b*, through a connector 226*b*, and into the syringe 222*b*. When the syringe plunger is advanced, the fluid can be driven from the syringe 222*b*, through the connector 226*b*, and into the vial 224*b* (or into the IV bag 224*a*).

A tube 230 can extend from an inlet on the connector 226*b* toward the fluid source container 220*b*. A connector 232 (e.g., a Spiros® closeable male connector manufactured by ICU Medical, Inc., of San Clemente, Calif.) can be located at the end of the tube 230 and can be used to connect to a corresponding connector 234 (e.g., a Clave® connector manufactured by ICU Medical, Inc., of San Clemente, Calif.) that is attached to the fluid source container 220*b*. Additional details relating to Clave® connectors and some variations are disclosed in the '866 Patent. In various embodiments disclosed herein, other types of connectors can also be used, such as a MicroCLAVE® connector (manufactured by ICU Medical, Inc., of San Clemente, Calif.), or any other connector disclosed or described herein, including those in the '302 Application, including, for example, clear connectors. When the connectors 232 and 234 are engaged, a fluid connection exists between the fluid source container 220*b* and the connector 226*b*. A tube 236 can extend from an outlet of the connector 226*b* and a connector (e.g., a Spiros® closable male connector) can be positioned at the end of the tube 236. A corresponding connector 240 (e.g., a Clave® connector) can engage the connector 238 to provide a fluid connection between the connector 226*b* and the vial 224*b*. The IV bag 224*a* may have a supplemental line of tubing 225 that can be configured to engage the connector 238 to provide a fluid connection between the connector 226*b* and the IV bag 224*a*.

The system 200 can include a pole assembly 242, which can be configured to hold fluid containers such as vials and fluid bags. A pole 244 can extend upward from the housing 202, and in some embodiments, the pole 244 can be height adjustable and thumb screw 246 can be tightened to hold the pole 244 in place. The thumb screw 246 can be loosened to enable adjustment of the height of the pole 244, and in some embodiments, the pole 244 can be lowered into a recess formed in the housing 202 that is configured to receive the pole 244. Thus, the pole 244 can be entirely, substantially entirely, or mostly withdrawn into the housing 202 when the pole 244 is not in use (e.g., during storage or transportation or when not needed to support fluid containers). One or more support modules 248 can be attached to the pole 244 and can be configured to support fluid containers. The support modules 248 can include thumb screws so that the positions of the support modules 248 on the pole 244 can be adjustable, and/or so that the support modules 248 can be removable from the pole 244. In the illustrated embodiment, a first support module 248*a* can be used to support the vial 220*a*, and can have a hook 250 (e.g., for hanging a fluid bag). A second support module 248*b* can have one or more curved arms 252 for supporting a fluid container such as vial 220*b*.

Figure 6:
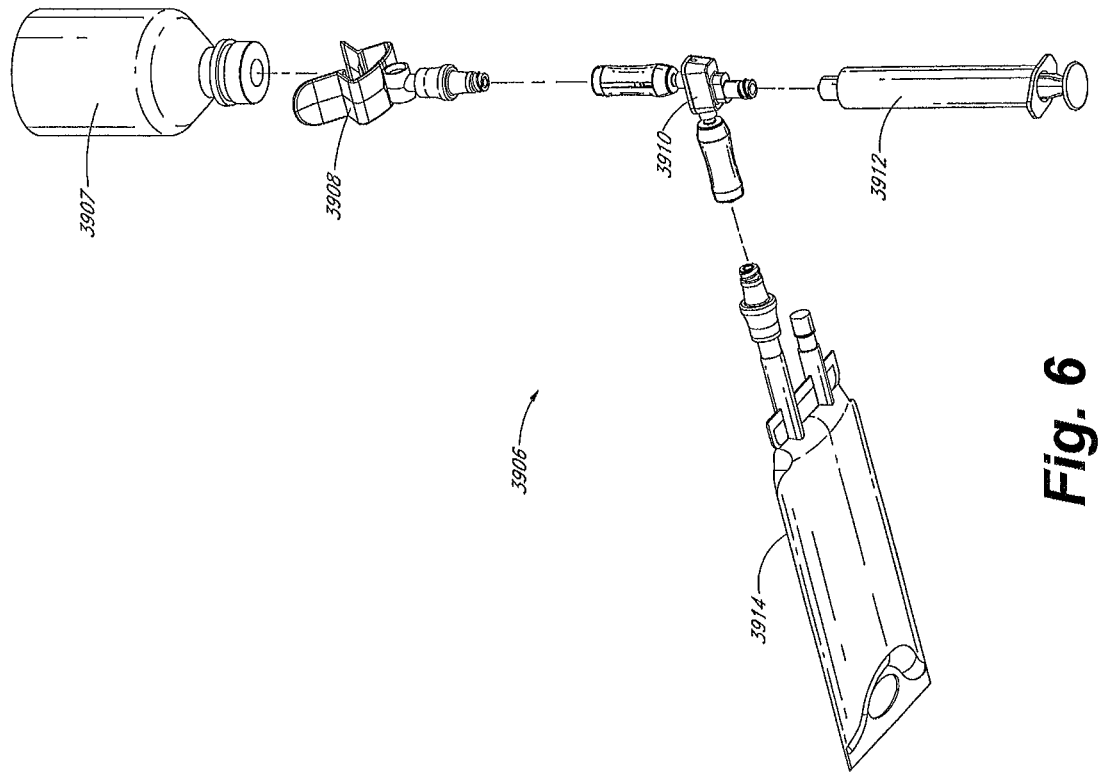
FIG. 6 is an exploded view of the fluidics assembly of FIG. 5.
Figure 5:
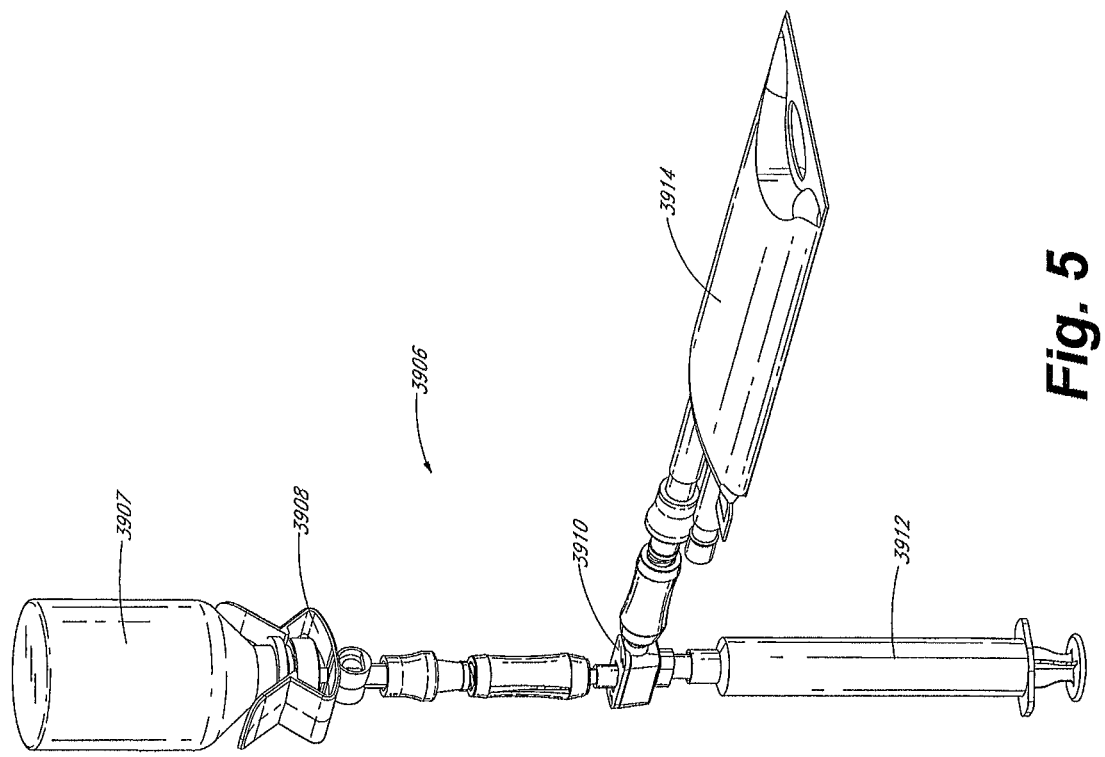
FIG. 5 is a perspective view of an example embodiment of a fluidics assembly that can be used to transfer fluid.

FIG. 5 is a perspective view of a fluidics assembly 3906 that can be used with the first fluid transfer station 218*a*. FIG. 6 is a perspective exploded view of the fluidics assembly 3906 from a different angle than that shown in FIG. 5. The fluid assembly 3906 can be used to transfer precise amounts of fluid from a vial 3907 to an IV bag 3914. The fluidics assembly 3906 includes a vial 3907, a vial adapter 3908 configured to provide fluid communication with the fluid (e.g., chemotherapy drug or other medication) contained within the vial 3907, a syringe 3912, an IV bag assembly 3914, and a connector 3910 for directing fluid from the vial adapter 3908 into the syringe 3912 and from the syringe 3912 toward the IV bag assembly 3914. In some embodiments, the fluidics assembly 3906 can have features similar to, or the same as, those of the other fluidics systems disclosed herein. For example, the connector 3910 can be the same or substantially similar to the connector 226*a*, also discussed herein. In some embodiments, the fluidics assembly 3906 can be configured to allow the vial 3907 and vial adapter 3908 to be replaced (e.g., when the vial runs out of fluid) without replacing the connector 3910 or syringe 3912. In some embodiments, the vial adapter 3908 can be configured to allow air to enter the vial 3907 via the vial adapter 3908, thereby substantially equalizing pressure in the vial 3907 as fluid is drawn out.

Figure 7:
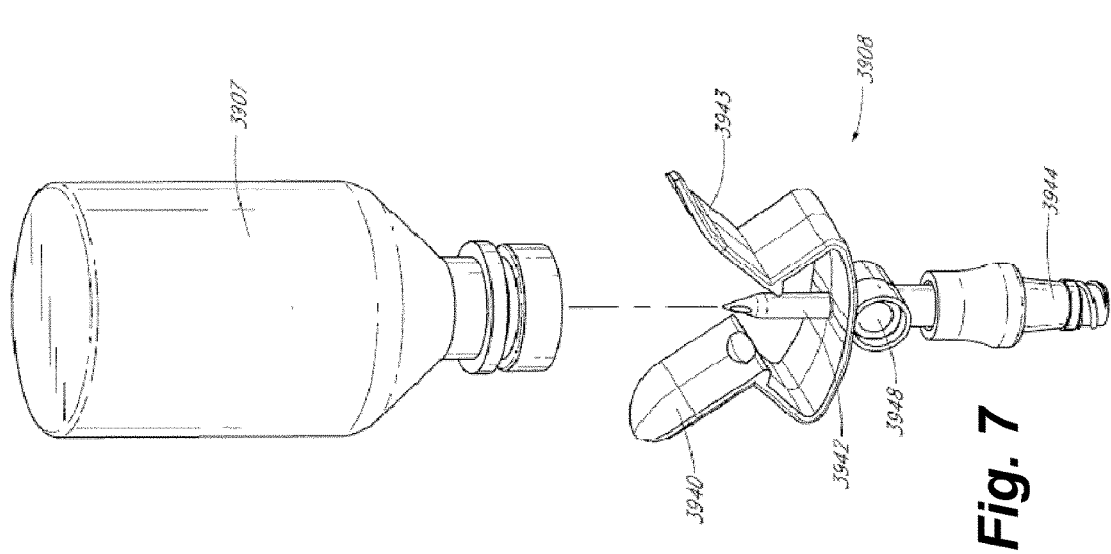
FIG. 7 shows an example embodiment of a vial and a vial adapter that can be used in the fluidics assembly of FIG. 5.

FIG. 7 a perspective view showing the vial adapter 3908 and the vial 3907 in a separated configuration, such as before the vial 3907 is attached to the vial adapter 3908. The upper portion 3940 of the vial adapter 3908 can include a spike 3942 configured to pierce the septum on the cap of the vial 3907 and arms 3940, 3943 configured to retain the vial 3907 onto the vial adapter 3908.

Opposite the upper portion 3940, the vial adapter can include a connector, which can be, for example, a female connector 3944. The connector 3944 can be, for example, a version of the Clave® connector manufactured by ICU Medical, Inc., of San Clemente, Calif. Various embodiments of a connector of this type are described in the '866 Patent. The female connector 3944 can seal the end of the vial adapter 3908 such that no fluid is allowed to escape from the vial adapter 3908 until a male connector is attached to the female connector 3944. It should be understood that in many embodiments discussed herein, the male and female connectors can be switched. For example, the vial adapter 3908 can include a male connector which is configured to mate with a female connector on the connector 3910.

The vial adapter 3908 can include an air intake channel 3946 configured to direct air into the vial 3907 to compensate for fluid removed from the vial 3907 to reduce the pressure differential. The air intake channel 3946 can include a filter 3948 configured to allow air to pass through the filter 3948 and toward the vial 3907 while also preventing fluid from passing through the filter. For example, the filter 3948 can include an air permeable but fluid impermeable membrane. The filter 3948 can be a hydrophobic filter. In some embodiments, the vial adapter 3908 can include a check valve in place of or in addition to the filter 3948. The check valve could be a duck bill valve, a slit valve, or a sliding ball valve, or any other suitable type of check valve. The vial adapter 3908 can also have a bag that is configured to increase in volume while preventing the input air to contact the fluid inside the vial 3907, similar to the embodiments described in the '157 Publication. Thus, the vial 3907 can be vented by a mechanism independent of the connector 3910.

Figure 8:
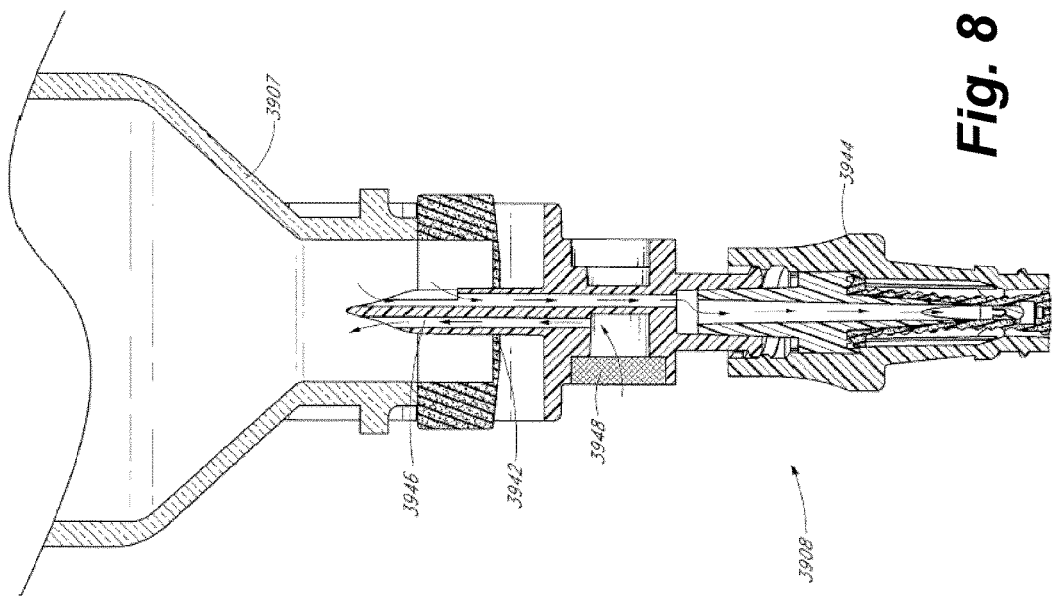
FIG. 8 is a cross sectional view of the vial and vial adapter of FIG. 7.

FIG. 8 is a cross sectional view of the vial 3907 and vial adapter 3908 in an assembled configuration. As shown by the flow lines in FIG. 8. Air can pass through the filter 3948, through the air inlet channel 3946, and into the vial 3907 to compensate for the fluid that is drawn out of the vial 3907 through a fluid channel 3950. The fluid channel 3950 can pass through the spike 3942, and down through the female connector 3944 as shown. Although the female connector 3944 is shown in a closed configuration in FIG. 8, it will be understood that the female connector 3944 can be opened by the first male connector 3964 of the connector 3910, as discussed below, to allow fluid to pass from the vial adapter 3908 to the connector 3910.

Figure 9:
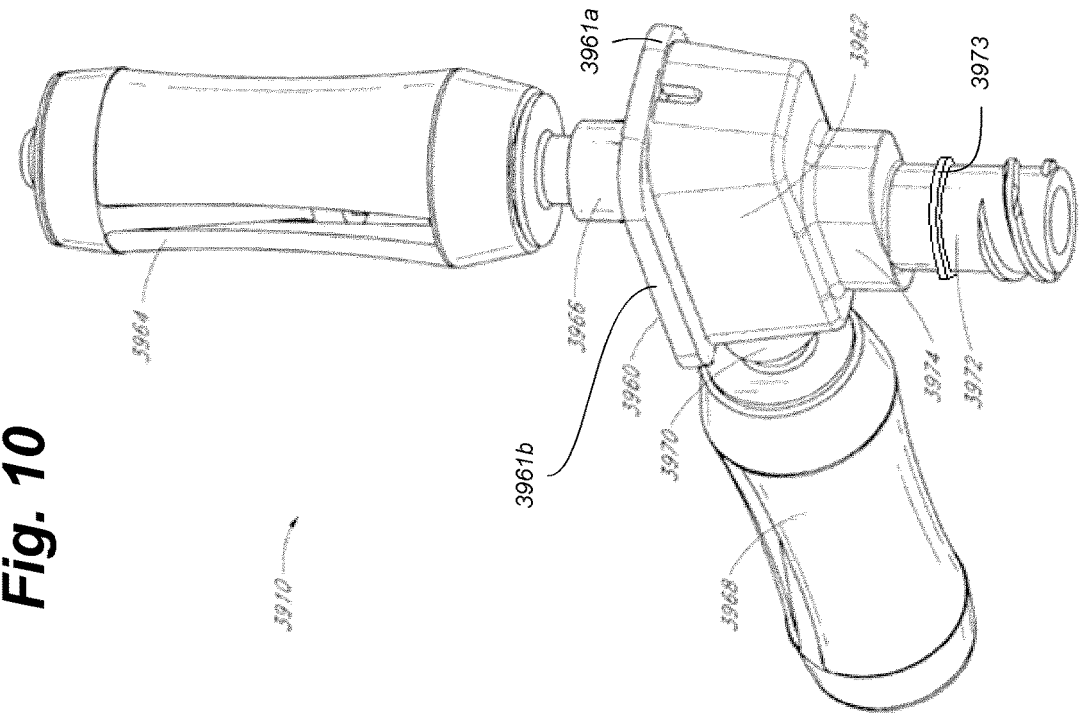
FIG. 9 is a perspective view of an example embodiment of a connector that can be used with the fluidics system of FIG. 5.
Figure 10:
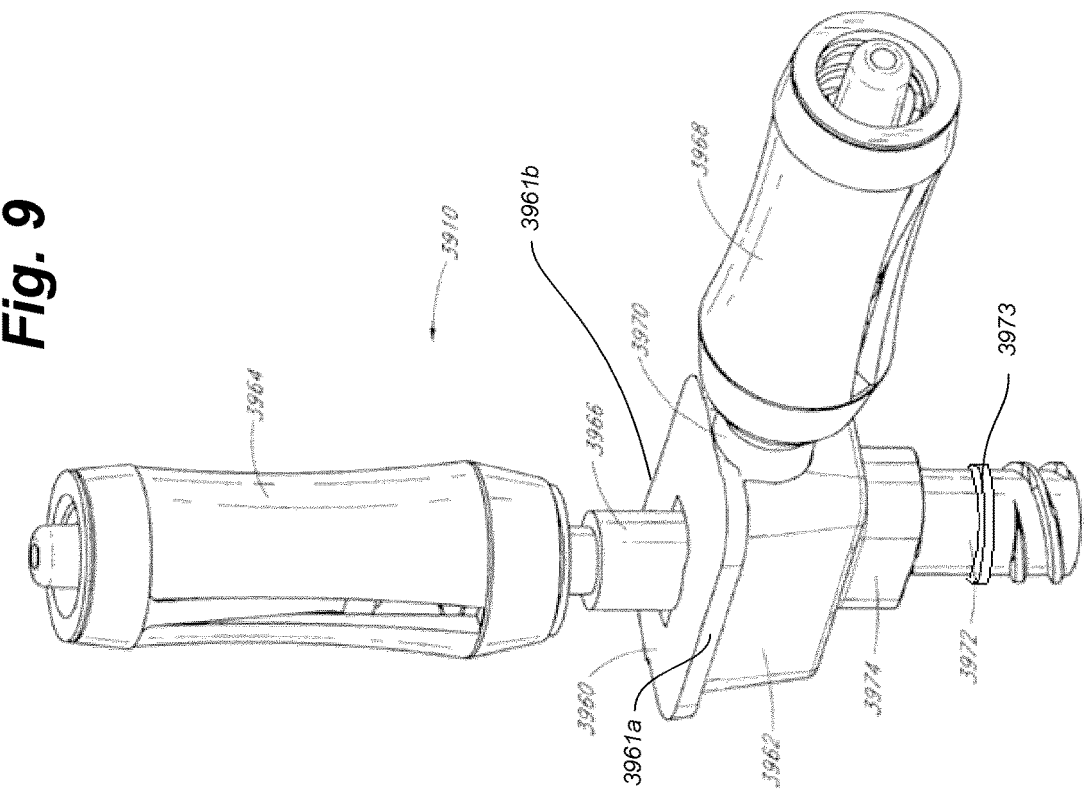
FIG. 10 is another perspective view of the connector of FIG. 9.

FIG. 9 is a perspective view of the connector 3910. FIG. 10 is a perspective view of the connector taken from a different angle than the view of FIG. 9. The connector 3910 can have features similar to, or the same as, those of the other connectors disclosed herein. The connector 3910 can include an upper housing portion 3960 and a lower housing portion 3962. A first male connector 3964 can be attached to a female end 3966 of the upper housing portion. A second male connector 3968 can be attached to a female end 3970 of the lower housing portions 3962. The male connectors 3964, 3968 can be a version of the Spiros® closeable male connector manufactured by ICU Medical, Inc., of San Clemente, Calif. Various embodiments of connectors of this type are described in the '920 Publication. In this embodiment, and in other embodiments described herein as including a male connector or a female connector, it can be possible for female connectors to be used in place of the described male connectors and for male connectors to be used in place of the described female connectors. For example, one or both of the connectors 3964 and 3968 can be female connectors (e.g., Clave® connectors manufactured by ICU Medical, Inc., of San Clemente, Calif.), and the connector 3944 of the Vial adapter 3908 can be a male connector (e.g., a Spiros® closeable male connector manufactured by ICU Medical, Inc., of San Clemente, Calif.).

A syringe interface 3972 can extend down from the bottom of the lower housing portion 3962 to receive the syringe 3912. A sensor region 3974 can also be positioned at the base of the lower housing portion 3962 and can be configured to allow light to pass through the fluid pathway in the connector 3910 to detect the presence of bubbles, which can indicate that the vial 3907 has run out of fluid. In some embodiments, the surface of the sensor region can be flat to allow light to pass through the wall of the sensor region 3974 at an angle that is perpendicular to the surface, thereby allowing the light to more reliably strike the corresponding sensor. In some embodiments, the sensor region can be at or near the interface between the first male connector 3964 and the upper housing portion 3960, so that the bubble sensor can more easily detect air before it reaches the syringe. For example, the female end 3966 of the upper housing portion 3960 can be longer than shown in FIGS. 9 and 10 and can be substantially transparent to light of the bubble sensor. In some embodiments, the walls of the female end 3966 can have generally flat sensor regions similar to 3974 discussed above.

Figure 14:
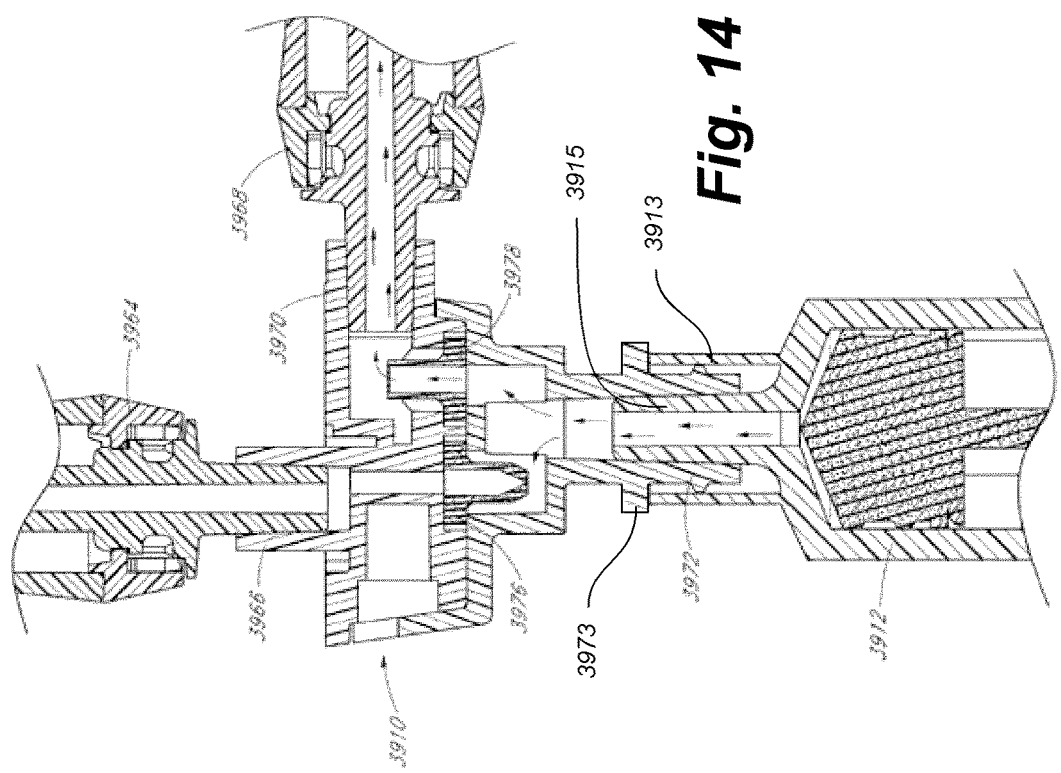
FIG. 14 is another cross sectional view of the connector of FIG. 9, showing a second fluid flow path through the connector.
Figure 13:
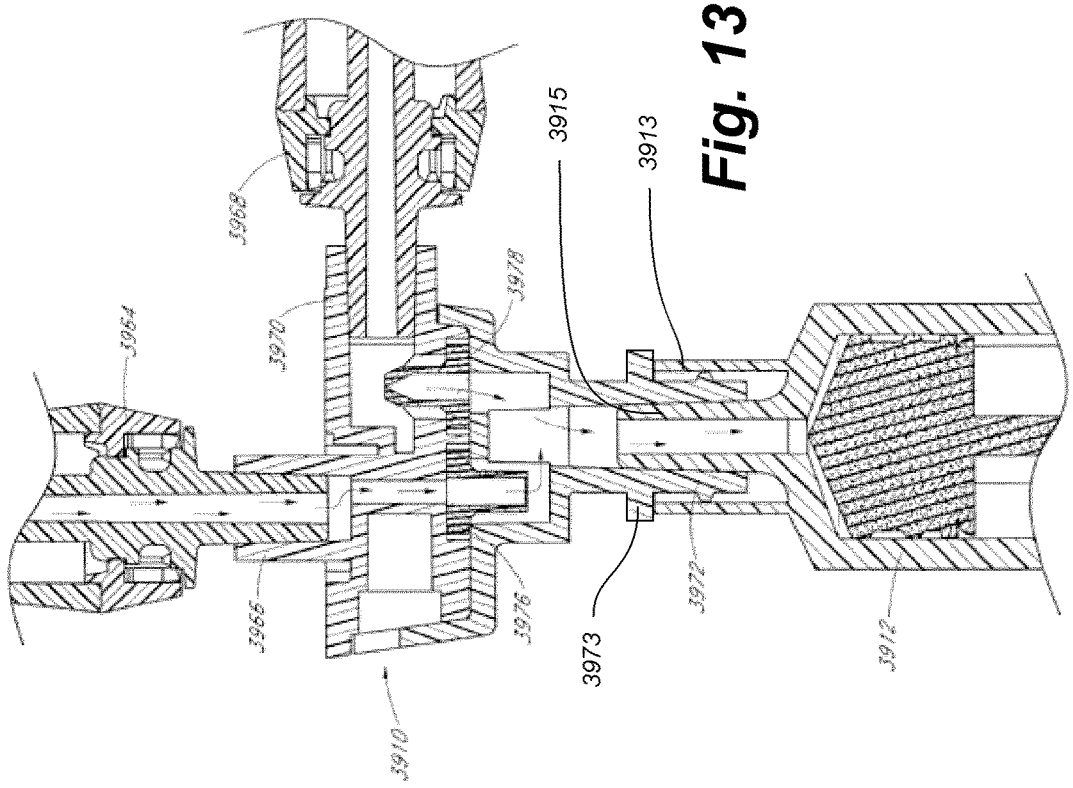
FIG. 13 is a cross sectional view of the connector of FIG. 9, showing a first fluid flow path through the connector.

In some embodiments, syringe interface 3972 can include a stop mechanism, such as a collar 3973, configured to control the position of the syringe 3912 relative to the connector 3910 when engaged. For example, as can be seen in FIGS. 13 and 14, the syringe 3912 can include a male luer tip 3915 and shroud 3913 surrounding the male luer tip 3915. When the syringe 3912 engages the syringe interface 3972 of the connector 3910, the shroud 3913 can abut against the collar 3973 once the syringe 3912 is engaged to a desired position. Thus, the collar 3973 can prevent the male luer tip 3915 from being over-inserted past the desired engagement position. Other stop mechanisms can be used. For example, the connector 3910 can include a ridge formed on the inside of the syringe interface 3972 so that the male luer tip 3915 of the syringe abuts against the ridge when the syringe 3912 has reached the desired engaged position.

The stop mechanism (e.g., collar 3973) can facilitate the alignment of the connector 3910, or other components, with one or more sensors (e.g., air sensors and/or sensors configured to detect whether an IV bag is attached to the connector 3910). For example, in some embodiments, the body of the syringe 3912 can engage with a mounting module 228 of the fluid transfer system 200 so that the syringe is secured to the system 200. The connector 3910 can be secured to the system 200 indirectly by the connector 3910 being engaged with the syringe 3912 via the syringe interface 3972. Thus, if the syringe 3912 were over inserted past the desired engagement position, the connector 3910 may be positioned lower than desired, which can interfere with the proper operation of the sensors. For example, an air sensor may be aligned with an incorrect portion of the connector 3910 causing the sensor to provide inaccurate readings. In some embodiments, the connector 3910 can engage directly with the mounting module 228 (e.g., using the protrusions 3961a-b inserted into corresponding grooves in the mounting module 228), and the stop mechanism can facilitate accurate transfer of fluid. For example, if the syringe 3912 were over-inserted past the desired position, an amount of extra fluid may be drawn into the syringe 3912 when the plunger is drawn back, thereby compromising the accuracy of the fluid transfer, especially for fluid transfers that involve a volume that require multiple syringe fills. Also, because the internal volume of the fluidics system may be less than the expected internal volume by a small amount if the syringe is over-inserted, priming of the fluidics may result in pushing fluid into an IV bag prematurely.

In some embodiments, the connector 3910 can have features that are configured to secure the connector to a mounting module. For example, the connector 3910 can have one or more protrusions 3961a-b that are configured to fit into corresponding slots in the mounting module. The connector 3910 may have slots configured to receive protrusions on the mounting module. Many variations are possible. In the illustrated embodiment, the top housing portion 3960 has two extensions 3961a-b that extend past the sides of the bottom housing portion 3962 when attached, thereby forming two protrusions. The protrusions may also, or alternatively, be formed on the lower housing portion 3962. When attached to a fluid transfer station (e.g., 218a of FIG. 2), the protrusions 3961a-b of the connector 3910 can slide into corresponding slots to ensure that the connector 3910 is positioned at a location where one or more sensors can align with corresponding portions of the connector 3910 (or align with components attached to the connector 3910), as described herein. Also, the slots or protrusions or other features on the mounting module can be configured to interface only with connectors having corresponding features (e.g., protrusions 3961a-b) to verify that the connector 3910 is compatible or approved for use with the system. This can prevent a user from using a connector with insufficient leak-prevention features or a connector with a different internal volume (which can interfere with the precision of the transfer of fluid).

Figure 12:
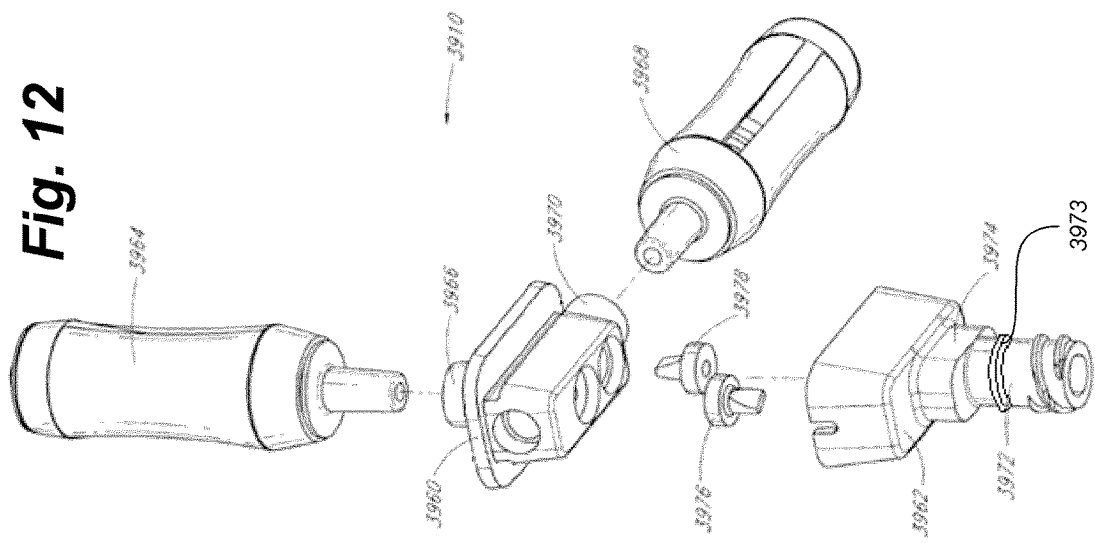
FIG. 12 is another exploded view of the connector of FIG. 9.
Figure 11:
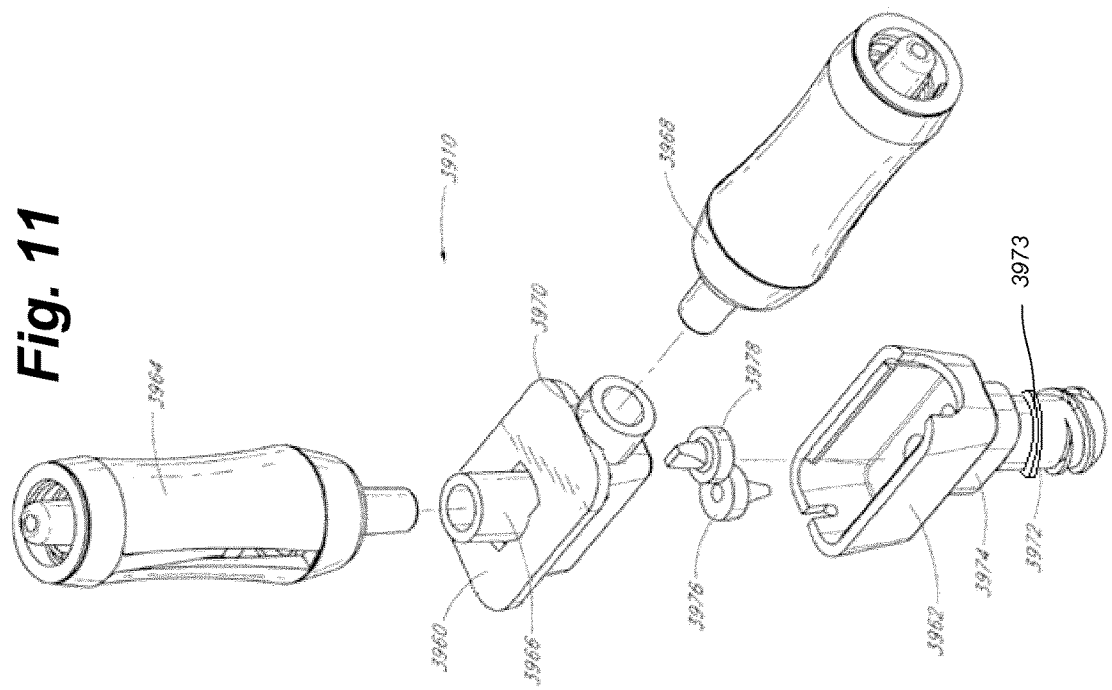
FIG. 11 is an exploded view of the connector of FIG. 9.

FIG. 11 is an exploded perspective view of the connector 3910. FIG. 12 is an exploded perspective view of the connector 3910 taken from a different view than FIG. 11. The first male connector 3964 can be configured to engage the connector 3944 of the vial adapter 3908. Thus, when the vial 3907 runs out of fluid, the vial 3907 and vial adapter 3908 can be replaced without replacing the connector 3910, syringe 3912, or any other part of the fluidics assembly 3906. This can provide the benefit of reducing the amount of disposable pieces and fluid sent to waste during a vial replacement.

When the vial 3907, vial adapter 3908, connector 3910, syringe 3912, and IV bag assembly 3914 are connected, a source fluid pathway can be formed between the vial 3907 and the syringe 3912, and a target fluid pathway can be formed between the syringe 3912 and the IV bag. A source check valve 3976 can be positioned in the source fluid pathway (e.g., inside the connector 3910) to allow fluid to flow from the vial 3907 into the syringe and prevent fluid from flowing back into the vial 3907. A target check valve 3978 can be positioned in the target fluid pathway (e.g., inside the connector 3910) to allow fluid to flow from the syringe 3912 to the IV bag and prevent fluid from flowing from the IV bag back toward the syringe 3912. The source and target check valves 3976, 3978 can be duck bill check valves, although dome check valves, disc check valves, or any other suitable check valve can be used. In some embodiments, the source and target check valves 3976, 3978 can be integrated into a single valve structure such as a flap movable between a source flow position in which fluid may flow through the source fluid path into the syringe 3912 and a target flow position in which fluid may flow through the target fluid path from the syringe 3912.

FIG. 13 is a cross sectional view of the connector 3910 and syringe 3912 showing fluid flowing through the connector 3910 from the vial 3907 to the syringe 3912. As the plunger of the syringe 3912 is withdrawn, fluid is drawn into the syringe 3912. The pressure causes the source check valve 3976 to open so that fluid is allowed to flow from the vial 3907 to the syringe 3912. The pressure also causes the sides of the target check valve 3978 to bear against each other to maintain the target check valve 3978 closed. Thus, fluid drawn into the syringe 3912 will be drawn from the vial 3907 and not the IV bag. As fluid is drawn out of the vial 3907, air can enter the vial 3907 through the air inlet channel 3946 as described above in connection with FIG. 8.

FIG. 14 is a cross sectional view of the connector 3910 and syringe 3912 showing fluid flowing through the connector 3910 from the syringe 3912 toward the IV bag assembly 3914. As the plunger of the syringe 3912 is advanced, fluid is driven out of the syringe 3912. The pressure causes the target check valve 3978 to open so that fluid is allowed to flow from the syringe 3912 toward the IV bag assembly 3914. The pressure also causes the sides of the source check valve 3976 to bear against each other to maintain the source check valve 3976 closed. Thus, fluid driven out the syringe 3912 will be directed to the IV bag and not back into the vial 3907.

FIG. 15 is a perspective view of the IV bag assembly 3914. The IV bag assembly 3914 can include an IV bag 3980, a length of tubing 3982, and a female connector 3984. The female connector 3984 can be removably or irremovably attached to the tubing 3982. The female connector 3984 can function to seal off the IV bag assembly 3914 so that no fluid can escape from the IV bag 3980 except when a male connector is attached thereto. In some embodiments, the IV bag assembly 3914 can include a supplemental line of tubing 3925 to also provide access to the IV bag 3980. The supplemental line 3925 can be used to transfer a second fluid (which can be different than the fluid transferred through the main line 3982) into the IV bag 3980. For example, the tubing 3984 can be used to transfer a concentrated fluid (e.g., medication) into the IV bag 3980, and the supplemental tubing 3925 can be used to transfer a diluent (e.g., saline or water) into the IV bag 3980 for diluting the concentrated fluid to a desired level of concentration. In some embodiments, the supplemental line of tubing 3925 can have a cap or a connector (not shown), which can be similar to the connector 3984, to enable a fluid line to be removably attached to the supplemental line 3925. In some embodiments, multiple fluid lines can combine (e.g., at a Y- or T-connection) so that multiple fluids (e.g., from different fluid transfer stations) can be directed into the IV bag 3980 through a single fluid line (e.g., tubing 3982). In some embodiments, the connector 3984 can be directly coupled with the bag 3980 without a significant length of tubing 3982 therebetween.

FIG. 16 is an alternative IV bag assembly 5700 which may be used with the fluidics assembly 3906 or with various other embodiments discussed herein. The IV bag assembly 5700 can include an IV bag 5702 and a length of tubing attached thereto 5704. A spike port 5706 can be positioned at the end of the tubing 5704, and the spike port 5706 can include a piercing membrane or barrier that when closed prevents fluid from entering or exiting the IV bag 5702. The female connector 5708 can have a spike 5710 attached thereto. The spike 5710 can be inserted into the spike port 5706 until it pierces the membrane or barrier thereby providing access to the interior of the IV bag 5702. In some embodiments, the part 5706 is directly coupled with the bag 5702 without a significant length of tubing 5704 therebetween.

Figure 18:
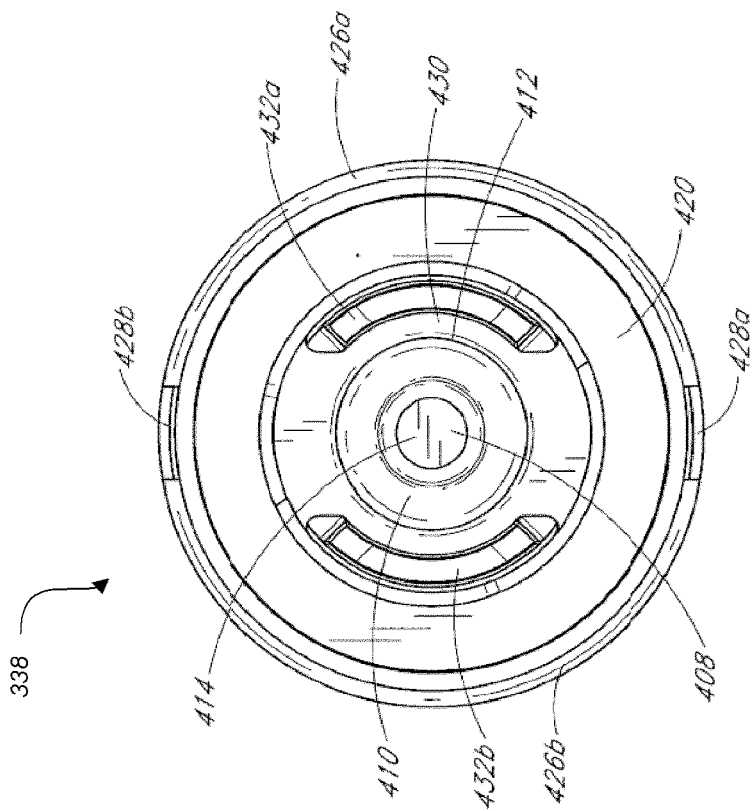
FIG. 18 is a front view of the male connector portion of FIG. 17.
Figure 17:
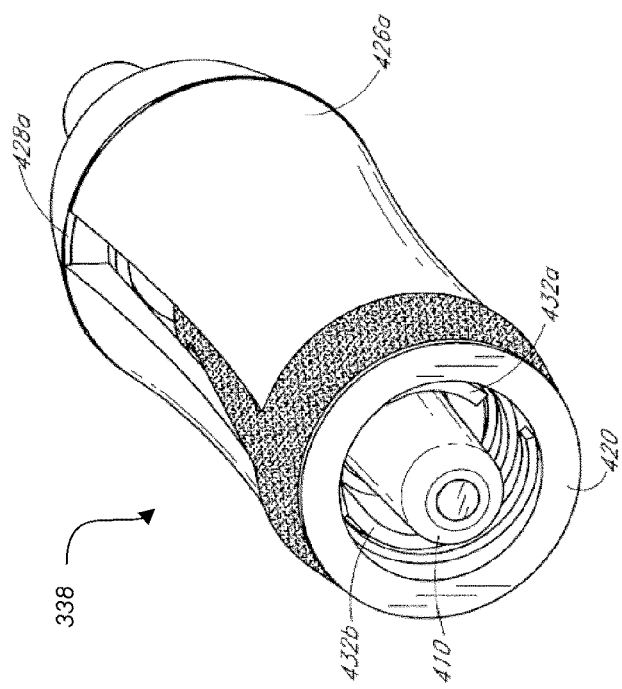
FIG. 17 is a perspective view of an example embodiment of a male connector portion that can be used for the connector of FIG. 9.

FIG. 17 shows a perspective view of a connector 338 which can be used as the source connector portion 3964 and/or the target connector portion 3968 of the connector 3910. FIG. 18 shows a top view of a housing portion of the connector 338. FIG. 19 is an exploded perspective view of the connector 338. FIG. 20 shows a cross-sectional view of the connector 338 and a female connector 332 in an unengaged configuration. FIG. 21 shows a cross-sectional view of the connector 338 and the female connector 332 in an engaged configuration. Although the connector 338 is shown separated from the remainder of the connector 3910 in FIGS. 17-21, it should be understood that the connector 338 can be connected to the remainder of the connector 3910 when in use.

With reference now to FIGS. 17-21, the connector 338 can be a closeable male luer connector that is configured to prevent fluid from escaping from or entering into the connector when it is not engaged with a corresponding female connector, but allow fluid to flow when it is engaged with a corresponding female connector 332. In the embodiments shown, the connector 338 can be a version of the Spiros® closeable male connector manufactured by ICU Medical, Inc., of San Clemente, Calif. In some embodiments, a substantially entirely or entirely closed system can be achieved, at least in part, by providing corresponding automatically closeable male and female connectors at various (or all) connection points within the fluid transfer system 200, thereby causing the stationary fluid to substantially entirely remain within the fluid source, the fluid module, and the fluid target, respectively, upon disconnection and to not generally leak or vaporize outside of the system. For example, in some embodiments, corresponding pairs of automatically closing connectors (e.g., male and female connectors) can be provided at the interfaces between the fluid source and the connector 3910, the connector 3910 and the intermediate container, and/or the connector and the target container.

The closable male connector 338 can include a housing 398, a valve member 400, a resilient member 402, a sealing ring 404, an end cap 406, and an O-ring 407. The housing 398 can be generally tubular in shape, and can include a passageway 408 that extends axially through the housing 398. As illustrated, the passageway 408 includes apertures on each side of the connector. The housing 398 can include a male luer tip 410 that connects to the rest of the housing 398 at a base 412. The luer tip 410 can be generally tubular in shape so that a portion of the passageway 408 is defined therein, and the luer tip 410 can include a hole 414 at its end providing access to the passageway 408. In some embodiments, the luer tip 410 includes a shelf 416 that extends radially inwardly toward the axis of the passageway 408. The shelf 416 can be located adjacent to the hole 414, so that the passageway 408 is narrowed at the end of the luer tip 410. In some embodiments, the surface of the shelf 416 that faces radially inwardly is tapered so that the passageway 408 is narrowest immediately adjacent to the hole 414. In some circumstances, the shelf 416 can be configured to seal the passageway when a portion of the valve member 400 is abutted against it. As illustrated, in some embodiments, connectors can be used to substantially entirely prevent fluid therein to leak or otherwise escape through apertures in the fluid pathway when the connectors are closed.

The luer tip 410 can be surrounded by a shroud 418. In some embodiments, the luer tip 410 extends some distance beyond the edge 420 of the shroud. The shroud 418 can include inner threads 422 on its interior surface. The inner threads 422 can be used for securing a female connector 332. The shroud can include an indented portion 424 that has a smaller outer diameter than the other portions of the housing. The indented portion 424 can be configured to engage a portion of the resilient member 402.

The housing 398 can include two wall sections 426a, 426b separated by two gaps 428a, 428b. The gaps 428a, 428b can be configured to receive portions of the resilient member 402. The wall sections 426a, 426b can be configured to engage the end cap 406.

In some embodiments, the housing 398 includes a middle portion 430 located substantially between the wall sections 426a, 426b, and connected to the wall sections 426a, 426b near the gaps 428a, 428b. In some embodiments, holes 432a, 432b are defined between the middle portion 430 and the wall sections 426a, 426b (as shown in FIG. 18). In some embodiments, the luer tip 410 connects to the middle portion 430 at its base 412. In some embodiments, the middle portion 430 defines a portion of the passageway 408 therein. In some embodiments, portions 434 of the outer surface of the middle portion 430 are exposed by the gaps 428a, 428b. The portions 434 can include notches 436a, 436b and through-holes 438a, 438b. The notches 436a, 436b can be generally rectangular in shape, and can be tapered such that the notches 436a, 436b are narrower near their bases than near their surfaces. The through-holes 438a, 438b can also be generally rectangular in shape.

The housing 398 can be constructed from a variety of materials. The housing 398 can be constructed from a rigid material such as polycarbonate or other polymeric materials. In some embodiments, the housing 398 can be constructed from a hydrophobic material such as Bayer Makrolon, or any other suitable material. In some embodiments, the housing 398 can be formed from a substantially transparent material.

The valve member 400 can include a fluid passageway 440 extending axially from an opening formed in a base portion 444 and into a tube 446. In some embodiments, the passageway 440 can be wider in the base portion 444 than in the tube 446. In some embodiments, the tube 446 includes a narrowed tip 448. In some embodiments, the tip 448 can have a tapered outer surface. The tip 448 can be tapered to substantially the same degree as the radially inwardly facing surface of the shelf 416 and can be sized so that the tip 448 can form a fluid seal with the shelf 416 when abutted against it. In some embodiments, the tip 448 can be made from a flexible or compressible material, such as silicone rubber to facilitate formation of the fluid seal between the tip 448 and the shelf 416. In some embodiments, the tube can include one or more holes 450 for providing access to the fluid passageway 440. The holes 450 can be formed, for example, in the tip 448 of the tube 446.

In some embodiments, the valve member 400 can include two struts 452a, 452b extending out from the base 444 and positioned on either side of tube 446, so that an open space is defined on either side of the tube. In some embodiments, the tube 446 can extend axially past the ends of the struts 452a, 452b.

The base 444 of the valve member 400 can include a plurality of protrusions 454 extending radially outwardly from its external surface. In some embodiments, the protrusions 454 can be positioned so as to define two channels 456a, 456b therebetween. In some embodiments, the protrusions 454 do not extend across the full length of the base 444, leaving a lower portion 458 of the base 444 that has a substantially smooth outer surface.

The valve member 400 can be constructed from a variety of materials, such as polycarbonate or other polymeric materials. In some embodiments, the valve member 400 can be constructed from the same material as the housing 398. In some embodiments, the valve member 400 and housing 398 can be constructed from different materials. In some embodiments, the valve member 400 can be constructed from multiple materials or from multiple pieces. For example, the tip 448 can be constructed from a material that is more flexible than the remainder of the valve member 400. In some embodiments, the valve member 400 can be formed from a substantially opaque material.

The resilient member 402 can include a first ring 460 and a second ring 462 connected to each other by elastic members 464a, 464b. The elastic members 464a, 464b can be made from an elastic material that exerts a restoring force when stretched, such as silicon rubber. Thus, if the rings 460, 462 are pulled apart, the elastic members 464a, 464b function to restore the rings 460, 462 to their relaxed configuration. In some embodiments, the rings 460, 462 are also constructed from an elastic material, such as the same material used to form the elastic members 464a, 464b. In some embodiments, the second ring 462 can have a greater diameter than the first ring 460. In some embodiments, the second ring 462 can have a tapered outer surface so that the end of the second ring 462 that is closest to the first ring 460 is wider than the end of the second ring 462 that is furthest from the first ring 460.

The sealing ring 404 can be generally cylindrical in shape, and can have a bore 466 extending axially therethrough. The sealing ring 404 can have a cylindrical body section 468 and an O-ring 470 located at one end of the body section 468. In some embodiments, the thickest portion of the O-ring 470 can be thicker than the body section 468 so that the thickest portion of the O-ring 470 extends radially inwardly toward the axis of the bore 466 a distance past the inner surface of the body section 468. Thus, the bore 466 can be narrower at the thickest part of the O-ring 470 than in the body section 468. In some embodiments, the thickest portion of the O-ring 470 also extends radially outwardly a distance past the outer surface of the body section 468. The sealing ring 404 can include two protrusions 472a, 472b that extend radially outwardly from the body section 468. In some embodiments, the protrusions 472a, 472b can be generally rectangular in shape.

The sealing ring 404 can be constructed from a variety of materials. In some embodiments, the sealing ring 404 can be constructed from a deformable or elastic material such as a silicone rubber. In some embodiments, the sealing ring 404 can be constructed from the same material used for form the resilient member 402. In some embodiments, the sealing ring 404 can be constructed from a material capable of forming a fluid seal against a rigid plastic or other rigid polymeric material.

The end cap 406 can include a first end cap member 405 and a second end cap member 409. The second end cap member 409 can include a connector (e.g., a male connector 352), a plunger 474, and a disk portion 476 located between the male connector 352 and the plunger 474. The second end cap member 409 can have a fluid passageway 478 axially positioned therein. In some embodiments, the plunger 474 can be generally tubular in shape. In some embodiments, the outer surface of the plunger 474 includes an indented region 480, which can be configured to receive the O-ring 407 therein. The O-ring 407 can be constructed from an elastic material such as silicone rubber so that it can be stretched over the edge 482 of the plunger 474 and be seated in the indented region 480. In some embodiments, the O-ring 407 can be constructed from the same material as the resilient member 402 and/or the sealing ring 404. In some embodiments, the O-ring 407 can be sized so that when seated in the indented region 480, the thickest portion of the O-ring 407 extends radially outwardly a distance past the outer surface of the plunger 474.

In some embodiments, the passageway 478 can have a substantially constant width throughout the second end cap member 409. In some embodiments, the passageway 478 can be tapered so that it is wider in the male connector 352 than in the plunger 474. In some embodiments, the passageway 478 can narrow near the end of the plunger 474, for example, to accommodate the indented region 480.

The first end cap member 405 can be generally frusto-conical in shape and can have a central opening 471 therein. When assembled, the plunger 474 can extend through the central opening 471. A ridge 473 can extend inward into the central opening 471. The ridge 473 can be received into a channel 475 on the second end cap member 409, which can, for example, be formed between the base of the plunger 474 and the disk portion 476 on the second end cap member 409, to secure the first end cap member 405 to the second end cap member 409. The ridge 473 and corresponding channel 475 can allow the first end cap member 405 to rotate about a longitudinal axis with respect to the second end cap member 409. Thus, the first end cap member 405 and the second end cap member 409 can join to form the end cap 406.

The valve end cap 406 can be constructed from a variety of materials, such as polycarbonate or other rigid polymeric materials. In some embodiments, the end cap 406 can be constructed from the same material as the housing 398 and/or the valve member 400. In some embodiments, the end cap 406 can be constructed from a different material than the valve member 400 and/or the housing 398. The first end cap member 405 can be formed from the same material as the second end cap member 409, or different materials can be used. In some embodiments, the first end cap member 405 or the second end cap member 409 or both can be substantially transparent.

Certain interconnections between various parts of the male connector 338 will now be discussed in further detail. The sealing ring 404 can be positioned inside the middle portion 430 of the housing 398. The protrusions 472a, 472b can be sized and positioned so that they engage the through-holes 438a, 438b. Thus, the sealing ring 404 can be secured to the housing 398 so that it does not rotate or move axially with respect to the tube 446.

The valve member 400 can be slidably inserted into the housing 398 so that the tube 446 enters the passageway 408. The narrowed tip 448 of the tube 446 can pass through the bore 466 of the sealing ring 404 and into the male luer tip 410 until it abuts against the shelf 416. The tube 446 can have a width that substantially fills the bore 446 and presses against the O-ring 470 portion of the sealing ring 404 to form a fluid seal therebetween. The struts 452a, 452b can pass through the holes 432a, 432b in the housing 398 respectively, so that the struts 452a, 452b are positioned between the male luer tip 410 and the shroud 418.

The resilient member 402 can function to bias the valve member 400 against the housing 398. The first ring 460 can fit onto the lower portion 458 of the base 444 of the valve member 400, so that a surface of the ring 460 abuts against the protrusions 454. The second ring 462 can fit into the indented portion 424 of the housing. The elastic members 464a, 464b can be positioned in the channels 456a, 456b respectively, and can pass through the respective gaps 428a, 428b between the wall sections 426a, 426b of the housing 398.

The O-ring 407 can be seated onto the indented region 480 of the end cap 406, as discussed above, and the plunger 474 can be slidably inserted at least partially into the passageway 440 of the valve member. In some embodiments, the thickest portion of the O-ring 407 can be wider than the portion of the passageway 440 formed in the base 444 of the valve member 400, so that the O-ring 407 forms a fluid seal against the inner surface of the passageway 440. The plunger 474 can be inserted into the valve member 400 until the disk portion 476 of the end cap 406 comes into contact with the ends of the wall sections 426a, 426b of the housing 398.

In some embodiments, the wall sections 426a, 426b can be secured to the top surface 477 of the first end cap member 405 by sonic welding, snap fit structures (not shown), a pressure or friction fitting, or other suitable connection type. As mentioned above, the first end cap member 405 can be secured to the second end cap member 409 in a manner that allows the first end cap member 405 to rotate relative to the second end cap member 409. Thus, once the connector 338 is assembled, the housing 398, sealing ring 404, resilient member 402, valve member 400, and/or first end cap member 405 can rotate relative to the second end cap member 409 about the longitudinal axis. Many variations are possible. For example, in some embodiments, the connector 338 can include a frangible element (not shown) that is configured to prevent the housing 398 and/or other components from rotating relative to the second end cap member 409 until a sufficient force is applied to break the frangible element. Once the frangible element is broken, such as by rotating the housing 398 or other component of the connector 338 with sufficient force, the housing 398 and/or other components can be permitted to rotate relative to the second end cap member 409, as described in the '920 Publication. In some embodiments, no frangible element is included, and the housing 398 and/or other components of the connector 338 can be rotatable relative to the second end cap member 409 once the connector 338 is assembled.

With reference now to FIGS. 20-21, the connector 338 can be configured to engage a female connector 332. A variety of types of female connectors 332 can be used. The female connector 332 shown is a closable female luer connector that includes a housing 490, a spike 492, a base 494, and a resilient seal element 496. A fluid passageway 498 can pass through the base 494 and through the spike 492. The spike 492 can include one or more holes 500 providing fluid communication between the passageway 498 and the area outside the spike 492. The seal element 496 can be shaped and positioned to substantially surround the spike 492. The seal element 496 can include a closable aperture 502 or slit that can open to allow the tip of the spike 492 to pass through then end of the seal element 496 when the seal element 496 is compressed (as shown in FIG. 21). The housing can include external threads 504 configured to engage the inner threads 422 on the housing 398 of the connector 338. An end of the tubing 334 can be connected to the end of the female connector 332 by an adhesive, clamp, friction or pressure fitting, or other suitable manner to form a fluid tight connection.

As discussed above, in some embodiments, the housing 398, sealing ring 404, resilient member 402, valve member 400, and/or first end cap member 405 can rotate about the longitudinal axis with respect to the second end cap member 409. Thus, as the female connector 332 of the IV bag assembly is attached to the connector 338, the female connector 332 can be held still while the housing 398 of the connector 338 can rotate causing the threads 504, 422 to engage. Because the female connector 322 is not required to rotate during engagement and disengagement with the connector 338, the tubing 334 can avoid being twisted or kinked and the user is not required to twist the IV Bag to accommodate rotation of the female connector 322. Some additional embodiments of the connectors with this rotational capability are disclosed in the '920 Publication.

When not engaged with the female connector 332 (as shown in FIG. 20), the connector 338 can be sealed. In some embodiments, fluid can enter the connector 338 at the male connector 352 and pass through the passageway 478 of the end cap 406, through the passageway 440 of the valve member 400, through the holes 450, and into the portion of the passageway 408 defined by the male luer tip 410. But the fluid seal created by the tip 448 of the valve member 400 pressing against the shelf 416 of the male luer tip 410 prevents the fluid from exiting the connector 338. In some embodiments, an increase in pressure, such as when additional fluid is forced into the connector 338, causes the tip 448 to press more firmly against the shelf 416, thereby improving the fluid seal.

When the connector 338 is engaged with the female connector 332 (as shown in FIG. 21), the external threads 504 of the female luer connector 332 can engage the inner threads 422 on the shroud 418, securing the female connector 332 to the male connector 338. The edge of the male luer tip 410 can press against and compress the resilient seal element 496 so that the spike 492 passes through the aperture 502 until the holes 500 are exposed. The end of the housing 490 of the female luer connector 332 can enter the space between the male luer tip 410 and the shroud 418 until it contacts the struts 452a, 452b. As the female luer connector 332 further engages the connector 338, it can push on the struts 452a, 452b causing the entire valve member 400 to retract. As the valve member 400 retracts, the elastic members 464a, 464b of the resilient member 402 stretch. When the valve member 400 retracts, the tip 448 disengages from the shelf 416, breaking the fluid seal and allowing fluid pass from the passageway 408 in the housing 398 of the connector 338 to the passageway 498 in the female connector 332 via the holes 500. When engaged, the resilient seal element 496 exerts a restoring force toward the connector 338 that presses the end of the seal element 496 against the end of the male luer tip 410, forming a fluid seal therebetween. Thus, the fluid can be kept isolated from the external environment while it is transferred from the male connector 338 to the female connector 332.

The female connector 332 can be disengaged from the male connector 338. The restoring force exerted by the resilient seal element 496 of the female connector 332 causes it to return to its closed position, sealing off its passageway 498. The elastic members 464a, 464b of the resilient member 402 exert a restoring force on the valve member 400, causing the valve member 400 to return to its closed position with its tip 448 abutted against the shelf 416 as the female connector 332 is disengaged.

The '920 Publication discloses additional details and various alternatives that can be applied to the connector portion 338 of the connector 320.

Figure 22:
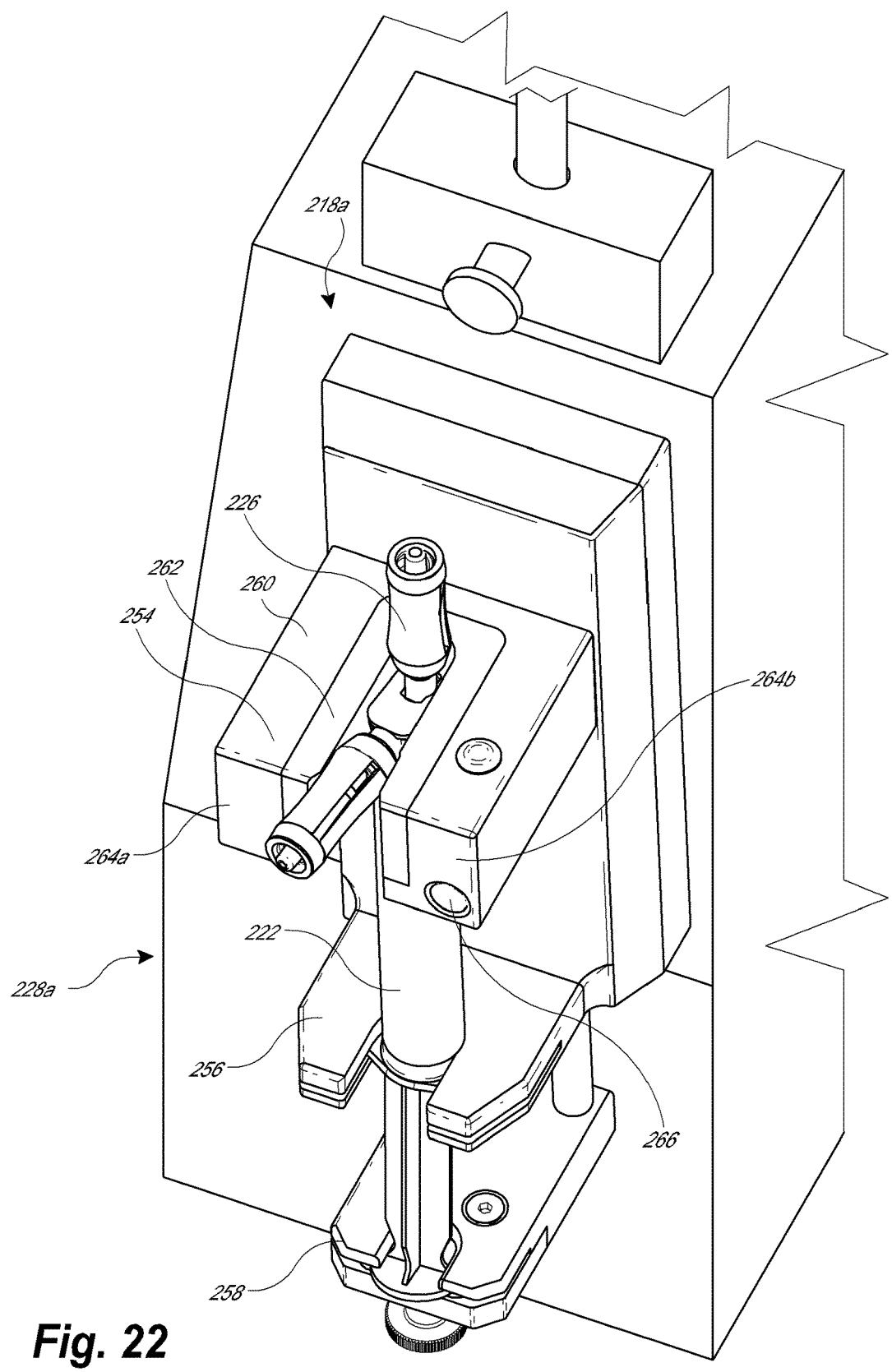
FIG. 22 shows an example embodiment of a transfer station having a connector and syringe attached thereto by a mounting module.

FIG. 22 illustrates the transfer station 218a with a connector 226 and a syringe 222 secured thereto by the mounting module 228a. The mounting module 228a can include an upper mounting portion 254 and a lower mounting portion 256. In the illustrated embodiment, the upper mounting portion 254 can be configured to receive the connector 226 and/or an upper portion of the syringe 222, and/or the lower mounting portion 256 can be configured to receive a lower portion of the syringe 222, such as a flange of the syringe body. An actuator 258 can engage the plunger of the syringe 222 (e.g., by a plunger flange), and the actuator 258 can be driven by a motor (e.g., step motor) so that the actuator 258 moves with respect to the lower mounting portion 256. By moving the actuator 258 downwardly, away from the lower mounting portion 256, the plunger can be withdrawn to draw fluid into the syringe 222. By moving the actuator 258 upwardly, towards the lower mounting portion 256, the plunger can drive the fluid out of the syringe 222.

The upper mounting portion 254 can be similar to, or the same as, the upper mounting portions described in the '703 Publication. The upper mounting portion 254 can include a base member 260 and a cassette 262, which can be removable from the base member 260 in some embodiments. The base member 260 can be coupled to the housing 202 and can have holes or channels to allow wires to pass from the housing 202 through the base member 260 to the cassette 262. The wires can provide electricity for sensors and can carry signals to and from the sensors as described herein. The base member 260 can include two arms 264a-b that form a recess therebetween to receive the cassette 262. One of the arms 264b can have a hole 266 which can be configured to receive a shaft for supporting an IV bag or other container as discussed herein. The '703 describes many details and variations that can be applied to the upper mounting portion 254 or to the other features of the mounting module 228a.

Figure 23:
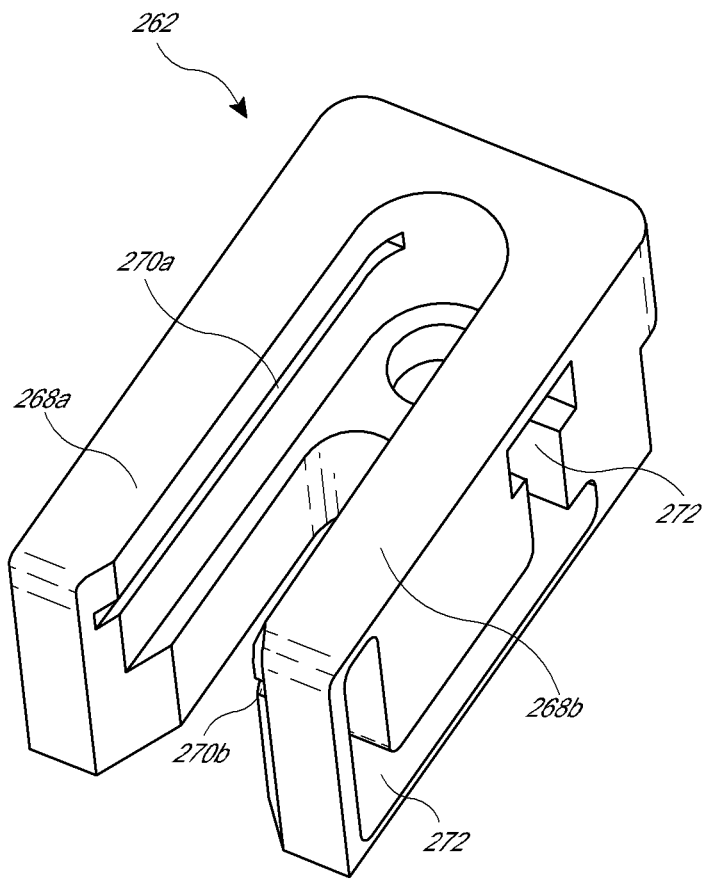
FIG. 23 shows an example embodiment of a cassette that an be used with the mounting module of FIG. 22.

FIG. 23 is a perspective view of the cassette 262. The cassette 262 can include two arms 268a-b forming a recess therebetween that can be configured to receive the connector 226. In some embodiments, the cassette 262 can include one or more features that are configured to engage with corresponding features on the connector 226a. For example, one or both of the arms 268a-b can have grooves 270a-b configured to receive the projections 3961a-b of the connector 226 as the connector 226a slides into the recess between the arms 268a-b. The engagement between the connector 226a (e.g., projections 3961a-b) and the cassette 262 (e.g., the grooves 270a-b) can secure the connector 226a relative to the cassette 262 at a location that aligns one or more sensors on the cassette 262 with portions of the connector 226a configured to interface with or be compatible with the sensors. The interface between the grooves 270a-b and the projections 3961a-b can also prevent the connector 226a from rocking or shifting in position during use.

Channels 272 can be formed in the cassette 262 to provide pathways for wires to connect to sensors. The cassette 262 can include one or more sensors configured to detect air in the fluid pathway from the source container (e.g., vial 220) into the connector 226a. In some embodiments, the one or more air sensors can detect whether air is present in the sensor path by using light, e.g., by measuring the amount of light that is transmitted, absorbed, scattered, or otherwise affected by the material that the light propagates through. In some cases, multiple sensors can be combined to use different wavelengths of light, e.g., for use with different types of fluid.

Figure 24:
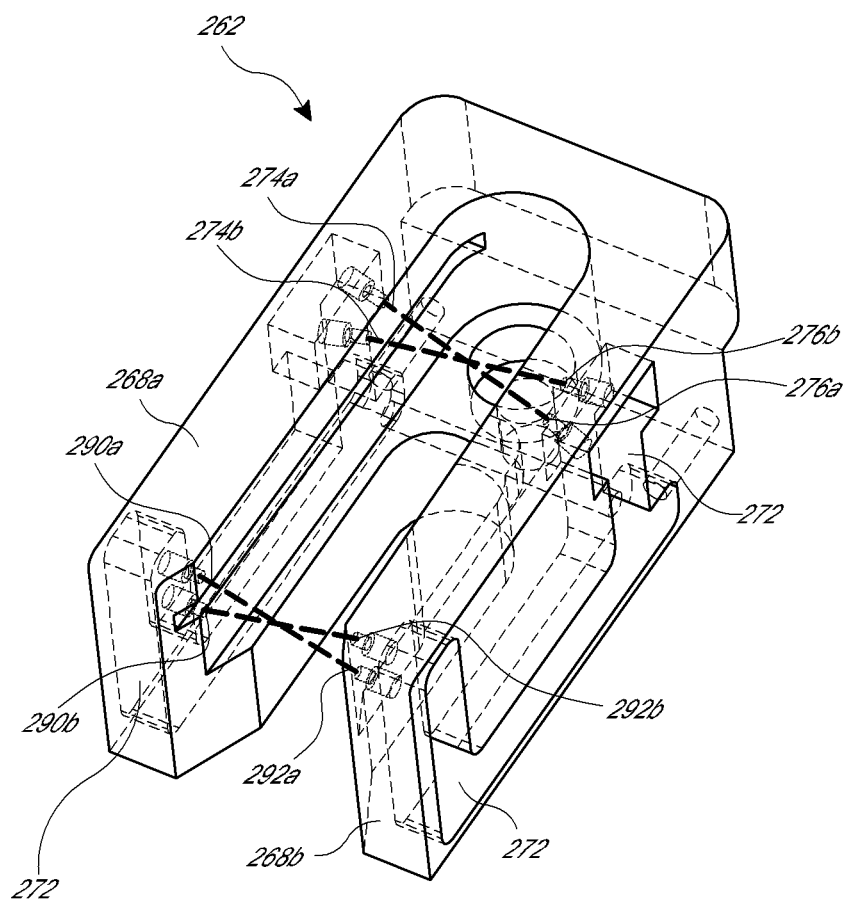
FIG. 24 is a partially transparent view of the cassette of FIG. 23.

FIG. 24 is a semi-transparent view of an example embodiment of a cassette 262 with sensors incorporated therein. In the embodiment of FIG. 24, the cassette 262 can include a first light source 274a of a first type and a second light source 274b of a second type. The cassette 262 can also include a first light detector 276a configured to detect light of the first type and a second light detector 276b configured to detect light of the second type. In some embodiments, the first light source 274a and the first light detector 276a can be configured to use visible red light to detect air (e.g., bubbles) in alcoholic fluids. The light used by the light source 274a and detector 276a can have a wavelength of at least about 620 nm and/or less than or equal to about 750 nm, or of at least about 640 nm and/or less than or equal to about 650 nm, or of about 645 nm, although other colors of light, and even non-visible light, can be used. The light used by the light source 274b and the detector 276b can use infrared light (e.g., near-infrared, short-wavelength infrared, or infrared-B) to detect air (e.g., bubbles) in non-alcoholic fluids. The light used by the second light source 274b and the second detector 276b can use infrared light having a wavelength of at least about 1250 nm and or less or equal to about 1650 nm, or of at least about 1400 nm and/or less than or equal to about 1500 nm, or of about 1450 nm, although light of other wavelengths may also be used.

Figure 25:
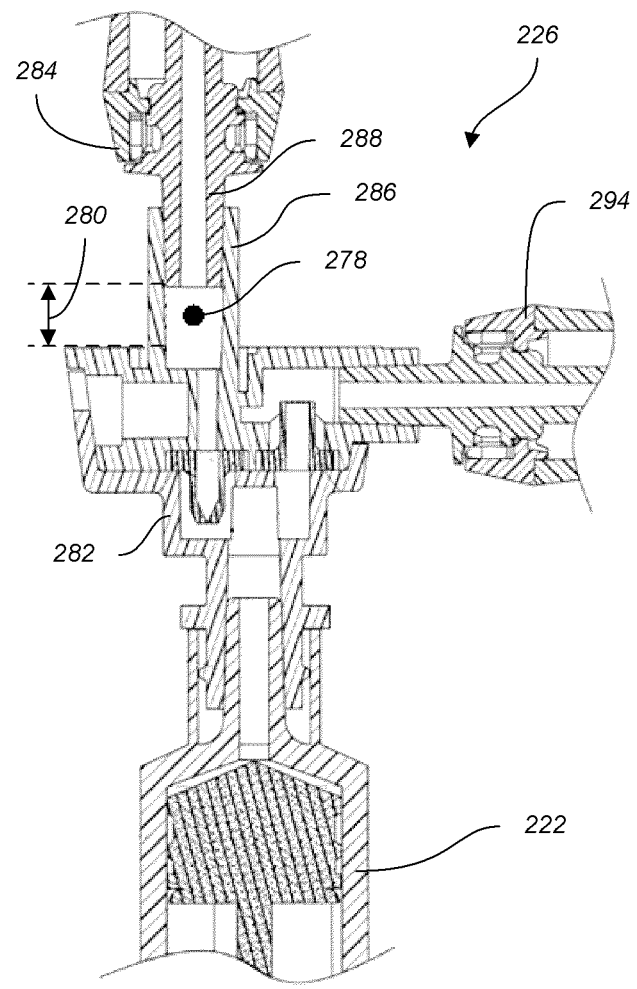
FIG. 25 is a cross sectional view of the connector of FIG. 22.

In the illustrated embodiment, the air sensors can be configured so that the light paths for the two air sensors 274a-b, 276a-b cross or overlap. In some embodiments, the light paths do not cross and can be substantially parallel to each other. FIG. 25 is a cross sectional view of the connector 226a showing the location 278 where the light passes through the connector 226a for air detection. The location 278 can be where the light paths cross. In some embodiments, the light can pass through the interface between the connector body 282 and the source connector portion 284 that leads to the fluid source vial (not shown). For example, the light can pass through a source connector projection 286 (e.g., a female fitting) that extends from the connector body 282 to receive a connection portion 288 (e.g., a male fitting) of the source connector 284. The light can pass through an area 280 between the tip of the connection portion 288 of the source connector 284 and the connector body 282, so that the light does not pass through the connection portion 288 of the source connector 284. Many alternatives are possible. For example, one or more of the light paths can pass through the connection portion 288 of the source connector 284 instead of the source projection 286. Thus, the source projection 286 can be shorter than shown in FIG. 25 and the connection portion 288 of the source connector 284 can be longer than shown in FIG. 25, so that the area 280 corresponds to the portion of the connection portion 288 that is positioned above the source projection 286. Alternatively, the one or more of the light paths can pass through both the source projection 286 and the connector portion 288 of the source connector 284. Also, the locations of the light sources 274a-b and the detectors 276a-b can be interchanged. Also, the sensors may be positioned so that the light passes through a different portion of the connector 226a, such as the area of the connector body 282 that is above the syringe 222.

Figure 26:
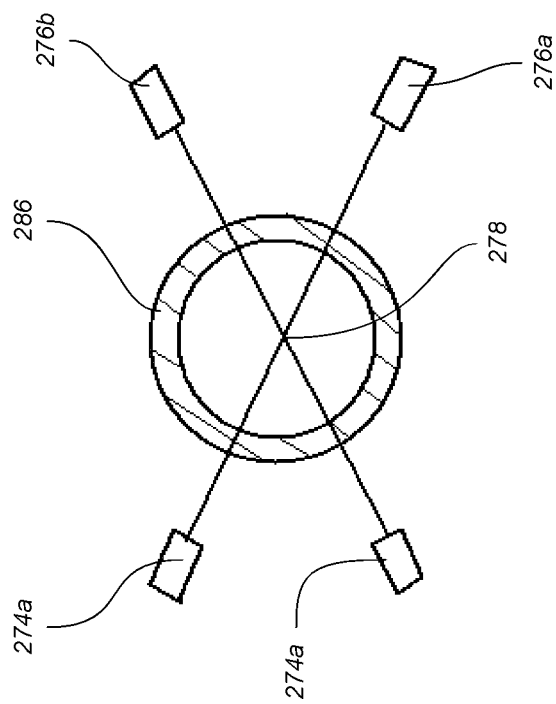
FIG. 26 is a cross sectional view of the connector of FIG. 22 taken through a sensor beam intersection plane.

The source projection 286 can be curved (e.g., having a circular cross sectional shape) and the crossing light paths can allow each path of light to intersect the walls of the curved source connector projection 286 at an angle that is normal or substantially normal (e.g., plus or minus 20°, 10°, 5°, 2°, or 1°) to the surfaces of the walls, as can be seen, for example, in FIG. 26, which can reduce the amount of light that is reflected or otherwise lost as the light propagates through the walls of the source connector projection 286. The two light paths can be positioned at substantially the same vertical position so that an air bubble traveling towards the connector 226a contacts both light paths substantially simultaneously. Thus, the system can treat air bubble detection the same in some ways regardless of which of the detectors 276a-b identified the air bubble. If one detector 276a-b were positioned vertically above the other, and the flow of fluid is stopped upon detection of a bubble, the detected bubble may be positioned at a different location depending on which detector 276a-b identified the bubble, which may be undesirable. Locating the light sources 274a-b and detectors 276a-b in substantially the same horizontal plane can also result in a more compact connector as compared to a configuration in which the sensors are positioned at different vertical positions.

The cassette 262 can also include one or more sensors for detecting whether an IV bag, or other target container, is attached to the connector 226a. In some embodiments, the system 200 can disable fluid transfer (e.g., by not allowing the motor to advance the plunger of the syringe 222) if no target container is attached to the connector 226a, thereby preventing unintentional discharge of fluid from the connector 226a. The sensors can be similar to, or the same as, the corresponding sensors described in the '703 Publication. The one or more sensors can use light to detect whether a valve of the target connector 294 is open or closed, and the system can allow transfer of fluid only when the valve is determined to be open. For example, one or more beams of light can be transmitted through the target connector 294 at a location where the target connector 294 is transparent in the closed position (e.g., through a transparent portion of the housing), and when the valve of the target connector 294 is opened, an opaque portion of the target connector 294 can be moved to block the beam of light, thereby indicating that an IV bag or other target container is attached to the target connector 294.

Figure 27:
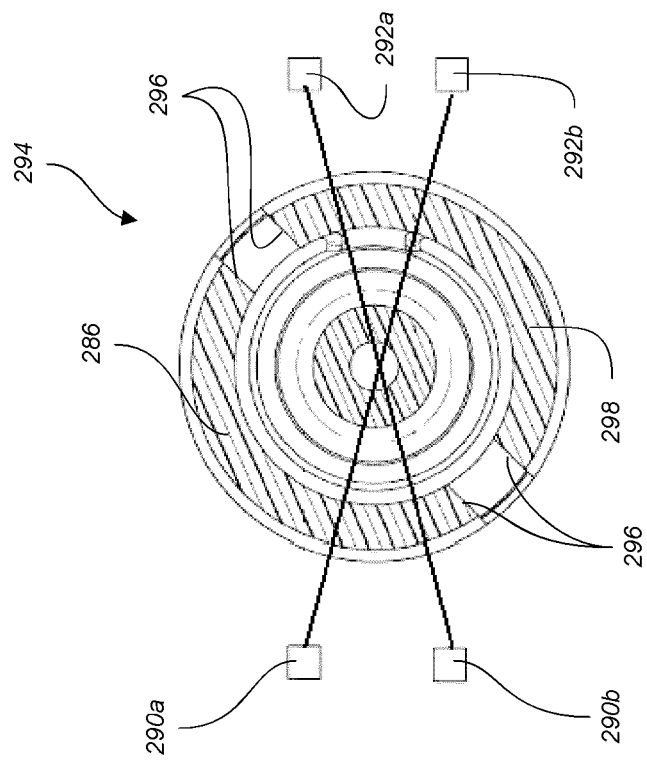
FIG. 27 is a cross sectional view of the male connector portion of the connector of FIG. 22 taken through a sensor beam intersection plane.

The cassette 262 can include two light sources 290a-b and two corresponding light detectors 292a-b. The system can be configured to allow the transfer of fluid only when both beams of light are blocked from reaching the corresponding detectors 292a-b. Thus, if light for one detector (e.g., 292a) is unintentionally blocked or otherwise diverted away from the detector (e.g., 292a) when no IV bag is attached, the system will continue to prevent fluid from being expelled from the syringe 222 if the other detector (e.g., 292b) detects light from the corresponding light source 290b. FIG. 27 is a cross sectional view of the target connector 294 portion of the connector 226 showing the light paths between the light sources 290a-b and the detectors 292a-b. In some embodiments, features of the target connector 294 (e.g., edges 296 of the housing 298) can interfere with the light beams when at certain orientations. For example, as the housing 298 rotates, the edges 296 may be positioned so that light from the light sources 290a-b is be reflected by the edges 296, or can be diverted by or trapped in the housing 298 (e.g., by total internal reflection). The light sources 290a-b and detectors 292a-b can be positioned so that when the valve is closed (e.g., no IV bag attached) and when a disrupting feature interferes with light from on light source (e.g., 290a), the light from the other light source (e.g., 290b) can be aligned to pass through the target connector 294 with low enough disruption to trigger the corresponding detector (e.g., 292b).

In some embodiments, the light sources 290a-b and the detectors 292a-b can be aligned on substantially the same vertical plane, which can result in a more compact connector than if the sensors were positioned at different horizontal positions. The light beams can be angled so that they intersect the surfaces of the walls of the target connector 294 at an angle that is normal, or substantially normal (e.g., plus or minus 20°, 10°, 5°, 2°, or 1°) to the surfaces, thereby reducing the occurrence of unintentional (e.g., when no IV bag is attached) diverting of light away from the detectors 292a-b (e.g., by reflection, refraction, total internal reflection). The light used by the light sources 290a-b and the detectors 292a-b can use infrared light (e.g., near-infrared light) having a wavelength of at least about 800 nm and or less or equal to about 960 nm, or of at least about 860 nm and/or less than or equal to 900 nm, or of about 880 nm, although light of other wavelengths may also be used.

Many variations are possible. For example, the sensors can be arranged so that light from the one or more light sources 290a-b is permitted to reach the one or more detectors 292a-b when the valve of the target connector 294 is open, and so that the light is blocked when the valve is closed. Also, in some embodiments, a single light source and corresponding detector can be used to detect whether the valve of the target connector 294 is open or closed. In some embodiments, one or more optical sensors can be positioned so that the IV bag itself, or other component associated with the IV bag (e.g., a female connector), blocks the sensor light when the IV bag is attached.

Figure 28:
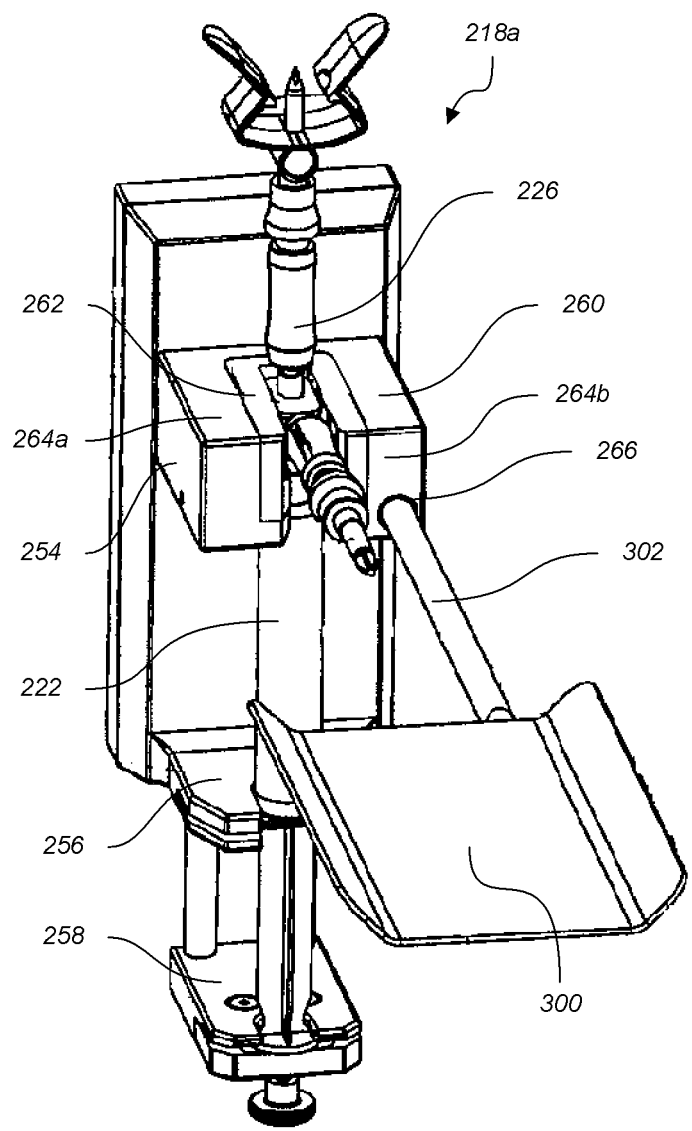
FIG. 28 shows an example embodiment of a transfer station having a tray attached thereto for supporting an IV bag.

FIG. 28 illustrates an example transfer station 218a with a tray 300 attached to the base member 260 of the upper mounting portion 254. The tray 300 can be attached to a shaft 302, which can be inserted into the hole 266 in the base member 260. The tray 300 can be configured to support the IV bag (not shown in FIG. 28). Additional details and variation relating to the tray 300, and the rest of the transfer station 218, are described in the '703 Publication.

In some embodiments, the IV bag 224a can be hung facing downward, as shown in FIG. 2. In the hanging configuration, the IV bag 224a can be located closer to the transfer station 218a (and to the housing 202) than when using a tray 300, as shown in FIG. 28. Thus, the hanging configuration can provide a more compact system. Also, as the IV bag 224a is filled with fluid, the weight of the fluid can shift the center of gravity of the system. In some embodiments, the weight of the housing 202 can prevent the system 200 from tipping as the center of gravity moves towards the IV bag 224a. In some embodiments, a foot member (not shown) can extend from the bottom of the housing 202 to prevent the system 200 from tipping. Because the hanging IV bag configuration (FIG. 2) can position the IV bag 224a closer to the housing 202 than when the tray 300 is used (FIG. 28), the center of gravity can remain closer to the center of the housing as the IV bag 224a fills when the IV bag 224a is in the handing configuration. Thus, the hanging bag configuration can increase the stability of the system 200, which can allow for a more light weight housing 202 to be used.

In some embodiments, the fluid pathway leading from the connector 226a to the IV bag 224a is not linear, and can include a turn downward towards the IV bag 224a. The turn in the fluid pathway can be at least about 60° and/or less than or equal to about 120°, or about 90°. A first portion of the fluid pathway (e.g., connected to the connector 226a) can extend substantially horizontally (e.g., plus or minus 30°, 15°, 5°, or less), and a second fluid pathway (e.g., connected to the IV bag 224a) can extend substantially vertically (e.g., plus or minus 30°, 15°, 5°, or less).

Figure 29:
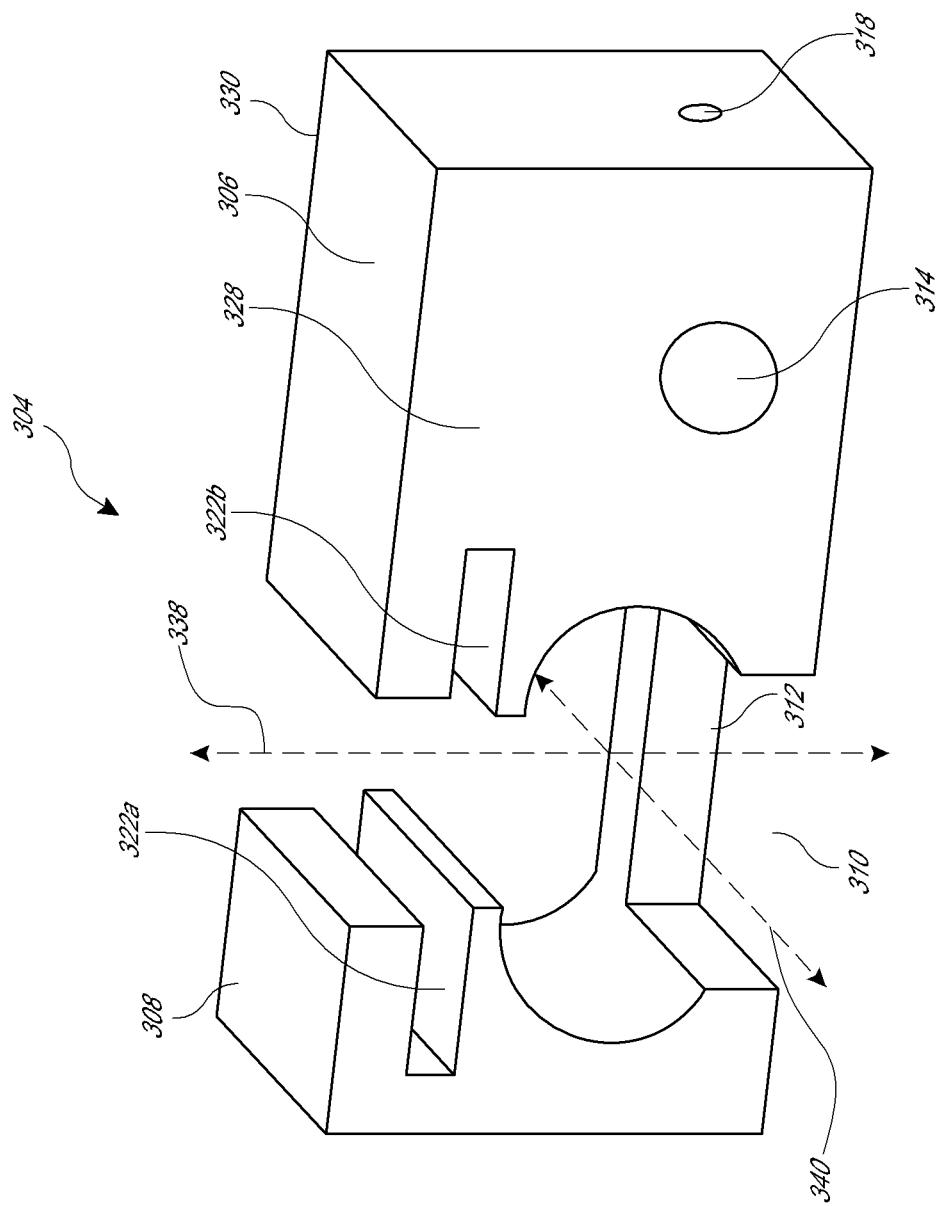
FIG. 29 is a perspective view of an example attachment for supporting an IV bag in a hanging configuration.
Figure 30:
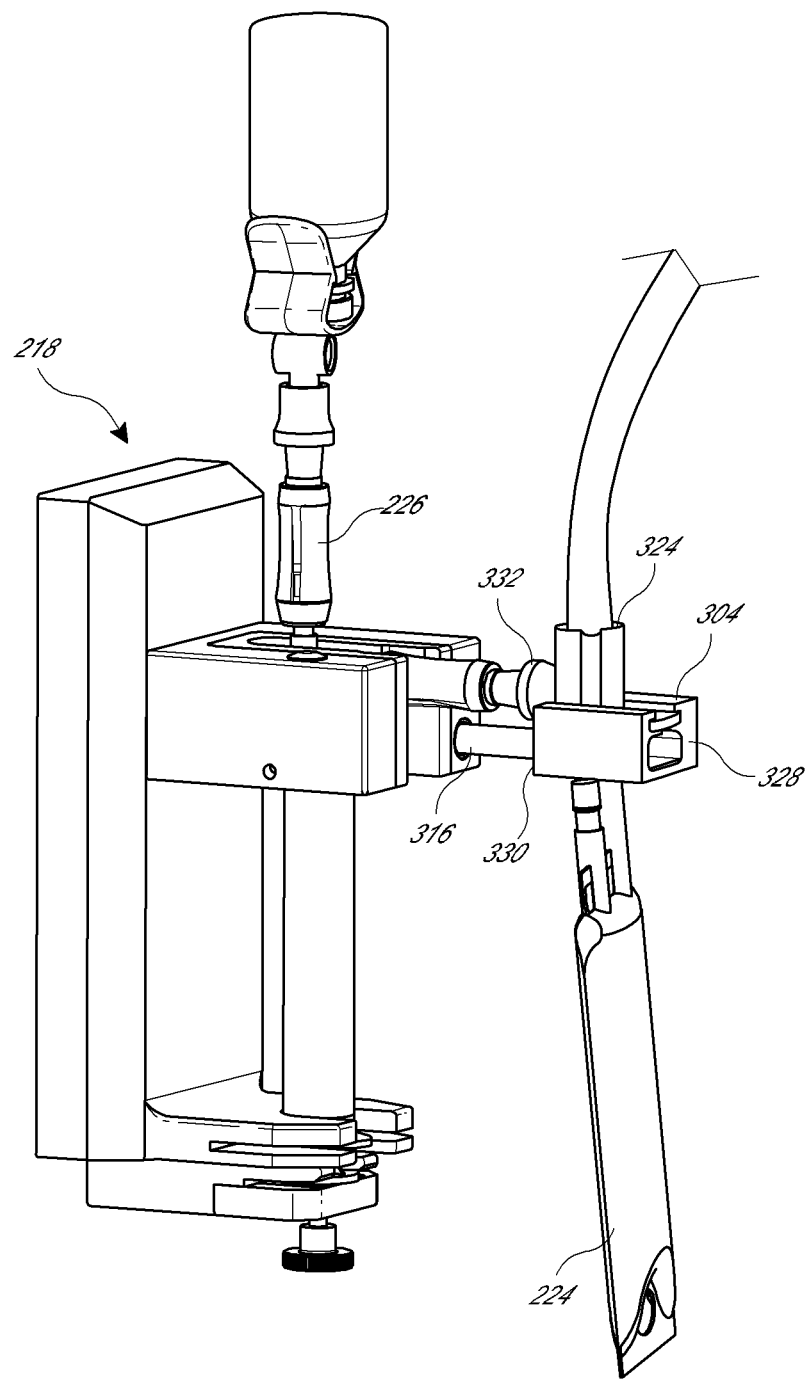
FIG. 30 is a perspective view of a transfer station using the attachment of FIG. 29 to hang an IV bag in a substantially vertical configuration.
Figure 31:
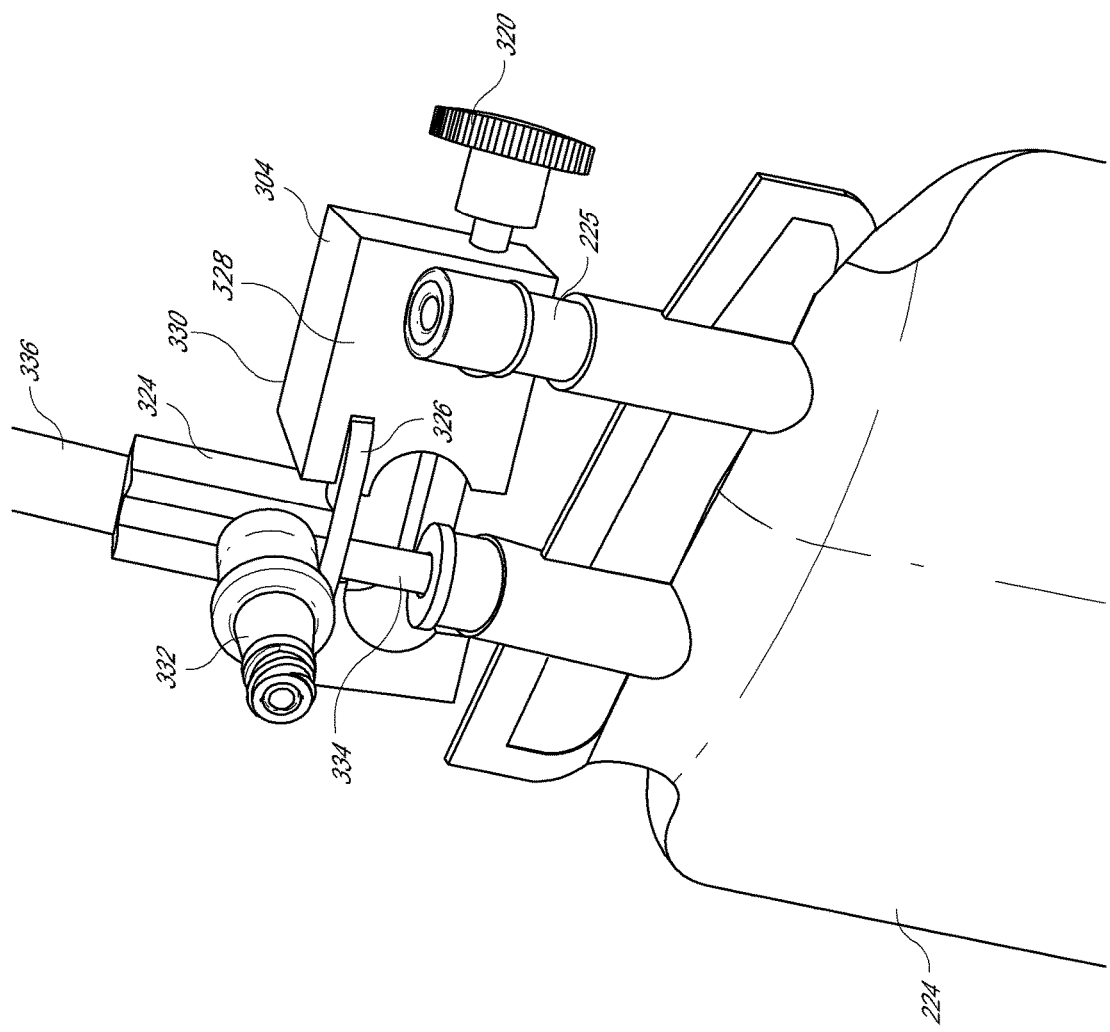
FIG. 31 shows the attachment of FIG. 29 with an support member and IV bag attached thereto.

FIG. 29 illustrates an example embodiment of an attachment 304 configured to hang an IV bag downward. FIG. 30 shows an IV bag 224 suspended in a substantially vertical hanging configuration by the attachment 304. FIG. 31 shows the attachment 304 and IV bag assembly removed from the rest of the system. The attachment 304 can include a first side 306 and a second side 308 with a gap 310 formed therebetween. An extension 312 can extend across the gap 310 to connect the first side 306 to the second side 308. The attachment 304 can include a hole 314 configured to receive a shaft 316 (which can be similar to, but shorter than, the shaft 302 of FIG. 28). A threaded bore 318 can extend through the attachment 304 at an angle transverse to the hole 314, and the threaded bore 318 can receive a thumb screw 320 that can be tightened to engage the shaft 316 to secure the attachment 304 to the shaft 316. In some embodiments, the shaft 316 can include a groove or hole configured to receive the end of the thumb screw 320 to prevent the attachment 304 from rotating about the shaft 316. Other quick release mechanisms can be incorporated to secure the shaft 316 to the attachment 304. In some embodiments, the shaft 316 can have a square, or other non-circular, cross sectional shape to prevent the attachment 304 from rotating about the shaft 316. The attachment 304 can be attached to the shaft 316 so that a front side 328 of the attachment 304 faces away from the transfer station 218 and so that a back side 330 of the attachment 304 faces towards the transfer station 218.

The attachment 304 can include one or more features (e.g., grooves 322a-b) configured to support the IV bag 224. The IV bag 224 can be attached to a support member 324 configured to engage the attachment 304. The support member 324 can have features (e.g., flange 326) configured to engage the corresponding features (e.g., grooves 322a-b) of the attachment 304 to removably attach the support member 324 to the attachment 304. Other manners of engagement between the support member 324 and attachment 304 are possible. For example, protrusions on the attachment 304 can engage grooves in the support member 324. The interface between the attachment 304 and support member 324 can be strong enough to support the weight of the IV bag 224 when containing fluid.

The support member 324 can have a fluid path to provide communication between the IV bag 224 and a connector 226. A connector 332 (e.g., a female connector such as a Clave® connector) can be attached to the support member 324 and can be configured to removably engage a corresponding connection portion of the connector 226a. In some embodiments, the connector 332 can extend directly from the support member 324, and in some embodiments, a portion of tubing can extend between the connector 332 and the fluid pathway through the support member 324. In FIG. 31, the connector 332 is shown extending away from the front side 328 of the attachment 304 for illustration purposes. In some embodiments, the support member 324 can be attached to the attachment 304 backwards from the orientation shown in FIG. 31, so that the connector 332 extends away from back side 330 of the attachment 304 and towards the transfer station 218 (as shown in FIG. 30).

The support member 324 can have a spike 334 extending from the flange 326 towards the IV bag 224. A fluid pathway can extend from the connector 332, through the support member 324, out the spike 334, and into the IV bag 224. In some embodiments, a tube 336 can extend from the support member 324 to allow a supplemental fluid to be transferred into the IV bag 224 in addition to the fluid transferred by the transfer station 218. For example, in some embodiments, the fluid transfer station 218 can transfer a medication into the IV bag 224, and an additional transfer station (e.g., 218b of FIG. 2) can transfer saline or other diluent into the IV bag 224 to obtain a specified concentration of the medication. Thus, in some embodiments, two input fluid pathways can combine (e.g., by a T- or Y-Connection) into a single output fluid pathway leading to the IV bag 224. In some embodiments, one or more check valves can be included to prevent fluid from the first fluid input from being driven out of the second fluid input and/or to prevent fluid from the second fluid input from being driven out of the first fluid input. In some embodiments, the fluid tube 336 can be omitted (e.g., if only one fluid is to be transferred to the IV bag 224), or the fluid tube 336 can be attached to the IV bag 224 by a supplemental line 225 of the IV bag 224.

The extension 312 that connects the first side 306 to the second side 308 of the attachment 304 can be located at a back portion of the gap 310 (e.g., the lower back portion) nearer to the transfer station 218. Thus, the support member 324 can be inserted into the gap 310 (e.g., with the flange 326 engaging the grooves 322a-b) from the front side 328 of the attachment 304 without disconnecting the attachment 304 from the transfer station 218. This can facilitate replacement of the IV bag 224. As shown in FIG. 29, the bottom of the gap 310 can be generally open to allow a fluid line to lead to the IV bag 224 and/or the top of the gap 310 can be generally open to receive the tube 336. In some embodiments the gap 310 can create an open pathway 338 leading substantially vertically through the attachment 304. The front of the gap 310 can be generally open (or completely open) to allow the support member 324 to be inserted therethrough. The back of the gap 310 can be generally open to receive the connector 332. In some embodiments, the gap can define an open pathway 340 extending substantially horizontally through the attachment 304. In some embodiments, the open substantially horizontal pathway 340 can allow a fluid line to extend through the attachment 304. For example, the attachment 304 can be attached to a shaft 302 that supports a tray 300 (as shown in FIG. 28), so that user has the option to position the IV bag 224 in the generally vertical configuration by attaching the IV bag 224 to the attachment 304 (e.g., using the support member 324), or to position the IV bag 224 in the generally horizontal configuration by laying the IV bag 224 on the tray 300. When the IV bag 224 is on the tray 300, the fluid line extending between the IV bag 224 and the connector 226 can pass through the gap 310 of the attachment 304, (e.g., generally along the substantially horizontal pathway 340).

Many variations are possible. For example, the back side of the gap 310 can be closed, and the connector 332 can be positioned higher on the support member 324 than illustrated so that the connector 332 so that the connector 332 can clear the attachment 304 as the support member 324 is inserted through the front of the gap 310.

Figure 32:
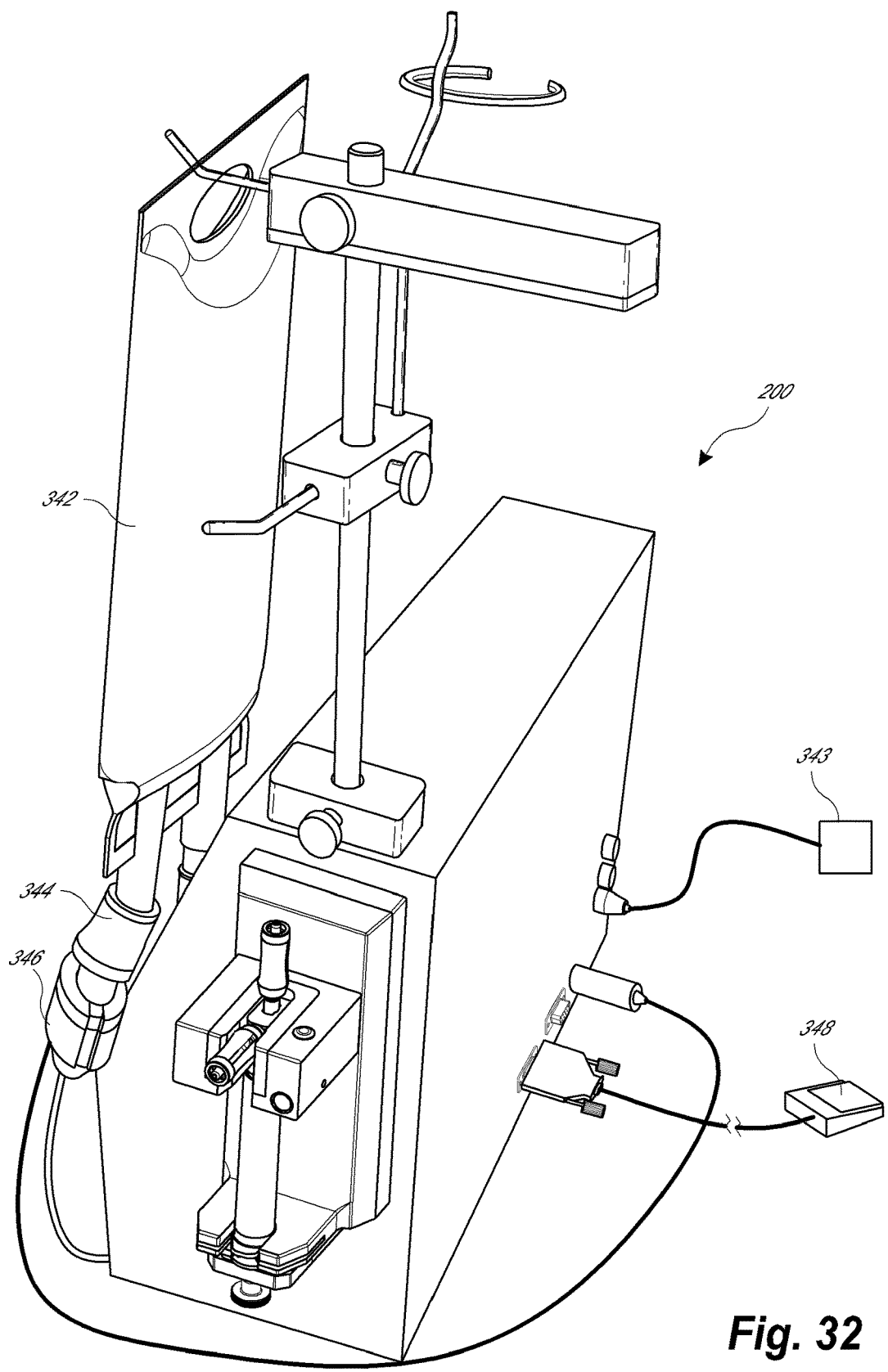
FIG. 32 shows the fluid transfer system of FIG. 2 using a fluid bag as a fluid source container and having a foot pedal.

FIG. 32 shows the fluid transfer system 200 using a fluid bag 342 instead of the source fluid vial 220b shown in FIG. 2. In some embodiments, a drip chamber 344 can be positioned between a source fluid container (e.g., the fluid bag 342, or vial 220a, or vial 220b) and the corresponding syringe pump to prevent air bubbles from being drawn towards the syringe pump, until the source fluid container runs dry. In some embodiments, an air detector 346 can be positioned between the fluid source (e.g., fluid bag 342) and the syringe pump. In some embodiments, the air detector 346 can be clamped, or otherwise attached, to the fluid line below the drip chamber 344. The air detector 346 can include a light source and light sensor similar to the other air detectors discussed herein. The air detector 346 can be in configured to provide a signal to a controller when air is detected, indicating that the fluid source may need to be replaced.

As shown in FIG. 32, the system 200 can include a foot pedal 348 in communication with a controller for the system 200. The foot pedal 348 can be configured to provide user input to the system 200, which can be used in addition to or instead of input received through the user interface 208. In some embodiments, the foot pedal 348 can issue a repeat command that causes the system 200 to perform a fluid transfer of the same amount as the previous fluid transfer.

The foot pedal 348 can allow the user to have both hands free (e.g., to replace IV bags after each fluid transfer of a multiple-IV bag order). The foot pedal 348 can provide various other signals to the controller, such as an accept command, a pause command, a start command, a cancel command, etc.

The system 200 can be in communication with an external system 343 by a cable or wire attached to a port on the fluid transfer system 200, or by a wireless communication connection, or any other suitable data connection. The external system 343 can be an external controller, a terminal (such as a computer), or an automated management system (such as a hospital information system (HIS)), etc. In some embodiments, the system can receive instructions from the external system 343. For example, in some cases the system 200 does not include a user interface as part of the system 200, and the controller can be configured to receive instructions from the external system 343, which can be a computer running a software program configured to provide instructions for the system 200. For example, the external computer 343 can provide a user interface to the user and can receive input from a user and can generate instructions for the system 200 based on the user input. In some embodiments, the external system 343 can be configured to interface a hospital information system (HIS) to generate instructions for the system 200, which can be, for example, based on requests or information gathered from a large number of terminals. In some embodiments, a software program running on the external computer 343 can coordinate fluid transfer tasks between two or more fluid transfer systems. The software program can also be used to calculate sophisticated configurations of dosages, to track dosage amounts for individual patients, and to provide warnings if problems are identified with patient dosage requests or other data.

In some embodiments, the external system 343 can include a printer that can be configured to automatically print labels for use with the fluid transfer system 200. For example, when a fluid transfer is performed, the printer can print a label automatically to be placed on the target container (e.g., IV bag). The label can include information such as the fluid type, the concentration, the amount of fluid, the intended patient, the requesting doctor, etc. In some embodiments, the printer can be directly attached to the fluid transfer system 200, such as by a wire or cable extending from a port on the system 200 or by a wireless data connection. The controller of the system 200 can be configured to generate the printer instructions for printing the labels. Though shown as an external system 343 with various possible applications, in some embodiments, some or all of the aspects of the external system 343 may be incorporated into the fluid transfer system 200.

In some embodiments, the system 200 can be used in combination with a fume hood 350. For example, a fume hood 350 is shown schematically in FIG. 33 with a fluid transfer system 200 inside of a ventilation area 352. An exhaust duct 354 can remove air from the ventilation area 352, which can prevent or reduce the occurrence of any leaked fluids or other materials escaping from the ventilation area 352. The fume hood 350 can also include one or more baffles 356 to control the flow of air through the ventilation area 352.

Figure 34:
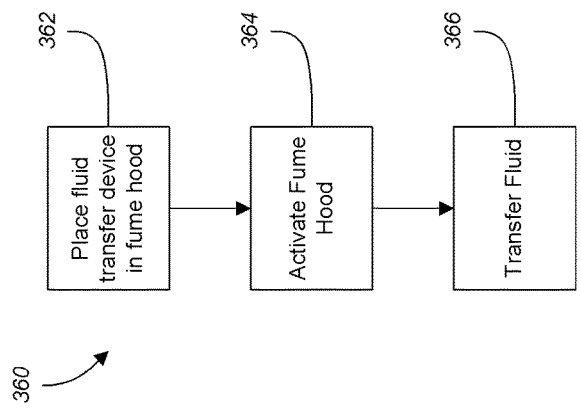
FIG. 34 is a flow diagram illustrating an example embodiment of a method for operating a fluid transfer device in a fume hood.
Figure 33:
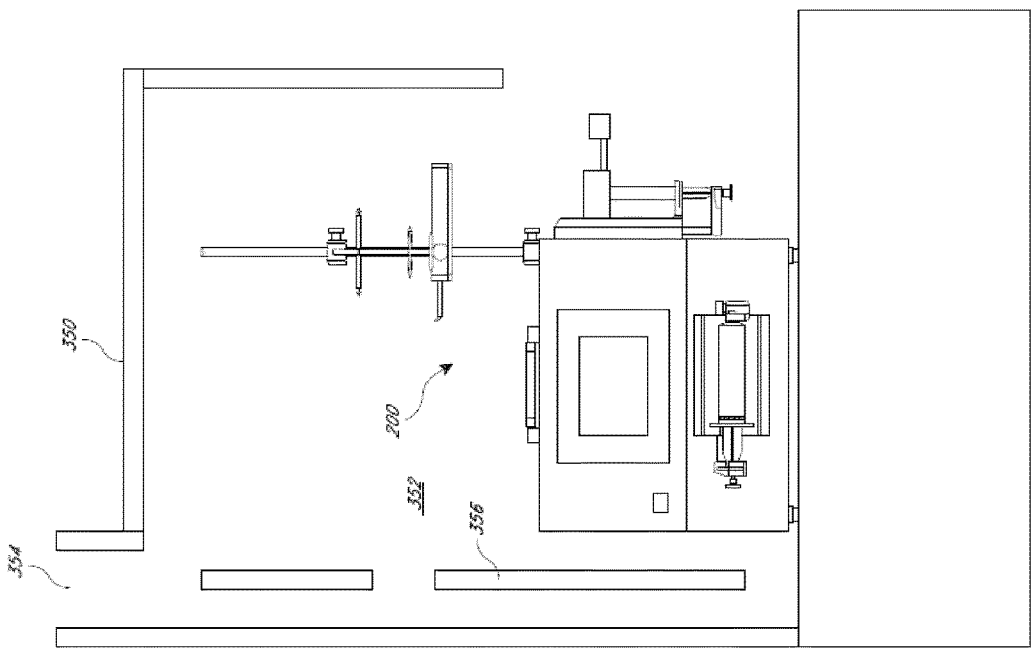
FIG. 33 shows the fluid transfer system of FIG. 2 positioned inside an example embodiment of a fume hood.

FIG. 34 is a flowchart showing a method 360 for transferring fluid using a fluid transfer system and a fume hood. At block 362, a fluid transfer system can be positioned in a flume hood, as shown in FIG. 33, for example. In some embodiments, block 362 can be omitted, for example, if the fluid transfer system is already located in the fume hood. At block 364, the fume hood can be activated, thereby producing a flow of air that can prevent or reduce the amount of particles escaping from the fume hood. At block 366, the fluid transfer system can be used to transfer fluid, or some other operation can be performed using the fluid transfer system. In some embodiments, the fume hood can be activated for some actions and deactivated for other actions. For example, the fume hood can be activated when connectors on the fluid transfer system are being disengaged and/or engaged (e.g., when replacing an IV bag or fluid vial). In some embodiments, the fume hood can be turned off during fluid transfer. In some embodiments, the system can be in operable communication with the fume hood so that the system can automatically activate and deactivate the fume hood as needed. For example, when the system receives a fluid transfer instruction, the system can activate the fume hood, and the system can deactivate the fume hood after completion of the fluid transfer.

Figure 35:
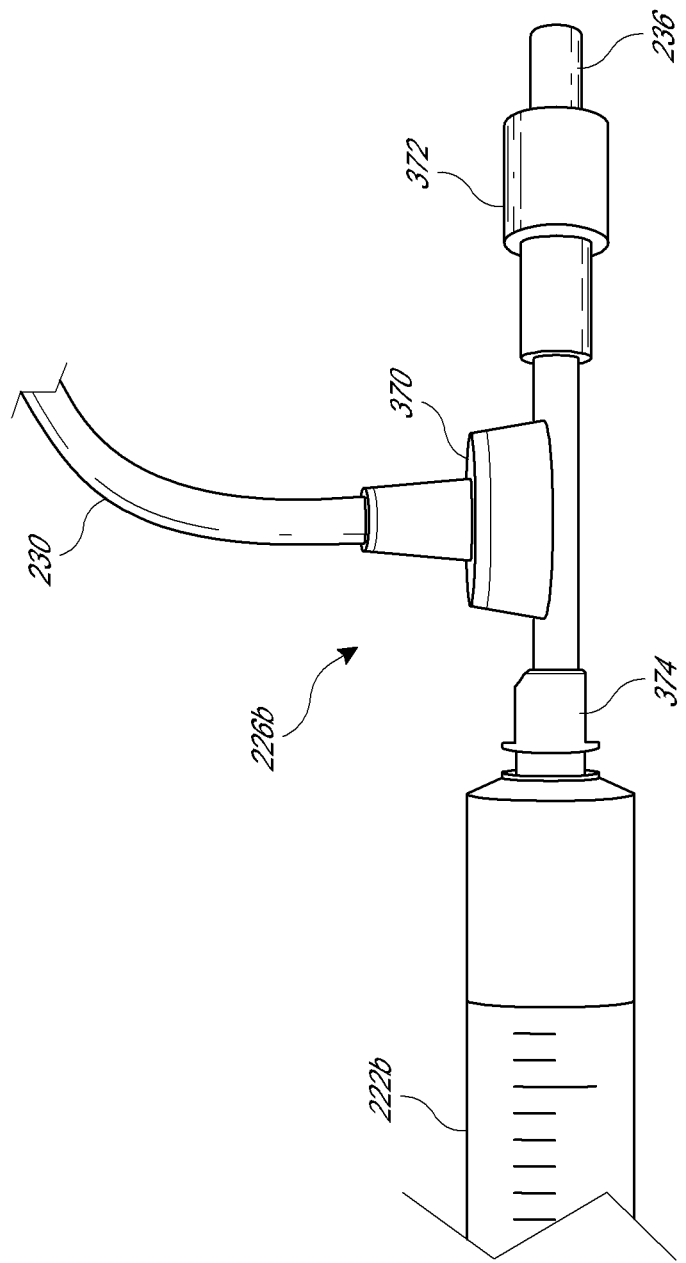
FIG. 35 shows a connector for a transfer station of the system of FIG. 2.

FIG. 35 is a detailed view of the connector 226b for the second fluid transfer station 218b of the system 200 (also shown in FIG. 2). The connector 226b can have an inlet 370 configured to receive the tube 230 for transferring fluid from a source container (e.g., a saline vial or bag) to the connector 226b, and an outlet 372 configured to receive tube 236 for transferring fluid from the connector 226b towards a target container. A syringe 222b can be attached to an intermediate connection 374 of the connector 226b. The connector 226b can have one or more check valves configured to control the flow of fluid through the connector 226b. When the syringe plunger is retracted, fluid can flow from the tube 230, into the inlet 370, to the intermediate connection 374, and into the syringe 222b, and the one or more check valves can prevent fluid from flowing into the connector 226b from the outlet 372. When the syringe plunger is advanced, fluid can flow from the syringe 222b, into the intermediate connection 374, through the connector 226b, and out the outlet 372 and tube 236, and the one or more check valves can prevent fluid from flowing out of the connector 226b through the inlet 370. The one or more check valves can include a duckbill structure, a disc, a flap, or any other suitable check valve structure.

Figure 36:
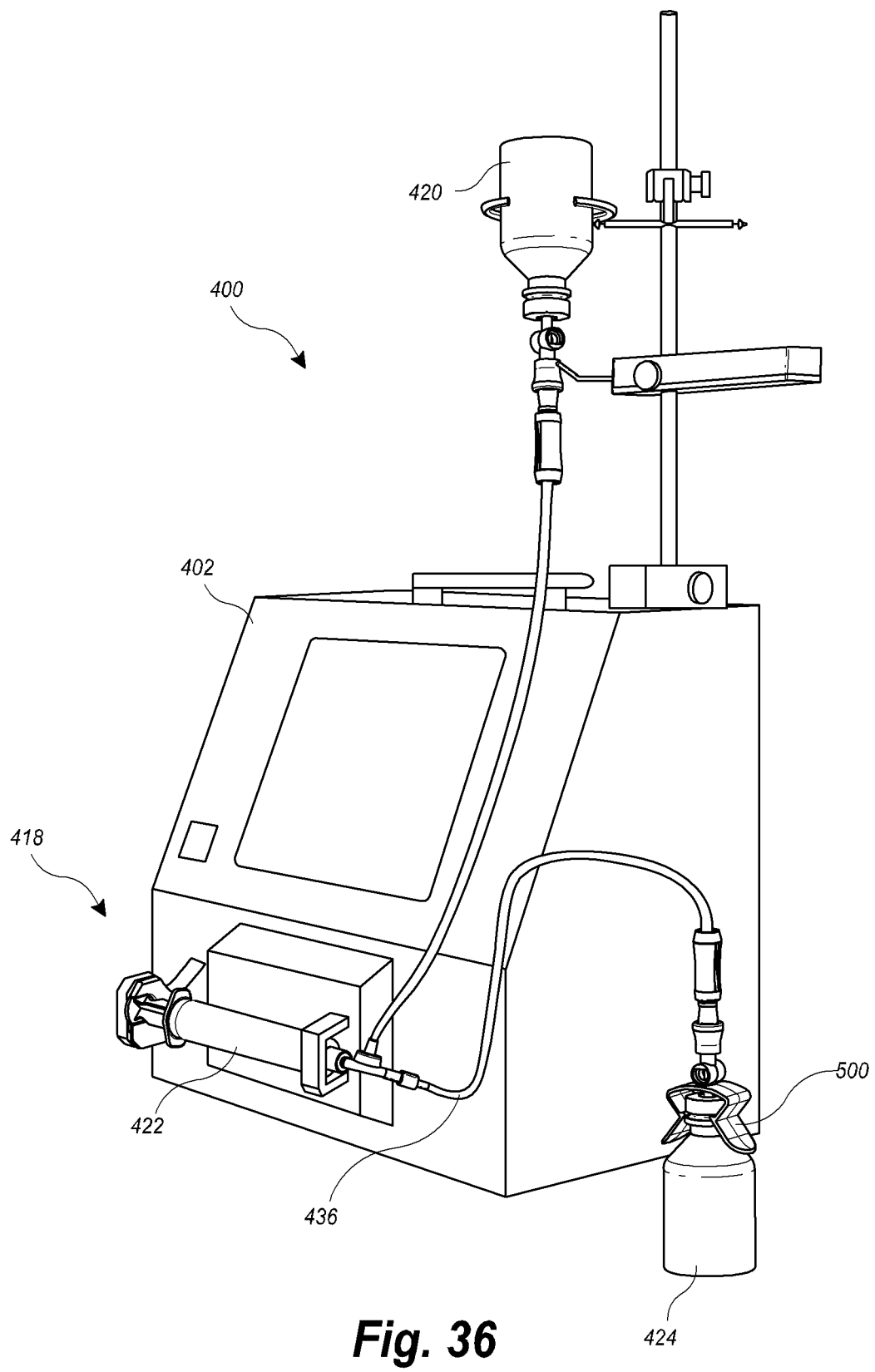
FIG. 36 shows an example embodiment of a fluid transfer system having a transfer station configured to transfer fluids that may not be dangerous, expensive, and/or sensitive, such as for reconstitution and/or dilution of medication.

Thus, in some regards, the transfer station 218b and connector 226b can operate in a manner similar to the transfer station 218a and 226a described herein. In some embodiments, the transfer station 218b can be configured for transfer of fluids that are not dangerous, expensive, or sensitive to ambient air (e.g., saline or water). For example, in some embodiments, the transfer station 218b does not include corresponding connectors (e.g., male and female closable luer connectors) configured to prevent leaking of fluids during changing of components. In some embodiments, the fluid transfer system 200 can be used to transfer only fluids that are not dangerous, expensive, or sensitive to ambient air (e.g., saline or water), for example, for reconstitution or dilution of medications. FIG. 36 is a perspective view of a fluid transfer system 400, which can be similar to, or the same as, the fluid transfer system 200 in many regards, except that the fluid transfer system 400 does not include a fluid transfer station configured to transfer fluids without exposure to the ambient environment. For example, the system 400 can include a single transfer station 418 that can be similar to, or the same as, the transfer station 218b of the system 200. In some embodiments, the housing 402 can be smaller than in the illustrated embodiment.

In some embodiments, the system 200 and the system 400 can be used as a reconstituting or diluting device by transferring a reconstituting fluid or diluent into a target container 424 (e.g., a vial). Although some disclosure relating to reconstitution and/or dilution is discussed in relation to the transfer station 418 of system 400, the transfer station 218b of system 200 can also be used. Although the transfer station 218a can also be used for reconstitution and/or dilution, in some embodiments, the transfer stations 218b and 418 can provide a simpler solution than 218a.

In some embodiments, a vial adapter 500 can be used to provide access to the internal chamber of the vial 424. The vial adapter can be a pressure-regulated vial adapter, such as a version of the Genie® vial adapter, manufactured by ICU Medical, Inc., of San Clemente, Calif.). Various embodiments and features relating to the vial adapter 500 are disclosed in the '157 Publication.

Figure 38:
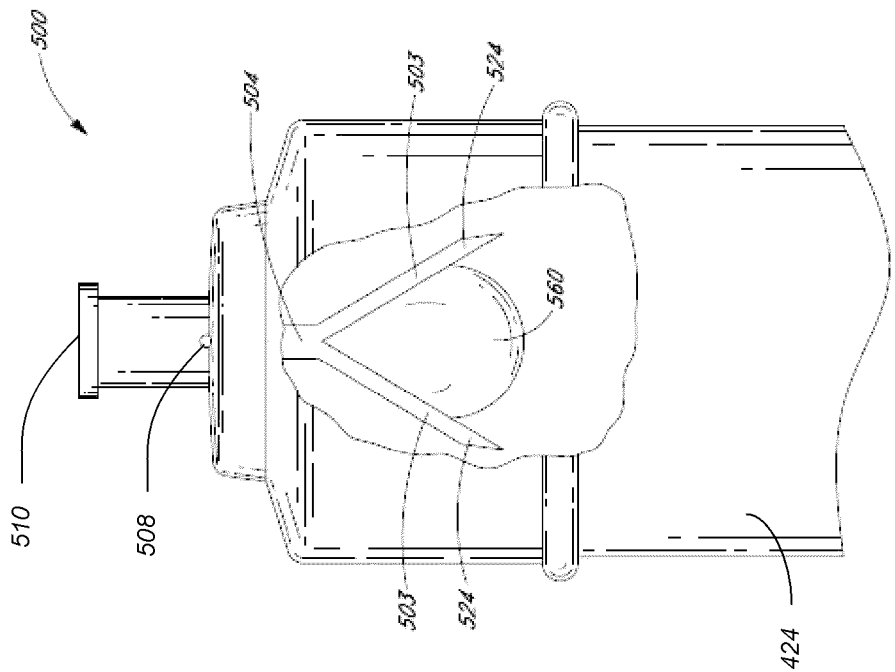
FIG. 38 shows the vial adapter of FIG. 37 with a vial attached thereto.
Figure 37:
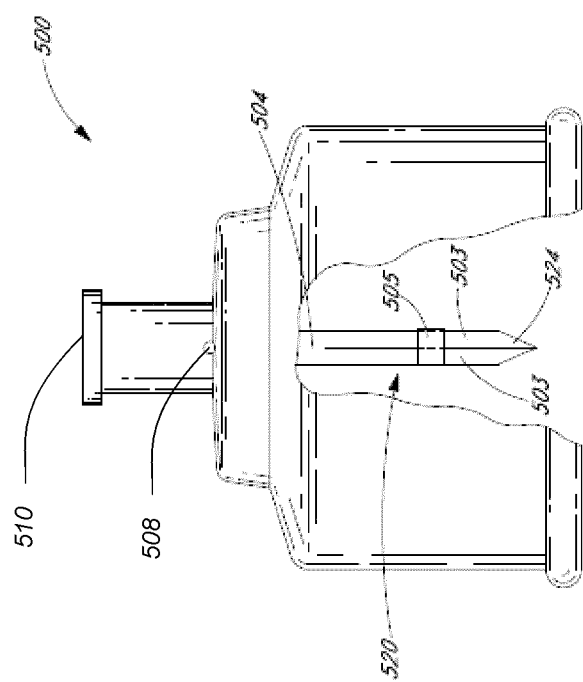
FIG. 37 shows an example embodiment of a vial adapter that can be used with the fluid transfer system of FIG. 36.
Figure 40:
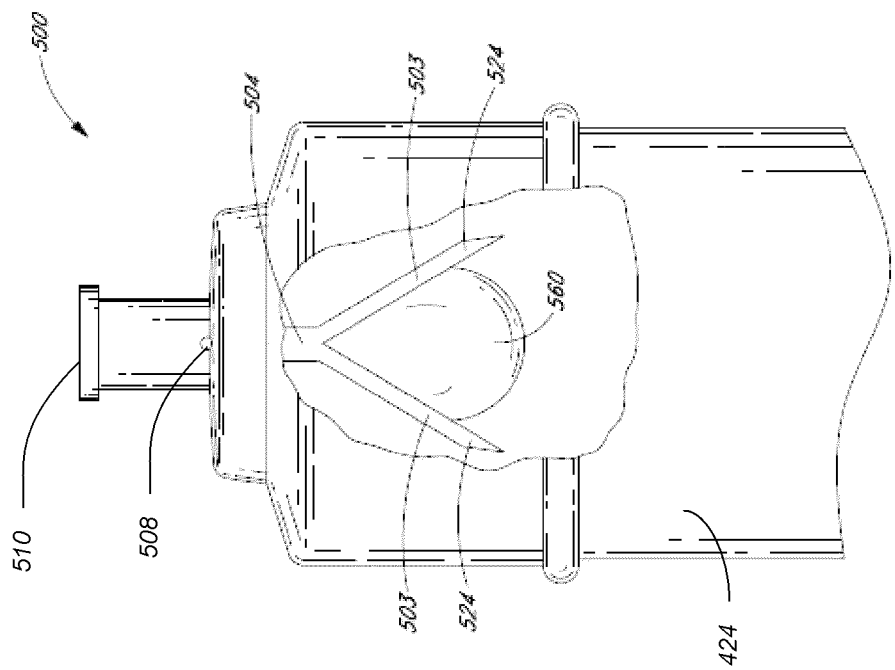
FIG. 40 shows the vial adapter and vial of FIG. 38, having a vial adapter bag in an inflated configuration.

One embodiment of a vial adapter 500 is illustrated in FIGS. 37-40. The vial adapter 500 can include a piercing member 520, including a tip 524 and a plurality of sleeve members 503, which can be biased outwardly. The sleeve member 503 can meet at a base 504 of piercing member 520. In some embodiments, the sleeve members 503 can be held closed prior to insertion of the piercing member 520 through a septum of the vial 424 (e.g., using a jacket 505), as shown in FIG. 37. As the piercing member 520 is inserted through the septum, the jacket 505 can be slide down the piercing member 520 by the septum until the sleeves 503 are allowed to open (as shown in FIG. 38). When the sleeves 503 open, a bag 560 can be deployed and can be partially filed with air that enters the vial adapter 500 via an air hole 508. Thus, in the default resting position, the bag 560 can occupy a first volume within the vial 424.

Figure 39:
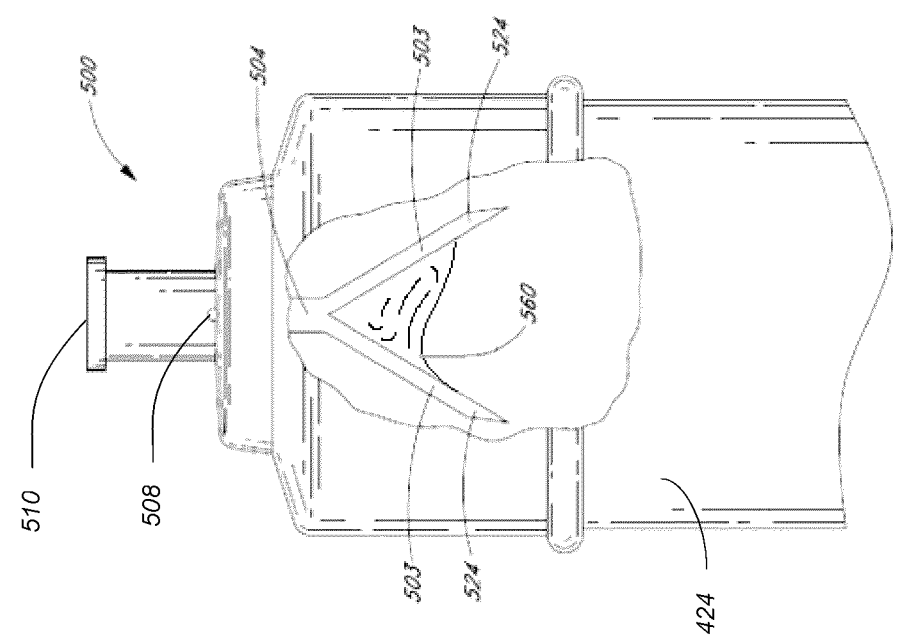
FIG. 39 shows the vial adapter and vial of FIG. 38, having a vial adapter bag in a deflated configuration.

The vial 424 can include a concentrated medication, which can be in powder form, and fluid (e.g., saline or water) can be transferred into the vial 424 using the fluid transfer station 418 of the system 400 to dilute or reconstitute the medication. Fluid can enter and/or exit the vial 424 via the fluid pathway 510. Fluid can be transferred by retracting the plunger of the syringe by a specified amount corresponding to the desired volume of fluid from a source container (e.g., vial 420), and by advancing the plunger to drive the fluid from the syringe 422 into the vial 424. As the fluid enters the vial 424, the bag 560 can deflate, as shown in FIG. 39 to a second volume that is smaller than the first volume, and air from the bag 560 can be expelled via the air hole 508. Thus, the bag 560 can change in volume to prevent, or reduce, pressure from building up inside the vial 424.

Once reconstituted or diluted, fluid from the vial 424 can be withdrawn (e.g., for administration to a patient or other use). The vial 424 and vial adapter 500 can be disconnected from the fluid transfer system, for example, by disengaging the connector 440 (which can be coupled to the vial adapter 500) from the connector 438 (which can be coupled to the tube 436). The vial adapter 500 can remain attached to the vial 424, and the bag 560 an remain in the at least partially deflated state while disengaged. The connector 440 attached to the vial adapter 500 can be configured to close when disengaged to prevent fluid from the vial 424 from escaping. Fluid can be withdrawn from the vial 424 by engaging the connector 440 with a corresponding connector to reestablish a fluid connection to the internal chamber of the vial 424. For example, the vial 424 and vial adapter 500 can be attached to a transfer station (e.g., 218a or 218b), for example, in order to transfer precise amounts of the reconstituted and/or diluted fluid from the vial 424 to a target container (e.g., an IV bag). As fluid is withdrawn from the vial 424, the bag 560 can inflate to a third volume that is larger than the second volume to at least partially compensate for the volume of fluid removed from the vial 424. The third volume can be smaller than the first volume, for example, if only a small portion of the fluid is withdrawn, or the third volume can be larger than the first volume, for example, if a relatively large volume of fluid is withdrawn from the vial 424.

Many vial adapter designs can be used other than that shown in the illustrated embodiments. Additional embodiments and details are provided in the '157 Publication.

Figure 42:
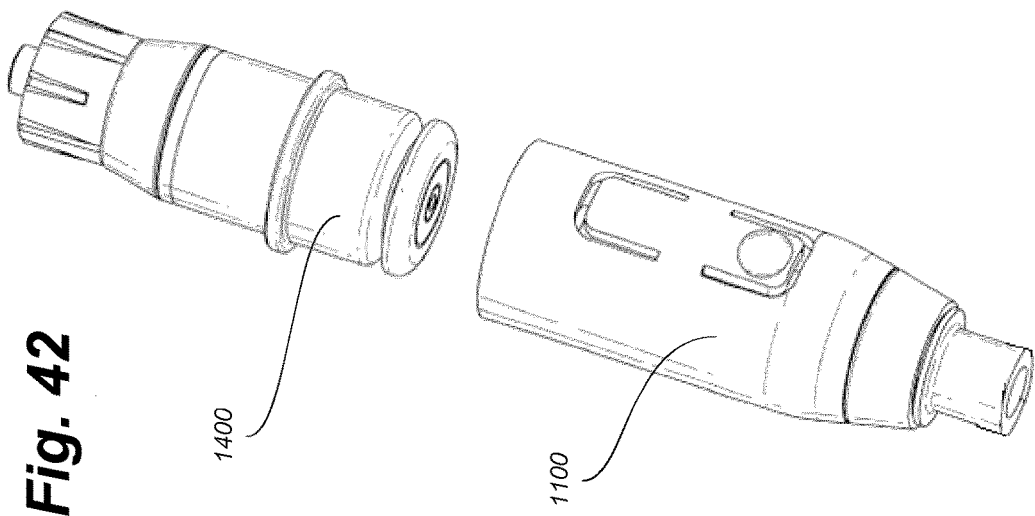
FIG. 42 shows a male connector portion of the connector of FIG. 41 along with a corresponding female connector in an unengaged configuration.
Figure 41:
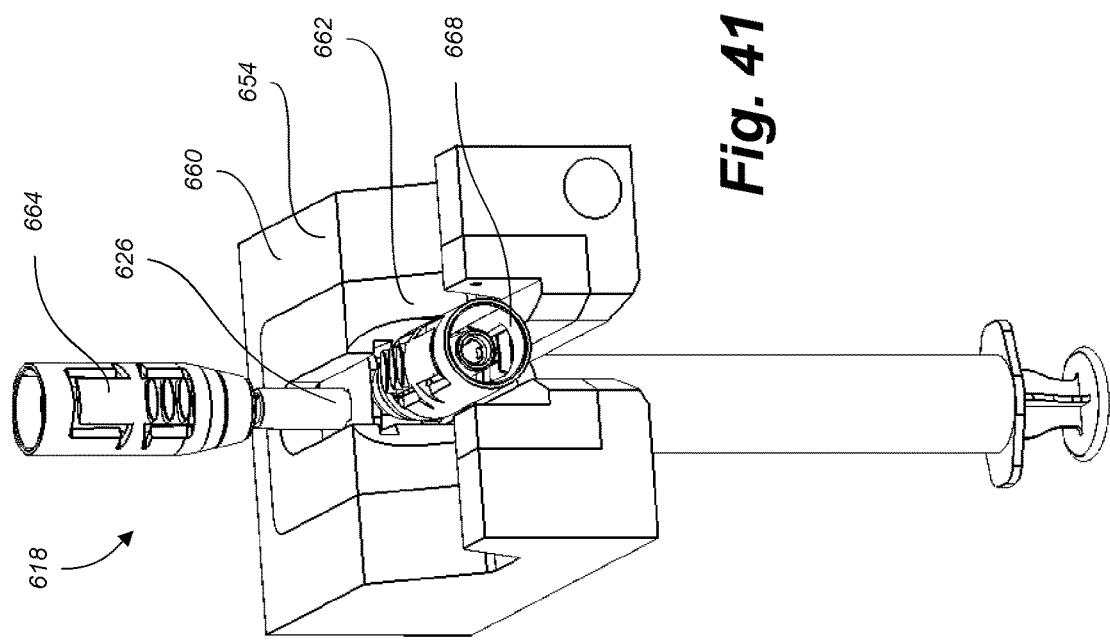
FIG. 41 shows an example embodiment of a connector and upper mounting module that can be used with a fluid transfer system.

FIG. 41 is a perspective view of an example embodiment of a portion of a transfer station 618, which can have features similar to, or the same as, other transfer stations disclosed herein. FIG. 41 illustrates an upper mounting portion 654 having a base member 660 and a cassette 662. A connector 626 can be received by the upper mounting portion 654 in a manner similar to that described herein for the connector 226a and upper mounting portion 254. The connector 626 can include a source connector portion 664 and a target connector portion 668, one or both of which can be similar to, or the same as the closable male connector 1100 in the '793 Application. FIG. 42 shows the male connector 1100 with a corresponding female connector 1400 (also described in the '793 Application) in a disengaged configuration. It will be understood that various connectors described herein can be replaced with the connectors 1100 and 1400 from the '793 Application. The '793 Application also discloses a male connector 100 and a female connector 400, which can be used in place of various connectors disclosed herein. Also, where a male connector is described, in some cases a female connector can be used, and vise versa. Thus, the connector 626 can use female connectors 1400 for the source connector portion 664 and/or for the target connector portion 668. The '793 Application also discloses a male connector, identified by reference number 100, and a corresponding female connector, identified by reference number 400, that can be used in place of various connectors described herein.

Figure 43:
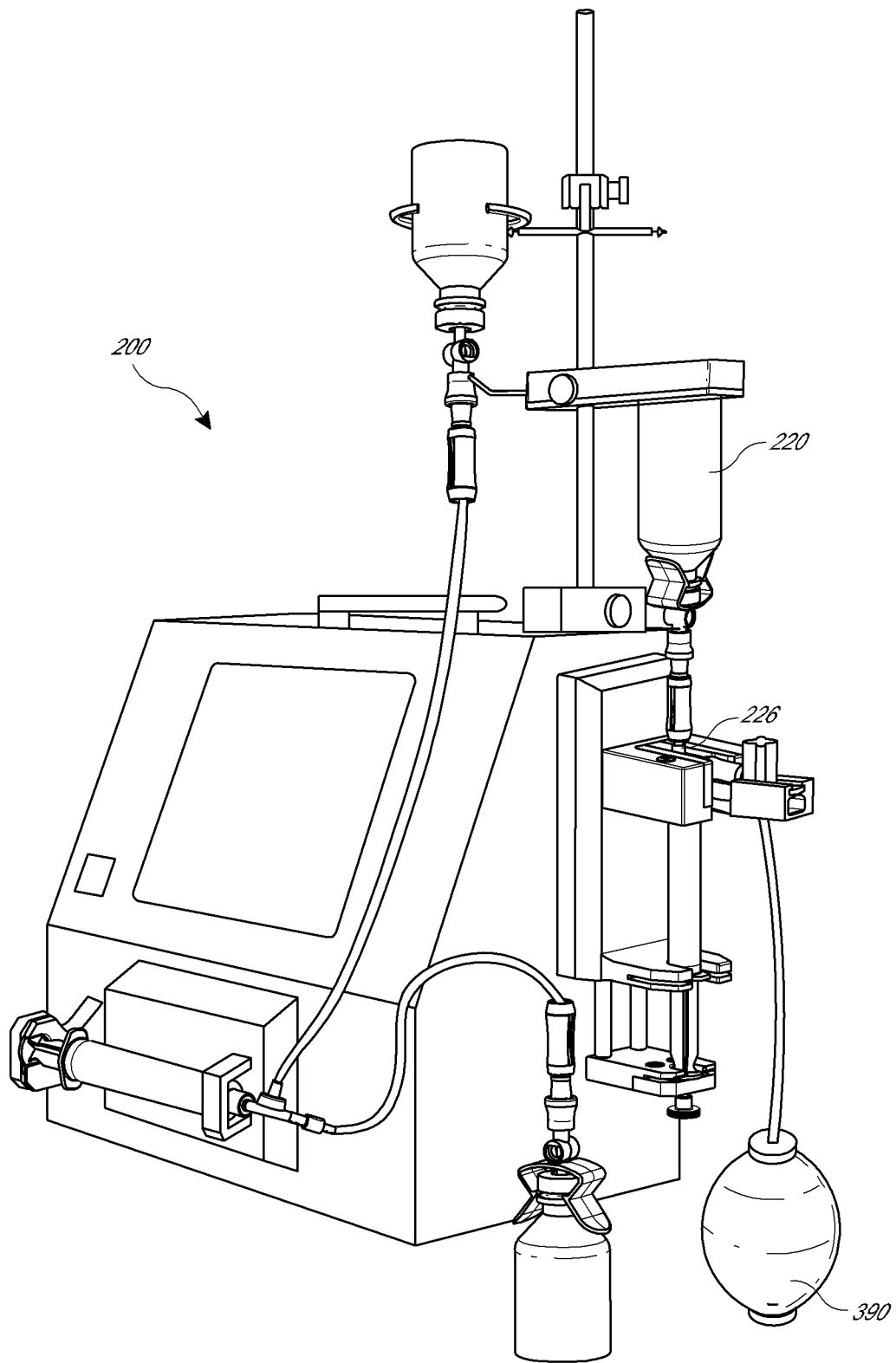
FIG. 43 shows the fluid transfer system of FIG. 2 with an example embodiment of an elastomeric pump attached thereto.

Various types of target containers can be used. For example, as shown in FIG. 43, the fluid transfer system 200 can be used to transfer fluid into an elastomeric pump 390. In some embodiments, an elastomeric pump 390 can include a bladder that can be filled with a fluid causing the bladder to stretch and exert a pressure on the fluid therein. The outlet of the elastomeric pump can restrict the flow of fluid so that the pressure drives the fluid out of the bladder via the outlet at a generally constant rate over a time (e.g., one hour to several days). In some embodiments, a considerable force may be required to fill the elastomeric pump 390 since filling is resisted by the expanding bladder. The resistance can make it difficult to fill the elastomeric pump 390 by hand, especially if done repeatedly, and especially if precise amounts of fluid are to be transferred. Thus, using the system 200 to fill elastomeric pumps 390 can increase speed and accuracy and can decrease fatigue on an operator.

Figure 44:
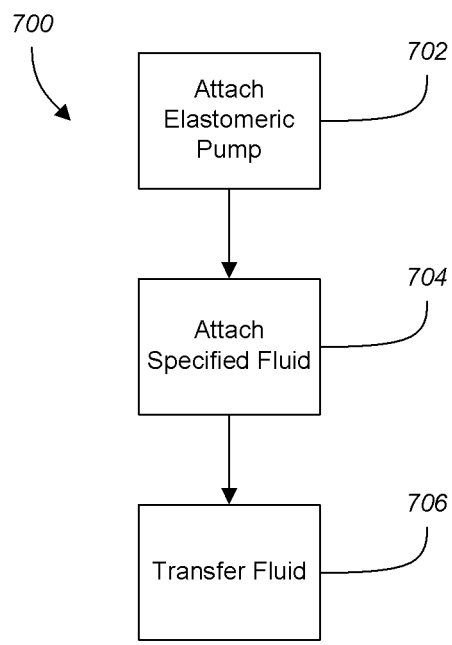
FIG. 44 is an example embodiment of a method for filling an elastomeric pump.

FIG. 44 is a flow diagram of a method 700 for filing an elastomeric pump 390. At block 702, the elastomeric pump 390 is attached to the system 200. For example, a tube leading to the elastomeric pump 390 can have a female connector that is configured to interface with a male connector portion on the outlet of the connector 226. At block 704, a specified fluid can be provided by attaching a vial 220 to the system 200. In some embodiments, block 704 can be omitted if the specified fluid is already in the attached vial 220. At block 706, the system 200 can transfer fluid into the elastomeric pump 390 by actuation the syringe plunger as described herein. The motor of the system 200 can be configured to overcome the resistance provided by the expanding bladder of the elastomeric pump 390 and can be configured to stop once the desired amount of fluid has been transferred.

Figure 45:
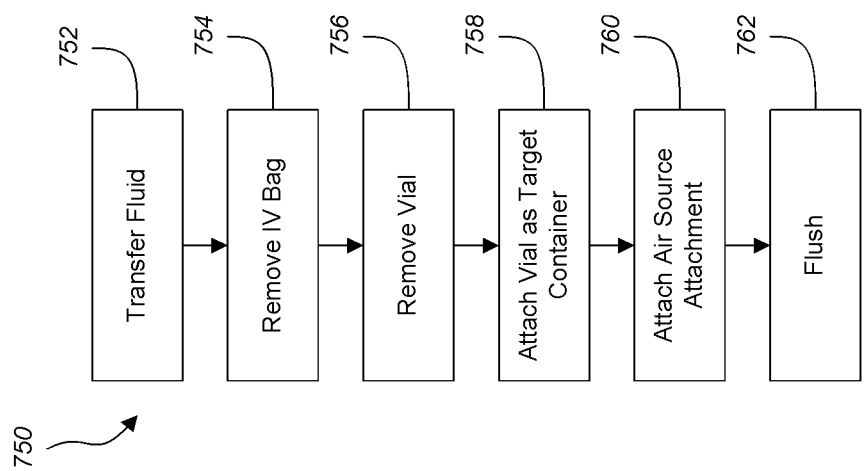
FIG. 45 is an example embodiment of a method for flushing a connector.

In some embodiments, the fluid transfer system can be configured to clear fluid out of the fluidics system, either automatically or upon instructions received from an operator (e.g., using a "clear" button). FIG. 45 is a flowchart showing an example method 750 of a fluid clearing method. At block 752, the system can transfer fluid. For example, the system can actuate a plunger of a syringe pump to draw fluid out of a source container (e.g., vial) and the system can advance the plunger to drive the fluid from the syringe pump into a target container (e.g., IV bag), as described herein. Once the specified amount of fluid has been transferred, the target container can be removed at block 754. In some embodiments, another target container can be attached to the system and another fluid transfer procedure can be performed using the same type of fluid drawn from the same source container. However, in some embodiments, the source container can be removed at block 756, for example, if no additional fluid transfers are to be performed and the system is to be shut down, or if a next fluid transfer is for a different type of fluid. In some embodiments, a volume of fluid remains in the connector after a fluid transfer, and the system can be used to flush the remaining fluid out of the connector so that the flushed fluid (which can be expensive) can be recovered for later use.

At block 758, a new target container can be attached to receive the flushed fluid. For example, the vial (or other container) that was used as the source container for the fluid can be attached to the system as the target container so that the flushed fluid can be directed back into the container were it started. In some embodiments, the vial or associated vial adapter can be configured to regulate pressure in the vial as the flushed fluid is inserted therein, for example, by deflating a volume variable bag associated therewith, as described in the '157 Publication. In some embodiments, the vial and/or vial adapter does not have a variable volume component and the volume inserted into the vial can be small enough that the pressure in the vial is not raised beyond an acceptable threshold.

Figure 46:
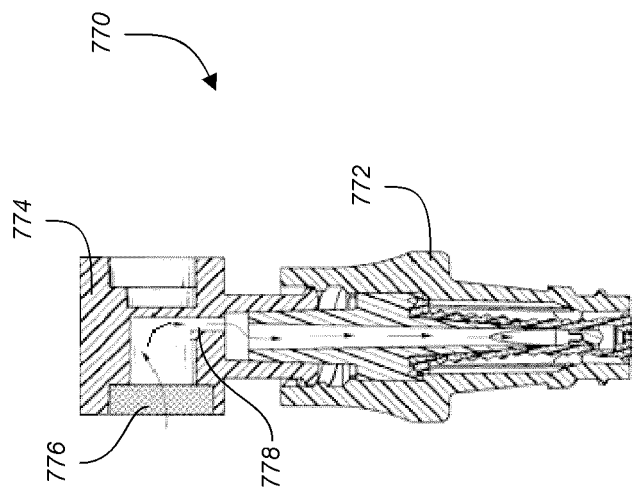
FIG. 46 is a cross sectional view of an air source attachment.

At block 760, a new source attachment can be attached to the system. The source attachment can allow air to be drawn into the connector. For example, the new source attachment can be an empty vial and adapter similar to the vial 3907 and adapter 3908 of FIGS. 7 and 8. Air can enter through the filter 3948 and pass through the empty vial 3907, pass through the female connector 3944, and enter the connector to flush the fluid contained therein. In some embodiments, the source attachment does not include a vial or other container. For example, FIG. 46 shows an example embodiment of an air source attachment 770 that includes a connector 772 that is configured to engage the source connector portion of the connector being flushed. An air intake element 774 can be attached to the connector 772. The air intake element 774 can include a one way air valve or filter 776 configured to allow air to enter the air intake element 774 and to prevent air from exiting through the filter 776. A pathway can lead from the filter 776 to the connector 772 to allow air to enter through the filter 776 and travel through the connector 772. In some embodiments, the air intake element can be integrally formed with the connector, for example, by placing the filter 776 at the male end of the connector 772 shown.

In some embodiments, a fluid source container can be attached at block 760, for example, to flush the fluid out of the connector using saline or water. However, in some embodiments, the fluid being flushed can become diluted or contaminated by the flushing fluid. Thus, it can be advantageous to use air in some embodiments. In some embodiments a flushing fluid can be used, such as a cleaning liquid, to flush the connector in order to clean the connector. In some embodiments, the connector can be cleaned for later use. In some embodiments, the connector can be disposable, and can be cleaned with a flushing fluid prior to being discarded, for example, if the transferred fluid is hazardous.

At block 762, the system can flush fluid from the connector into the target container (e.g., into the vial that had been used as the source container). For example, the syringe pump can draw air (or other flushing fluid) through the inlet of the connector, and the syringe pump can then push the air out through the connector outlet towards the target container so that the air drives some or all the fluid out of the connector and into the target container (e.g., the vial that had been the source container). In some embodiment, the system can flush the connector at block 762 in response to input received from a user or from an outside system, such as by pressing a "clear cassette" or "flush" button. In some embodiments, the system can be configured to disregard the air bubble sensor during the flushing procedure so that the system does not stop the motor when air is detected entering the connector.

Figure 47:
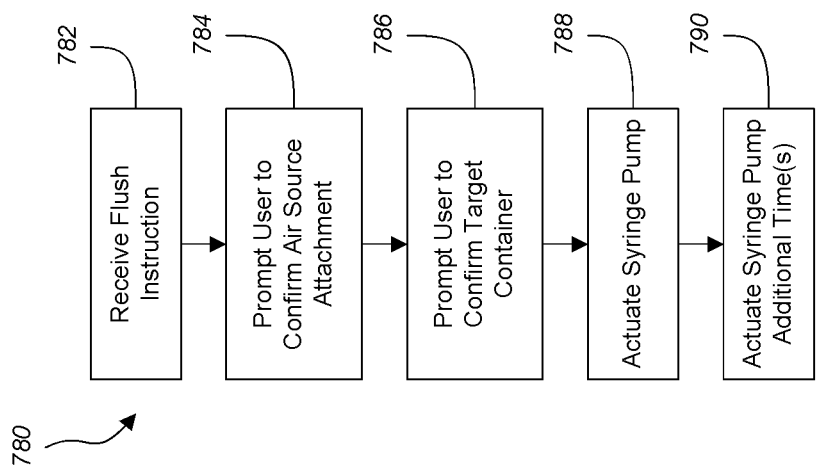
FIG. 47 is an example embodiment of a method for flushing a connector.

FIG. 47 is an example embodiment of a method 780 for flushing the connector. At block 782 the system can receive a flush instruction. The flush instruction can come from a user through a user interface (e.g., by pressing a "clear cassette" or "flush" button, or from an outside system via a data connection to the system). At block 784 the system can prompt the user (e.g., via the user interface) to attach, or confirm attachment of, the new source attachment (e.g., air source attachment 770) to the connector. At block 786 the system can prompt the user (e.g., via the user interface) to attach, or confirm attachment of, an appropriate target container, which can be the container that had served as the source container during the last fluid transfer.

At block 788, the system can actuate the syringe pump, which in some cases can be the first of multiple syringe actuations for flushing the connector. Actuating the syringe can draw air (or flushing fluid) through the connector to drive some or all of the transferred fluid out of the connector. In some embodiments, the system can actuate the syringe a second time at block 790, and can actuate the syringe any number of additional times as needed to drive residual fluid out of the connector. The system can disregard the air bubble sensor so that air is allowed to be drawn through the connector during the flushing procedure. The method 780 can be modified, for example, to omit one or more of blocks 784, 786, and 790. Thus, in some embodiments, the system can initiate a flushing procedure after receiving a flush instruction without making prompts to a user, and in some embodiments, only a single syringe actuation is used.

Figure 48:
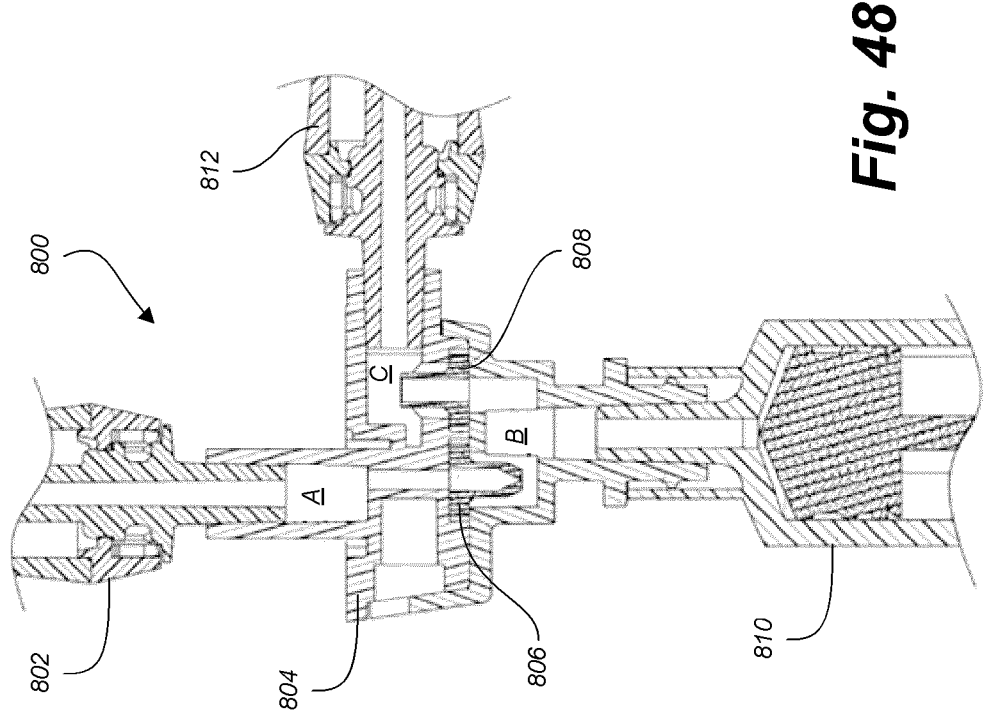
FIG. 48 is a cross sectional view of a connector showing various portions of a fluid pathway through the connector.

Flushing of the connector will be further described in connection with FIG. 48, which is a cross sectional view of a connector 800, which can be similar to, or the same as, other connectors disclosed herein. The connector 800 can have a fluid pathway portion A that includes the fluid pathway through the source connector portion 802 and into the connector body 804 up until the source check valve 806. A fluid pathway portion B can be the area between (e.g., below) the source check valve 806 and the target check valve 808, and extending into the syringe 810. The fluid pathway portion C can extend from the target check valve 808 out through the target connector portion 812.

During a first syringe actuation (block 788), the syringe plunger can be withdrawn so that air can be drawn through the fluid pathway portions A and B and into the syringe 810. The air can push the fluid from the pathway portion A down towards the syringe 810. Thus, once the syringe plunger is retracted, fluid pathway portions A and B can be filled with air and substantially no fluid. In some embodiments, Gravity can cause the fluid to move to the bottom of the syringe 810 with air positioned above the fluid. When the plunger is driven forward, the air can be driven up into the connector body 804 followed by the fluid. The air driven up from the syringe 810 can pass through the target check valve 808 and drive fluid in the fluid pathway portion C out through the target connector portion. Once the air is expelled from the syringe 810, the fluid that was below the air in the syringe 810 can be pushed up into the connector body 804. Thus, when the plunger is fully advanced after the first syringe actuation (block 788), the fluid pathway portion B can at least partially be filled with the fluid that had been in the syringe 810 below the air. In some embodiments, the fluid pathway portion B can be substantially filled with that fluid, and in some case the fluid expelled from the syringe 810 can extend into the fluid pathway portion C. Fluid pathway portion A can have substantially no fluid therein at this stage.

At block 790, the syringe 810 can be actuated additional time(s). Additional air can be drawn through the fluid pathway portions A and B into the syringe 810 as the plunger is retracted. The fluid in pathway portion B can drop into the syringe 810 and can be positioned below the air. Fluid that had crossed the target check valve 808 into pathway portion C can remain in pathway portion C as the plunger is retracted. Then, when the plunger is advanced, first the air and then the fluid can be pushed from the syringe 810 into the connector body 804. The air can be driven through the target check valve 808 and through the fluid pathway portion C, thereby pushing the fluid from fluid pathway portion C out of the connector 800 and into a target container. The fluid that had been below the air in the syringe 810 can be pushed up into fluid pathway portion B. In some embodiments, after the second syringe actuation, the volume of fluid left in fluid pathway portion B can be smaller than the volume of fluid pathway portion B so that none or substantially none of the fluid crosses the target check valve 808 into fluid pathway portion C. Thus, in some embodiments, additional syringe actuations can merely cause the residual fluid in fluid pathway portion B to move to and from the syringe 810 without driving additional fluid out through fluid pathway portion C. In some embodiments, it may be acceptable for an amount of residual fluid to remain in the fluid pathway portion B after the flushing process.

In some embodiments, the connector 800, the syringe 810, and/or other components can be reoriented to facilitate flushing of connector 800. For example, by placing the connector 800 and/or the syringe 810 upside down during the syringe actuation (block 788 or block 790), the fluid can be driven out of the syringe 810 before the air. Thus, after the plunger is advanced, the fluid pathway portion B can be filled with air and substantially no fluid. Fluid pathway portions A and C can also be filled with air and substantially no fluid in this embodiment. Thus, in some embodiments, system can be configured to reorient the connector 800, the syringe 810, and/or other components during some or all of the fluid flush process. In some embodiments, the system can have a rotation mechanism that allows or causes the connector 800 and/or the syringe 810 to be rotated to an upside down configuration. The system can, in some embodiments, prompt the user to reorient the connector 800 and/or the syringe 810. In some embodiments, the flushing can be performed by a user after disconnecting the connector 800 and/or the syringe 810 from the system.

In some embodiments, the connector 800 can be configured differently than as shown so that the syringe 810 is oriented to allow fluid to be driven out of the syringe 810 before air. For example, the syringe 810 can be oriented upside down from the orientation shown in FIG. 48 so that the plunger is above the syringe outlet. In some embodiments, the connector 800 can be similar to that shown in FIG. 48 but with the entire connector 800 oriented upside down from the orientation shown. In some such embodiments, the source container can be connected to the source connector portion 802 by a tube so that the source container portion (e.g., vial) can be positioned with its outlet facing downward. In some embodiments, the connector 800 can be similar to that shown in FIG. 48 but the syringe 810 can be connected to the connector body 804 by a length of tubing so that the syringe can be oriented with the plunger facing upward.

In some embodiments, the addition of tubing between the connector 800 and the syringe 810 or the source container (e.g., vial) can introduce additional volume to the fluidics of the system, which can be undesirable in some cases, for example leading to additional fluid waste. Thus, as shown semi-schematically in FIG. 49, in some embodiments, the connector 900 can be configured to have both the source connector portion 902 and the syringe 910 extending upwardly from the connector body 904. Thus, when flushing the connector 900, in some embodiments, only a single syringe actuation is used to substantially clear the fluid pathway portions A, B, and C of fluid.

Figure 49:
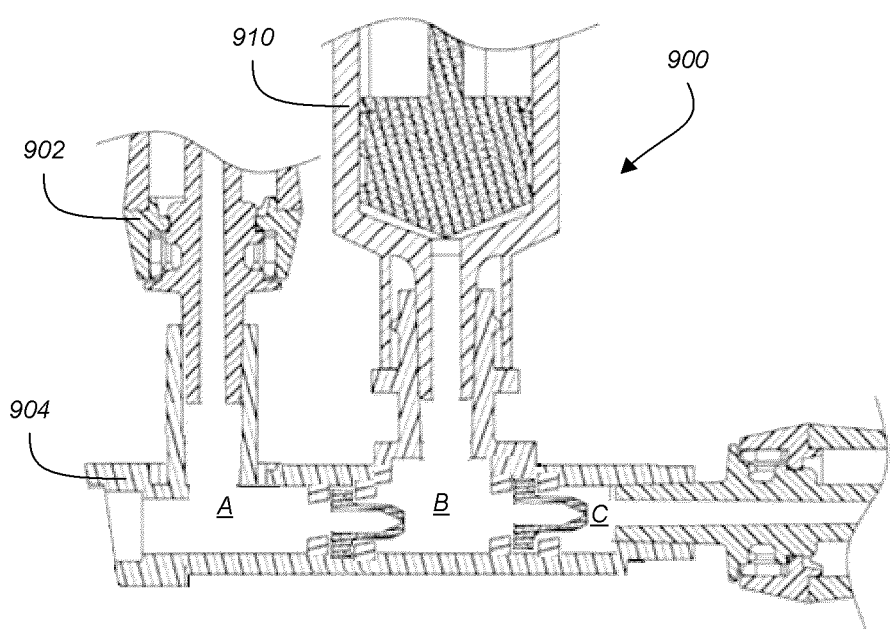
FIG. 49 is a cross sectional view of another example embodiment of a connector.

In some embodiments, the system can be configured to accommodate the Syringe being oriented upwardly, as shown in FIG. 49 for example. For example, in some embodiments, when transferring fluid, a pocket of air can be maintained in the syringe (e.g., about equal to the volume of fluid pathway portion B), and the system can adjust the fluid transfer calculations accordingly. Also, when performing an initial transfer of fluid through a dry connector, the system can be configured to prime the connector by actuating the syringe plunger by a predetermined amount that is configured to position the leading edge of the fluid at a specific location (e.g., at or near the entrance to the IV bag or IV bag assembly). If the syringe is oriented upwardly (as shown in FIG. 49), air that is drawn into the syringe can exit after the initial fluid that is drawn into the syringe resulting in air being located behind the leading edge of the fluid. In some embodiments, the priming process can be modified to accommodate for the air behind the initial portion of fluid. For example, in some embodiments, the priming process can push the initial portion or fluid into the target container and drive the leading edge after the air up to the specified priming location. The volume of the initial portion of fluid can be calculated from the known volumes of the fluid pathway portions and by the amount that the syringe was actuated. The system can subtract the volume of the initial portion of fluid that was pushed into the target container from the initial fluid transfer volume.

In some embodiments, the system can omit the priming process and can merely adjust the calculations for an initial fluid transfer to accommodate for the air that will be pushed in to the target container from the dry connector. For example, when the system receives a fluid transfer command, if the system determines that the connector has not been primed, the system can initiate the fluid transfer process, but add a predetermined additional volume to the transfer to accommodate for the air that will be pushed into the target container. In some embodiments, the volume for one or both of the first two syringe actuations can be affected. For example, the first syringe actuation can transfer the initial portion of fluid towards or into the target container, and the initial portion of fluid can be followed by air, as described above, when the syringe is oriented upwardly. Thus, in some embodiments, the second syringe actuation can drive the remaining air into the target connector along with fluid behind the air portion. In some embodiments, subsequent syringe actuations (e.g., after the first two actuations) can transfer fluid into the target container without pushing substantially any air into the target container. In some embodiments, a pocket of air can remain in the syringe (e.g., adjacent to the plunger surface), but is not transferred substantially beyond fluid pathway portion B. This air pocket can facilitate flushing of the connector once fluid transfers are complete by preventing fluid from remaining trapped in fluid pathway portion B during flushing.

Figures 50, 51:
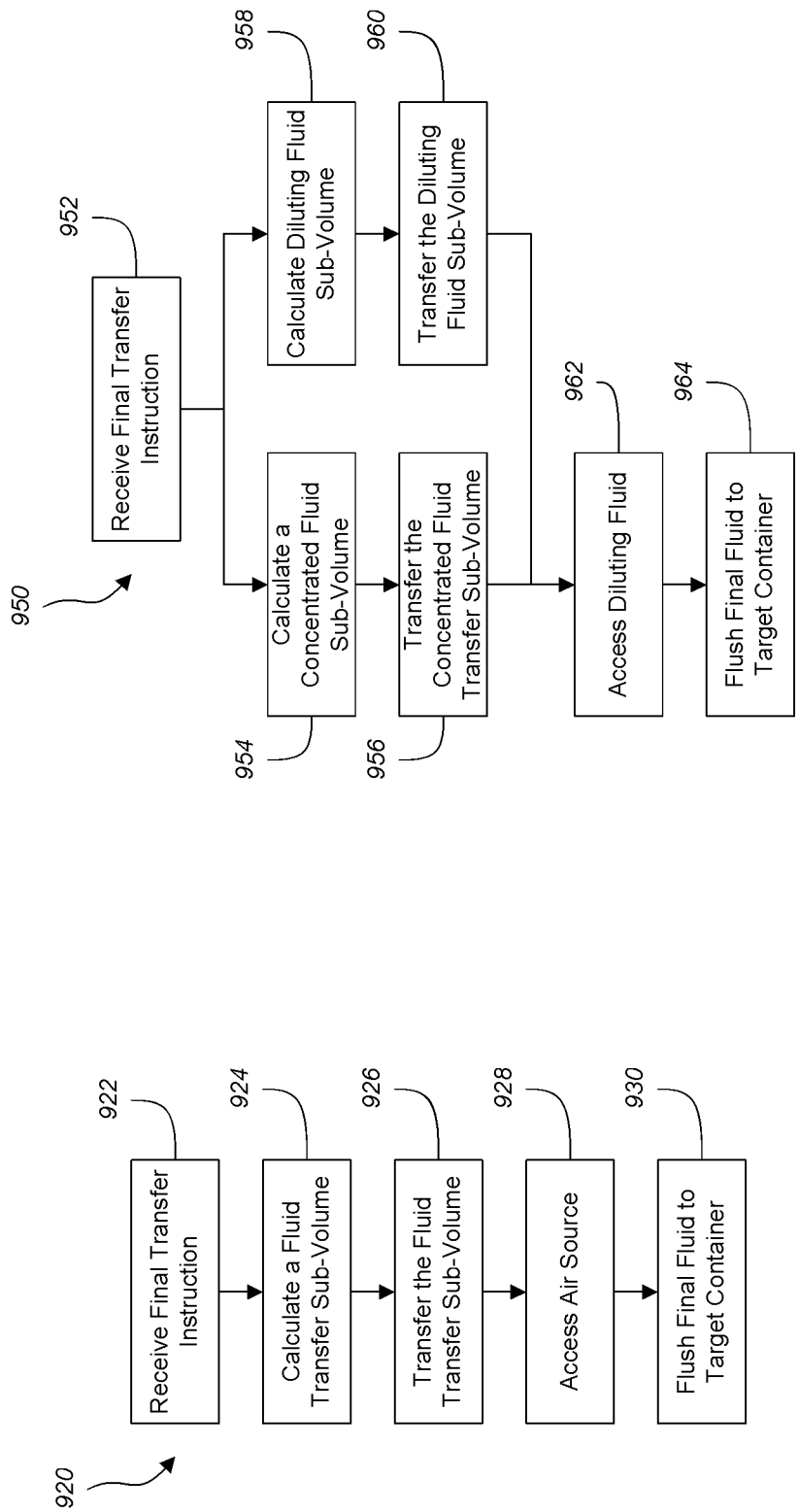
FIG. 50 is an example embodiment of a method for transferring fluid that includes flushing a connector.
FIG. 51 is another example embodiment of a method for transferring fluid that includes flushing a connector.

In some embodiments, the system can be configured to flush the fluid from the connector into a target container as the final volume of fluid for a fluid transfer. Thus, in some embodiments, the user does not need to change the target container when flushing the connector. FIG. 50 is a flow chart showing an example embodiment of a method for flushing the connector. At block 922, the system can receive a final fluid transfer instruction, which can be received from a user (e.g., via a user interface) or by an outside system (e.g., via a data connection). For example, the user interface can have a button that allows the user to specify that a particular fluid transfer will be the last performed before removing the source container and/or other components. The final transfer instruction can also include an indication of the volume of fluid to be transferred.

At block 924, the system can calculate a fluid transfer sub-volume, for example, by subtracting a known or calculated flush volume from the volume to be transferred. At block 926, the system can transfer the sub-volume of fluid from the source container to the target container as described herein, and the system can stop the fluid transfer once the sub-volume has been transferred. At block 928, the system can access an air source. For example, the system can prompt the user to remove the source container (e.g., vial) and attach an air source attachment (e.g., attachment 770). At block 930, the system can flush the fluid out of the connector as described herein to drive the flushed fluid into the target container (e.g., IV bag). In some embodiments, some air can be driven into the target container along with the fluid. The volume of the fluid flushed into the target container can be predetermined or calculated based on the known volumes of the portions of the fluid pathway through the fluidics system. The fluid transfer sub-volume, which is driven into the target container prior to the flush process, and the flushed fluid volume can add to substantially equal the specified volume of fluid to be transferred in the received instructions.

In some embodiments, saline or water or other liquid can be used to flush the connector. Thus, the embodiments described herein can be modified to use a flushing liquid instead of air. For example, in the method 750 of FIG. 45, the user can remove the source container at block 756 and attach a fluid connection to a flushing fluid at block 760. For example a saline bag can used, and an outlet tube from the saline bag can have a connector at the end that is configured to engage the source connector portion (e.g., 802 in FIG. 48). Although several embodiments discuss flushing with saline, other fluids can be used (e.g., water or a cleaning solution). In the method 780 of FIG. 47, the system can prompt the user to attach a saline (or other fluid) source at block 784. In FIG. 50, the method 920 can access a flushing fluid source at block 928, which can include prompting a user to attach a flushing fluid source to the source connector portion.

In some embodiments, the flushing fluid can be used to dilute the transferred fluid. For example in some embodiments, the method 920 of FIG. 50 can be modified as mentioned to provide access to a diluent fluid (e.g., saline) at block 928. The system can transfer a specified or calculated amount of saline through the connector to attain the specified concentration for the transferred fluid. Thus, the final portion of the concentrated fluid can be flushed through the connector by the diluent fluid and the diluent fluid transfer can continue until the desired concentration is reached.

FIG. 51 is a flowchart showing a method 950 for transferring a diluting fluid for diluting a concentrated fluid to a specified concentration. At block 952, the system can receive a final fluid transfer instruction in a manner similar to that described for block 922. The instructions can include a specified volume for the concentrated fluid and a specified volume for the diluent to be transferred, or the instructions can include a specified concentration and amount for the final mixture and the volumes for the concentrated fluid and diluent can be calculated by the system. At block 954 the system can calculate a sub-volume for the concentrated fluid, for example by subtracting a volume for the amount of the concentrated fluid expected to be flushed from the connector during a flush procedure from the total volume of the concentrated fluid to be transferred. At block 956, the system can transfer the sub-volume of the concentrated fluid from the source container to the target container as described herein.

At block 958, the system can calculate a diluting fluid sub-volume, for example, by subtracting a diluting fluid flush volume from the total diluting fluid volume to be transferred. At block 960, the system can transfer the diluting fluid sub-volume from a diluting fluid source container to the target container. In some embodiments, the transfer of the concentrated fluid sub-volume, at block 956, can be performed by a first fluid transfer station and the transfer of the diluting fluid sub-volume, at block 960, can be performed by a second fluid transfer station. In some cases, the transfer of the concentrated fluid sub-volume, at block 956, can be performed simultaneously with the transfer of the diluting fluid sub-volume, at block 960.

At block 962, the system can access the diluting fluid through the connector used to transfer the concentrated fluid. For example, the system can prompt the user to change the connections so that the diluting fluid source (e.g., saline bag) is attached to the source connector portion of the connector that had been used to transfer the concentrated fluid. At block 964, the system can flush the remaining concentrated fluid out of the connector using the diluting fluid. The amount of diluting fluid pushed through the connector can be configured so that the diluting fluid flush volume used in the calculation of block 958 is pushed into the target container along with the remaining concentrated fluid. In some embodiments, more fluid than the diluting fluid flush volume is actually drawn into the connector because diluting fluid can be left in the connector after the flush is completed. Thus once the flush is completed, the concentrated fluid sub-volume and the concentrated fluid flush volume can add to provide the amount of concentrated fluid needed to attain the desired amount and concentration for the mixture. Similarly, once the flush is completed, the diluting fluid subvolume and the diluting fluid flush volume can add to provide the amount of diluting fluid needed to attain the desired amount and concentration for the mixture.

Figure 52:
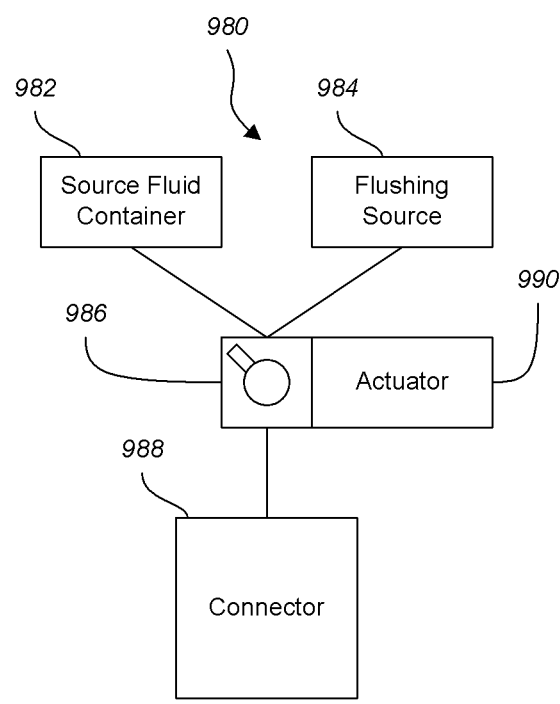
FIG. 52 is a schematic view of an example embodiment of a source switching system.

In some embodiments, the system can be configured to automatically access air or a flushing fluid for flushing the connector. For example, a source switching system 980 is shown schematically in FIG. 52. The system 980 can include a source fluid container 982 (e.g., a vial) and a flushing source 984. The flushing source 984 be a source of a flushing fluid (e.g., saline, water, or a cleaning solution), or the flushing source 984 can provide access to air for flushing a connector. For example, an air inlet can be provided by a one way valve or filter. A fluid switch 986 can provide fluid communication to the source fluid container 982 or the flushing source 984. The fluid switch 986 can be a stopcock or other switch that can be actuated between at least two configurations. A first configuration can open a fluid pathway between the source fluid container 982 and the connector 988 while closing the fluid pathway between the flushing source 984 and the connector. The second configuration can open an fluid pathway between the flushing source 984 and the connector 988 while closing the fluid pathway between the source fluid container and the connector 988. The system can include an actuator 990 configured to toggle the actuator 986 between the first and second configurations based on input received from the controller of the system.

The embodiments discussed herein relating to flushing the connector can be modified to use the source switching system 980 or other configuration that allows the system to automatically access air or a flushing fluid for flushing the connector. For example, in the method 750 of FIG. 45, the system can actuate a fluid switch at block 760 to provide access to air or to a flushing fluid. In some embodiments, block 756 can be omitted so that the user does not remove the fluid source container (e.g., vial).

For the method 780 of FIG. 47, the system can actuate a fluid switch before actuating the syringe pump at block 788, thereby providing access to air or to a flushing fluid. In some embodiments, the block 784 can be omitted so that the system does not prompt the user regarding an air source attachment. As discussed above, in some embodiments, block 786 can also be omitted so that the system does not prompt the user regarding the target container, for example if the same target container is to be used during the fluid transfer and the flush. Also as mentioned above, in some embodiments, block 790 can be omitted so that the flush is performed in a single syringe actuation.

For the method 920 of FIG. 50, the system can actuate a fluid switch at block 928 to provide access to air or to a flushing fluid. For the method 950 of FIG. 51, the system can actuate a fluid switch at block 962 so that the connector being flushed is in communication with the diluting fluid source.

Figure 54:
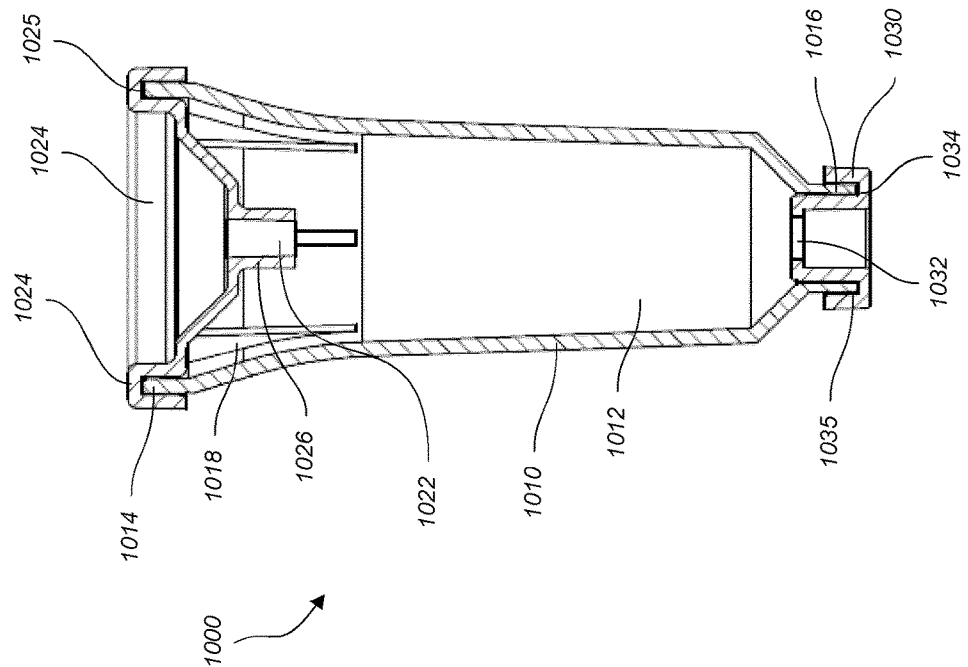
FIG. 54 shows a cross section of the reservoir container from FIG. 53.
Figure 53:
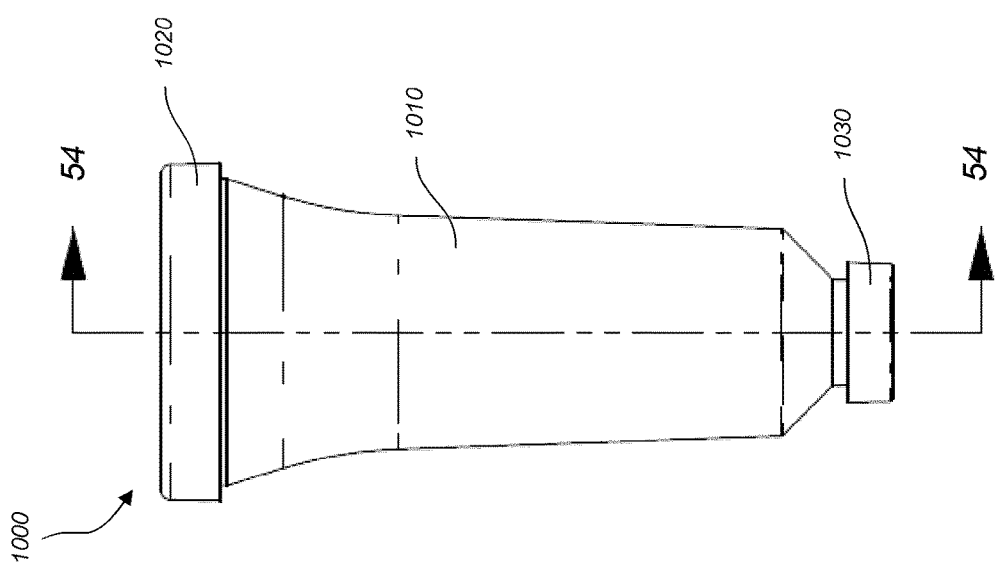
FIG. 53 shows an example embodiment of a reservoir container.

FIGS. 53 and 54 illustrate an embodiment of a reservoir container 1000 that can be used with the fluid delivery systems discussed herein. The reservoir container 1000 comprises a reservoir body 1010, an upper end cap member 1020, and a lower end cap member 1030. The reservoir body has an upper opening 1014 and a lower opening 1016. The reservoir body 1010 has a substantially cylindrical shape that forms a cavity 1012. In the illustrated embodiment, the reservoir body 1010 generally decreases in diameter, or cross-sectional area, from the upper opening 1014 down to the lower opening 1016. At the upper opening 1014, a portion of the body has a generally constant diameter, or cross-sectional area, that is sized and configured to couple with the upper end cap member 1020. At the lower opening 1016, a portion of the body has a generally constant diameter, or cross-sectional area, that is sized and configured to couple with the lower end cap member 1030. The interior wall of the reservoir body 1010 can have a plurality of struts or supports. The supports 1018 provide additional structural integrity to the reservoir body 1010. The reservoir body 1010 is formed from a flexible material, such as a silicone rubber or a flexible polymeric material. The reservoir body 1010 can be compressed laterally, causing the volume of the internal cavity to decrease. The reservoir body 1010 can formed from a material that can be elastically deformed and still generally maintain the original shape of the body 1010 after rebounding from the deformation. The reservoir body can be formed from a substantially transparent material.

The upper end cap member 1020 comprises a upper end cap wall 1024 and a hole 1022. The wall 1024 angles downward and a tube 1026 extends downwards into the cavity 1012 of the reservoir body 1010. The hole 1020 is substantially positioned about a center axis of the upper end cap member 1020, which is substantially concentric with a center axis of the reservoir body. The length of the tube is sized and configured to engage a fluid connector (e.g., a Spiros® closeable male connector manufactured by ICU Medical, Inc., of San Clemente, Calif.). The wall 1024 forms an upper mounting recess 1025. The mounting recess 1025 is sized and configured to engage the upper opening 1014 of the reservoir body 1010. The upper end cap member 1020 can be constructed from a rigid material such as polycarbonate or other polymeric materials.

The lower end cap member 1030 comprises a lower end cap wall 1034 and a hole 1032. The wall 1024 forms an lower mounting recess 1035. The mounting recess 1035 is sized and configured to engage the lower opening 1016 of the reservoir body 1010. The hole can be configured to engage a fluid connector, such as a closeable male connector, or other appropriate fixture. The lower end cap member 1030 can be constructed from a rigid material such as polycarbonate or other polymeric materials.

The reservoir body 1010 is configured to have a fluid tight seal with the upper end cap member 1020 and the lower end cap member 1030. The openings 1014, 1016 of the reservoir body can be permanently coupled within the upper mounting recess 1025 and the lower mounting recess 1035. An adhesive or other suitable manner to form a fluid tight connection between the reservoir body and the end cap members 1020, 1030.

The reservoir body can have many different shapes, such as generally spherical, generally conical, generally rectangular, generally cubical, etc. For example, the outer diameter of the reservoir body 1010 can be greater than the outer diameter of the end cap member.

Figure 56:
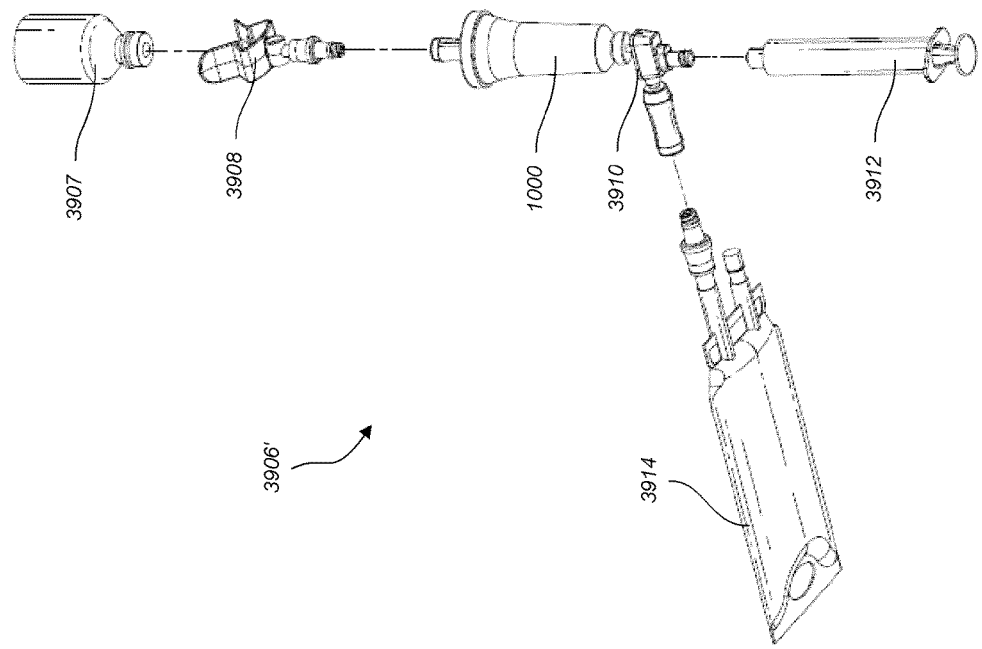
FIG. 56 is an exploded view of the fluidics assembly of FIG. 55.
Figure 55:
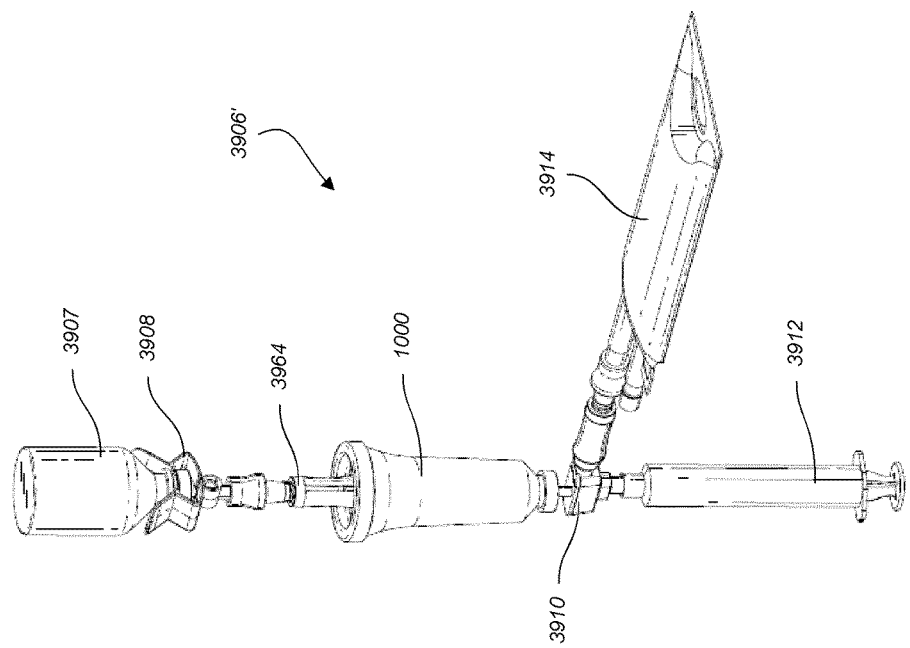
FIG. 55 is a perspective view of an example embodiment of a fluidics assembly that can be used to transfer fluid.

FIGS. 54 and 55 illustrate an embodiment of the reservoir container coupled to a fluidics assembly 3906'. FIG. 55 is a perspective view of a fluidics assembly 3906' that can be used with the first fluid transfer station 218*a*. FIG. 56 is a perspective exploded view of the fluidics assembly 3906 from a different angle than that shown in FIG. 55. The fluid assembly 3906' can be used to transfer precise amounts of fluid from a vial 3907 to an IV bag 3914. The fluidics assembly 3906' includes a vial 3907, a vial adapter 3908 configured to provide fluid communication with the fluid (e.g., chemotherapy drug or other medication) contained within the vial 3907, a reservoir container 1000, a syringe 3912, an IV bag assembly 3914, and a connector 3910 for directing fluid from the reservoir container 1000 into the syringe 3912 and from the syringe 3912 toward the IV bag assembly 3914. The reservoir container 1000 can be used to transfer fluid from the vial 3907 via the vial adapter 3908 to the reservoir container 1000. A connector 3964 can be fixedly coupled to the upper end cap member 1020 of the reservoir container 1000. The lower end cap member 1030 can be fixedly coupled to the connector 3910. In some embodiments, the fluidics assembly 3906' can have features similar to, or the same as, those of the other fluidics systems disclosed herein. For example, the connector 3910 can be the same or substantially similar to the connector 226a, also discussed herein.

Figure 58:
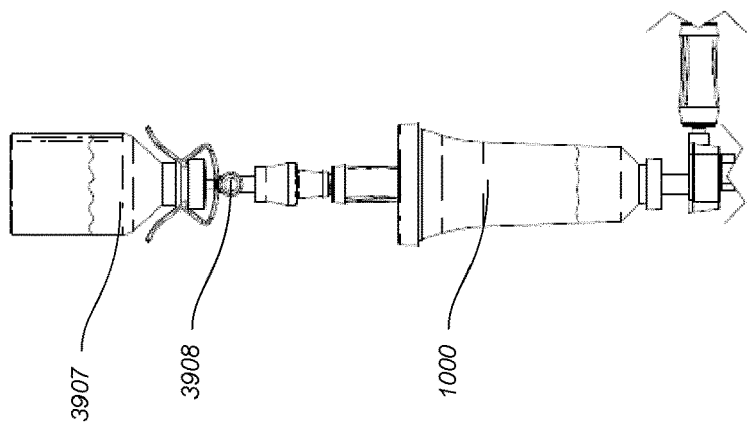
FIGS. 57 and 58 illustrate usage of a reservoir container in a fluidics assembly.
Figure 57:
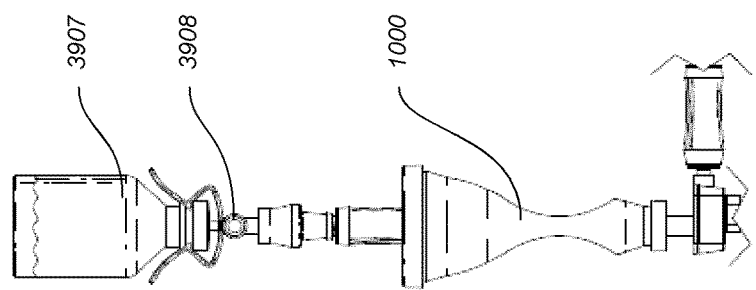

FIGS. 57 and 58 illustrate an example of usage of the reservoir container 1000 in the fluidics assembly 3906'. FIG. 57 there is fluid contained within the vial 3907. To transfer fluid from the vial to the reservoir container 1000, the reservoir container 1000 is compressed as shown. When the reservoir container 1000 is compressed, the volume of the internal cavity 1012 is decreased, thereby forcing air out of the internal cavity and into the vial. When the reservoir container is released as shown in FIG. 58, a vacuum is created causing fluid to be drawn from the vial 3907 to the cavity of the reservoir container 1000. In some embodiments, the vial adapter 3908 can be configured to allow air to enter the vial 3907 via the vial adapter 3908, thereby substantially equalizing pressure in the vial 3907 as fluid is drawn out. The process of compressing and releasing the reservoir container 1000 can be repeated until substantially all of the fluid from the vial 3907 has been transferred to the reservoir container 1000. The fluidics assembly 3906' can be configured to allow the vial 3907 and vial adapter 3908 to be replaced when the vial runs out of fluid without requiring the replacement of the reservoir container 1000, connector 3910, or syringe 3912. The vial can be replaced with another vial. The fluid contents of the new vial can be transferred to the reservoir container 1000 by compressing and releasing the reservoir container 1000. The reservoir container 1000 can be sized such that it can hold the contents of more than one vial.

Figure 59:
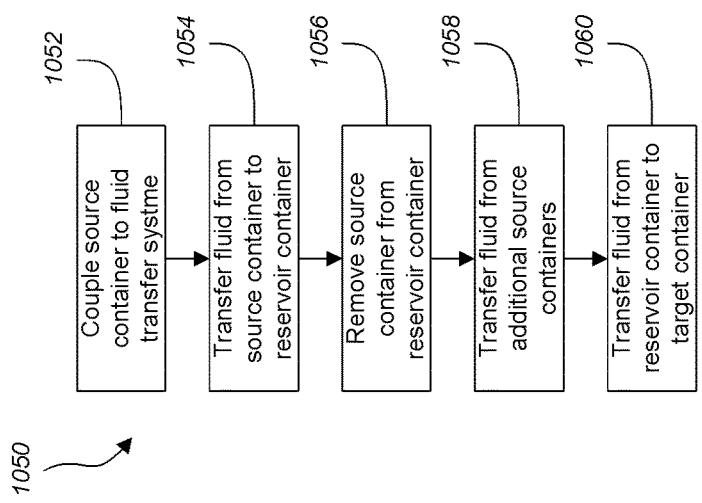
FIG. 59 is an example embodiment of a method for using a reservoir container in a fluidics assembly.

FIG. 59 illustrates a method for transferring fluid from reservoir container to a target container with a fluid delivery system 1050, such as the system 200. The fluid delivery system can have a fluidics assembly with features similar to, or the same as, those of the other fluidics systems disclosed herein. At block 1052, a source container (e.g., a medical vial or other suitable container such as a bag, a bottle, or a vat, etc.) containing a fluid (e.g., chemotherapy drug or other medical fluid) is coupled to the fluid transfer system. The source container is configured to be in fluid communication with the reservoir container 1000.

At block 1054, fluid is transferred from the source container to the reservoir container 1000. In some embodiments, the fluid is transferred by compressing and releasing the reservoir container. The process of transferring the fluid to the reservoir container 1000 is repeated until the source container runs out of fluid. When the reservoir container 1000 is compressed, the volume of the internal cavity 1012 is decreased, thereby forcing air out of the internal cavity and into the source container. When the reservoir container is released, a vacuum is created thereby drawing fluid out of the source container and into reservoir container 1000. The process of compressing and releasing the reservoir container can be performed by a lab technician. In some embodiments, the process can be performed by an automated mechanical system.

At block 1056 the source container is removed from the fluid transfer system. In some embodiments, the fluidics system can be used to transfer fluid while retaining substantially entirely, or entirely, all of the fluid within the system, permitting the fluid transfer to occur in a substantially entirely, or entirely, closed system. The fluid delivery system can thereby reduce or eliminate the risk of injury, waste, or damage caused by liquid or vapor leakage when connecting and disconnecting the components of the fluidics system.

At block 1058 the process of transferring fluid as described in blocks 1052 and 1054 can be repeated to transfer additional fluid to the reservoir container 1000. The reservoir container 1000 can be configured to hold the contents of one or more source containers. The process can be repeated until the desired amount of fluid has been transferred to the reservoir container 1000 from the source containers. In some embodiments the reservoir container can be configured to hold at least the amount of fluid that will be transferred to a target container (e.g., an IV bag, an elastomeric pump, a syringe, or other suitable container) in a typical dosage range used for patient treatment of a particular type of medicinal fluid.

At block 1060 the fluid is transferred from the reservoir container 1000 to the target container. The fluid can be transferred from the reservoir container to the source container using the fluid delivery system and procedures for transferring fluid from the source container to the target as discussed herein.

The process of transferring the fluid from the one or more source containers to the reservoir container prior to transferring the fluid to the target container can reduce the time that is required to fill the target container. For example, the reservoir container can be of a sufficient size so that it does not need to be refilled in order to completely fill the target container. Additionally, in some embodiments, some or all of the steps associated with changing source containers can be performed at the same time and a lab technician is not required to attend to the fluid delivery system as it is filling the target container. Additionally, the reservoir container can reduce the likelihood that an air bubble is drawn into the fluidics system during operation because the source containers are not changed, or are changed less frequently during the transfer of fluid from the source container to the target container.

Figure 60:
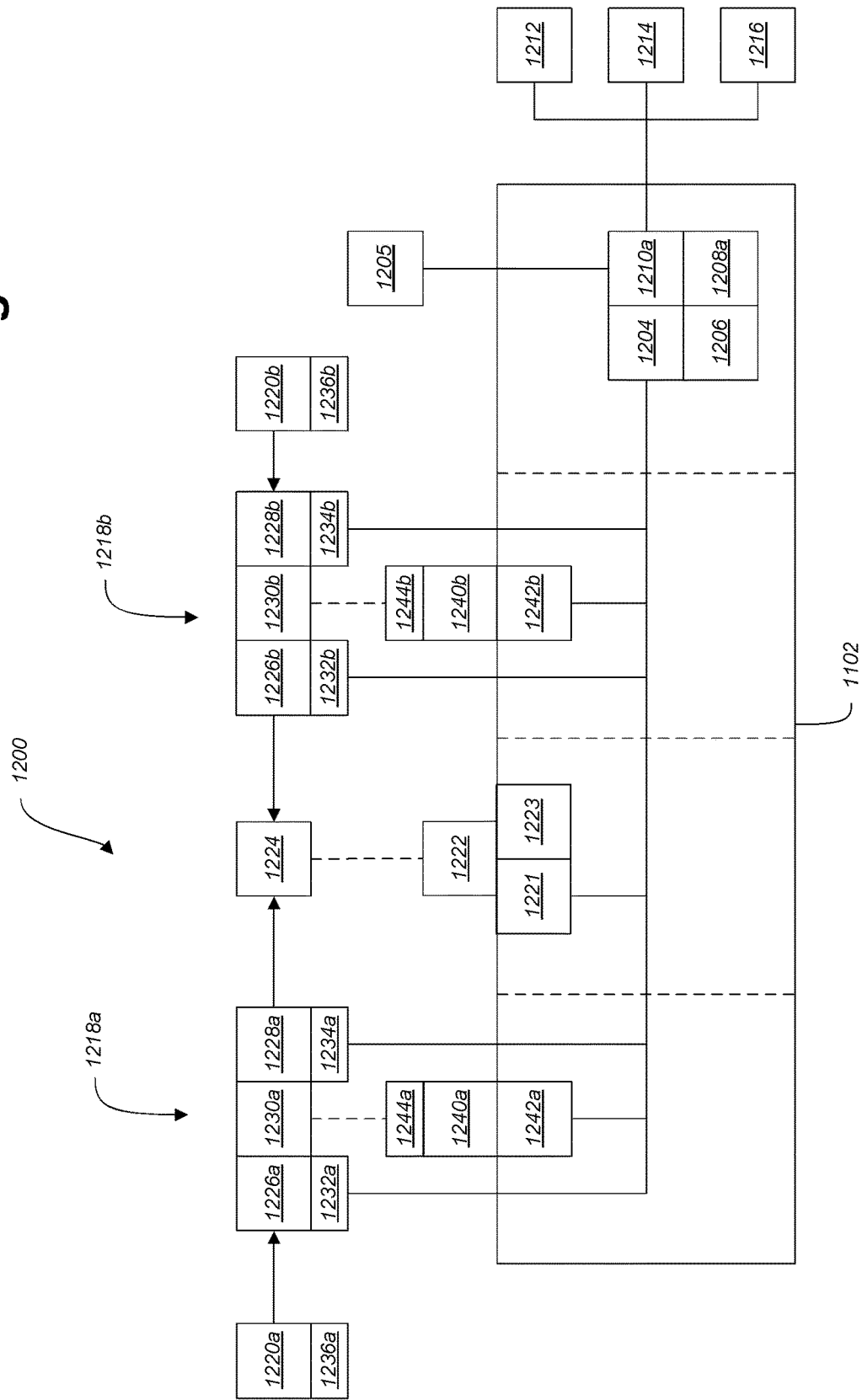
FIG. 60 schematically shows an example embodiment of an automated system for transferring fluid.

FIG. 60 schematically shows an embodiment of an automated fluid transfer system 1200. The system 1200 comprises one or more fluid transfer stations 1218a-b, a destination sensor, such as an end volume sensor or a weight sensor 1222, and a controller 1204. Although in the embodiment shown, the components are all contained within the housing 1202, a variety of other configurations are possible. For example, the system 1200 can include one or more housings 1202 enclosing components of the various systems. In some embodiments, each component grouping can have a separate housing (as illustrated by the dashed lines within the housing 1202). In some embodiments the controller 1204 can be contained within the same housing as the first fluid transfer station 1218a. In some embodiments there is a single fluid transfer station 1218a. In some embodiments there can be a plurality (e.g., a first and a second) fluid transfer stations 1218a-b. In some embodiments the destination sensor 1222 can be in a different housing than the fluid transfer stations 1218a-b and the controller 1204. In some embodiments, the controller 1204 can be external to the housing 1202, and can be, for example contained within a second housing, which may also contain the user interface 1208.

The system 1200 has a controller 1204 and a memory module 1206. The controller 1204 can be configured to control the operation and functions of the fluid transfer stations 1218a-b and the destination sensor 1222. The system 1200 can also include a user interface 1208, which can be, for example, external to the housing 1202. The user interface 1208 can also be integrated into the housing 1202 in some cases. The user interface 1208 can include, for example, a display, a keypad, and/or a touch screen display. The user interface 1208 can be configured to receive instructions from the user, for example, regarding the amounts of fluid to be transferred and the types of fluids to be transferred. The user interface can also be configured to provide information to the user, such as error messages, alerts, or instructions (e.g., to replace an empty vial). In some embodiments, the system 1200 can include a communication interface 1210 configured to receive information (e.g., instructions) from a remote source such as an external controller 1212, a terminal (such as a computer) 1214, or an automated management system (such as a hospital information system (HIS)) 1216, etc. In some embodiments, the communication interface can also send information (e.g., results or alerts) to the remote source. The communication interface can include one or more connection types and can be configured to allow connectivity to multiple remote sources at once. In some embodiments, the system 1200 does not include a communication interface 1205 and does not communicate with a remote source.

The destination sensor 1222 can include a communication interface 1221 that can communicate with the controller 1204. In some embodiments a weight sensor 1222 can communicate with the controller using wireless communication. In some embodiments a weight sensor 1222 can be physically connected to the controller 1204 using a standard communication interface (e.g., RS232, USB, etc.). The controller 1204 can receive information (e.g., measurements, current state of operation, etc.) and provide commands (e.g., zeroing the weight sensor) to the weight sensor 1220 through the communication interface 1221. In some embodiments the weight sensor 1222 can include a user interface 1223. The user interface can provide a visual indication of weight, and other information. In some embodiments the weight sensor 1222 can receive commands or instructions through the user interface 1223 from a user.

The destination sensor 1222 is used to determine the amount of fluid transferred from the source container 1220a-b to the target container 1224. The destination sensor 1222 outputs the weight of the fluid transferred to the target container to the controller 1204. Prior to transferring fluid, the scale can be programmatically zeroed in order to compensate for the weight of the target container 1224. For example, a base weight can be assigned as "zero" fluid weight (i.e., equivalent to the weight of the inherent scale weight and/or equivalent to the inherent scale weight plus a first fluid weight, and/or equivalent to the weight of the target container). The scale can then determine the relative weight of the fluid transferred to the target container 1224 beyond the base weight.

In some embodiments, the destination sensor 1222 is a scale that is capable of receiving weight information and electronically providing the information to the controller 1204. The scale can be located in a separate housing 1202. In some embodiments, the scale can have a substantially flat weighing surface for the target container. In some embodiments (not illustrated) the scale can be a hanging scale.

In some embodiments, the fluid transfer station can include a positive displacement pump, such as a peristaltic pump, 1240a-b, a motor 1242a-b and a fluidics assembly. The positive displacement pump 1240a-b can be used to pump fluid from a source container 1220a-b to a target container 1224. The fluid is transferred via a hose 1228a-b fitted inside a pump mounting interface 1244a-b. A rotor with a number of lobes rotates and compresses the hose 1228a-b progressively along an advancing portion of the hose. As the lobe passes a particular portion of hose, such portion of hose rebounds to substantially its original shape and internal volume. As the rotor turns, the part of hose 1228a-b under compression is pinched, thus, displacing fluid and forcing the fluid to move forward through the tube. The speed of the rotation of the rotor, the number of lobes, and the material properties of the hose influence the flow rate of the fluid through the system. The flow rate of the fluid transfer can be controlled by varying the speed of the pump 1240a-b. The motor 1242a-b operating the pump 1240a-b can run at variable speeds. The peristaltic pump 1240a-b can be configured to operate at a low pressure. The pressure generated by the pump 1240a-b can be sufficiently low, such that it is below a threshold at which the connector 1230a-b will not leak if the pump is operating and the connector 1230a-b is not connected to the target container.

The operations of the pump can be controlled by the controller 1204. In some embodiments, the housing 1202 incorporating the pump can have a touch screen that allows commands to be provided to the controller 1204. For example, a user can instruct the pump to transfer a specific amount of fluid to the target container. In some embodiments the commands can be received from an external source such as a network computer. The controller 1204 can operate the pump at variable speeds by controlling the speed of the motor. The controller 1204 can control that rate at which the rotor is spinning, which, in turn, controls the fluid flow rate. In some embodiments, the computer can use an algorithm to reduce the speed of the motor as the amount of fluid approaches the desired amount of fluid in the target container in order to increase accuracy.

Each fluid transfer station 1218a-b can have a fluidics assembly that includes a first connector 1226a-b, a hose 1228a-b, and a second connector 1230a-b. The hose 1228a-b can be formed from a compressible material (e.g., silicone rubber, and other elastomeric materials). The hose 1228a-b is configured to be inserted within the mounting interface 1244a-b of the peristaltic pump 1240a-b (as illustrated by the dashed line) in order to facilitate the transfer of fluid between the source container 1220a-b and the target container 1224. Some embodiments can be assembled from different types or portions of hose. In some embodiments, the hose 1228a-b can be formed from a single material. In some embodiments, the hose is formed with an elastomeric portion and other portions formed from polymeric materials. The first and second connectors 1226a-b, 1230a-b are fixedly coupled to the hose 1228a-b at opposite ends and are not configured to be removable from the hose. The first connector 1226a-b is configured to connect to the source container 1220a-b. In some embodiments, one or more pairs of male and female fluid connectors configured to be attached to each other to selectively permit the passage of fluid between the source container 1220a-b and the target container 1224. The connectors can be detached or disconnected, for example, so that the target container 1224 can be removed once the fluid has been transferred. In some embodiments, the connectors can be configured to automatically close when disconnected from a corresponding connector, thereby preventing fluid from escaping when the connectors are detached. Thus, the fluid transfer system 1200 can be used to transfer fluid while retaining substantially entirely, or entirely, all of the fluid within the system, permitting the fluid transfer to occur in a substantially entirely, or entirely, closed system. The fluid transfer system 1200 can thereby reduce or eliminate the risk of injury, waste, or damage caused by liquid or vapor leakage when connecting and disconnecting the components of the fluid transfer system 1200.

Each transfer station 1218*a-b* can include a fluid source container 1220*a-b*, which can be, for example, a medical vial or other suitable container such as a bag, a bottle, or a vat, etc. Although many embodiments disclosed herein discuss using a vial as the source container, it will be understood the other containers can be used even when not specifically mentioned. In some embodiments, each of the source containers 1220*a-b* can contain a unique fluid, providing a variety of fluids that the user can select for transfer. In other embodiments, two or more of the source containers 1220*a-b* can contain the same fluid. In some embodiments, the source containers 1220*a-b* include bar codes that identify the types of fluid contained therein. The bar codes can be scanned by a bar code scanner 1205 that is in communication with the controller 1204 and/or the memory 1206 (e.g., via the communication interface 1210) so that the identities of the fluids contained by source containers 1220*a-b* can be stored within the memory module 1206. In some embodiments, the fluid transfer stations 1218*a-b* are configured to transfer precise amounts of fluid from source containers 1220*a-b* to a target container 1224, which can be, for example an IV bag. It will be understood that in various embodiments described herein, a different type of target container or destination container can be used instead of an IV bag (e.g., a syringe, a bottle, a vial, an elastomeric pump, etc.) even when not specifically mentioned.

In some embodiments, the system 1200 can include source adapters 1236*a-b* configured to receive the source containers 1220*a-b* and removably connect to the connectors 1226*a-b*. Thus, when a source container 1220*a-c* runs out of fluid, the empty source container 1220*a-b* and its corresponding adapter 1236*a-b* can be removed and replaced without requiring disengagement of the associated connector 1226*a-b* from the housing 1202. In some embodiments, source adapters 1236*a-b* can be omitted, and the source containers 1220*a-b* can be directly received by the connectors 1226*a-b*.

In some embodiments using two fluid or more transfer stations 1218*a-b*, the fluid transfer system 1200 can be used to transfer and combine individual fluids from the source containers 1220*a-b* to the target container 1224. The system 1200 can be used for compounding mixtures of fluids. For example, the system 1200 can be used to combine multiple medications together or to combine feeding fluids (e.g., water, dextrose, lipids, vitamins, minerals). The system 1200 can also be used to dilute a medication or other fluid to a desired concentration level. In some embodiments, a first fluid transfer station 1218*a* can include a concentrated medication or other fluid, and a second fluid transfer station 1218*b* can include saline or other diluent. The system 1200 can be configured to receive input (e.g., from a user or from a hospital information system) indicating a desired amount and concentration of medication, and the system 1200 can be configured to transfer the precise amounts of the concentrated medication and the diluent required to fill the source container 1224*a* with the desired amount and concentration of the medication. The system can calculate the amount that needs to be transferred from each fluid transfer station 1218. The operation can then be done serially by transferring a first fluid from the first transfer station 1218*a* and then separately transferring a second fluid from the second transfer station 1218*b*. In some embodiments, a technician can manually connect the first fluid transfer station 1218*a*, via connector 1230*a*, to the target container 1224. After the first fluid is transferred the connector 1230*a* is disconnected and second fluid transfer station is connected, via connector 1230*b*, to the target container 1224 to transfer the second fluid. In some embodiments, the system 1200 can include an actuator that is capable of automatically switching the connection of the target container 1224 between the fluid transfer stations 1218*a-b*. In some embodiments, the actuator can switch between different fluid sources at the same fluid transfer station. For example, the first fluid source can be a concentrated medication or other fluid, and a second fluid source can be saline or other diluent.

In some embodiments, the system 1200 can include compatibility modules 1232*a-b* for permitting connections with approved connectors 1226*a-b*, and for preventing connectors other than approved connectors 1226*a-b* from being placed in communication with the system 1200. The compatibility modules can be, for example, a specifically shaped mounting feature (e.g., on the housing of the fluid transfer station) that is configured to interface with a corresponding portion of the connector 1226*a-b*, 1230*a-b*. In some embodiments, the compatibility modules 1232*a-b* can be one or more sensors configured to detect the presence of an approved connector 1226*a-b* or to align with a specific portion of the connector 1226*a-b* during operation.

In some embodiments the system 1200 can include sensors 1234*a-b* for detecting the presence of the target container 1224. Sensors 1234*a-b* can be in communication with the controller 1204 so as to prevent the system 1200 from attempting to transfer fluid when no target container 1224 is connected. A variety of sensor types can be used for sensors 134*a-b*. For example, sensors 1234*a-b* can be weight sensors, sensor pads, infrared sensors, or other forms of electronic sensors. In some embodiments, the sensor 1234*a-b* can align with a substantially transparent portion of the connector 1226*a-b* to detect whether a valve on the connector 126*a-b* leading to target container 1224*a-b* is open. If open, the sensor 1234*a-b* can send a signal to the controller 1204 so that fluid transfer is permitted. The sensors 1234*a-b* can be configured to align properly with only approved connectors 1226*a-b* so that the sensors 1234*a-b* do not allow fluid transfer if an unapproved connector is used. Thus, the sensors 1234*a-b* can be used as the compatibility modules 1232*a-b* in some embodiments.

The fluid transfer system 1200 can have many different configurations. For example, in some embodiments there is only a single fluid transfer station. In some embodiments, certain features shown in FIG. 60 can be omitted for some or all of the transfer stations. For example, in some embodiments, a fluid transfer station can have the sensors omitted because, for example, a particular peristaltic pump does not generate sufficient pressure to cause fluid to leak out the connector when a target container is not connected and the pump is running.

Figure 61:
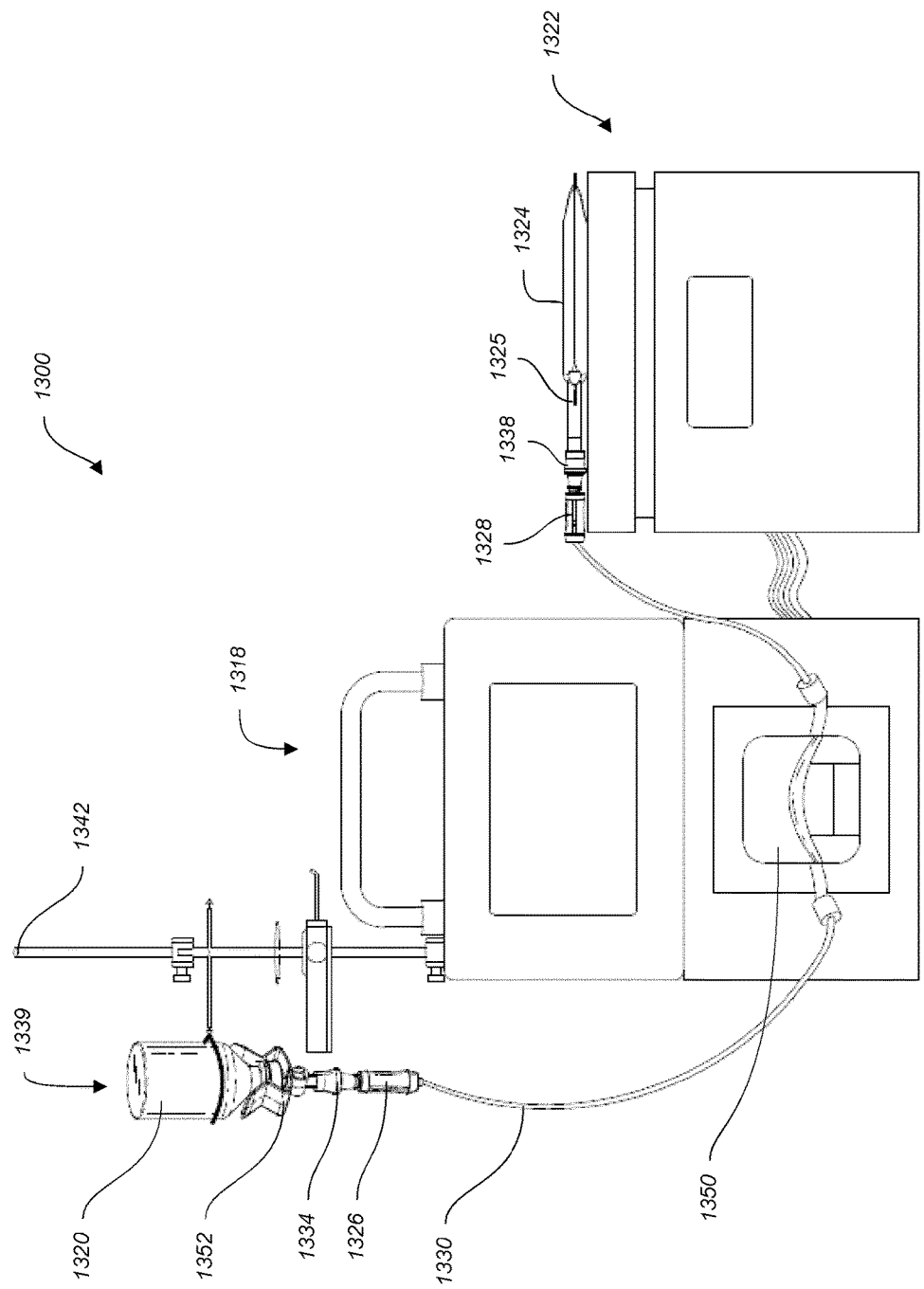
FIG. 61 is a view of an example embodiment of an automated system for transferring fluid.

FIG. 61 is an example embodiment of a fluid transfer system 1300, which can have features similar to, or the same as, the system 1200 described above or any other fluid transfer system described herein. FIG. 62 is a front view of the fluid transfer system 1300 and FIG. 63 is a back view of the fluid transfer system 1300. In FIGS. 62 and 63, certain features (i.e., the fluidics assembly) are omitted from view. The system 1300 can include a fluid transfer station 1318 and a weight sensor 1322.

The fluid transfer station 1318 includes a housing 1302, a peristaltic pump 1350, a motor (not shown), a user interface 1208, and a pole assembly 1342. The user interface 1208 can be incorporated into the housing. The user interface 1208 can include a touchscreen, a keypad, a display, or other suitable interface devices for providing information to a user and/or for providing input from the user to a controller (not shown).

As can be seen in FIG. 63, the fluid transfer station 1318 and the weight sensor 1322 can have communication interfaces 1310a-b. The communications interfaces 1310a-b can include one or more connection points to receive cables from one or more remote sources such as a remote terminal (e.g., a computer) or an automated management system (e.g., a hospital information system (HIS)). The fluid transfer station 1318 and the weight sensor 1322 have a communication link established between them, such as by cable 1312. In some embodiments the weight sensor 1322 and the fluid transfer station can establish a communication using wireless signal.

In some embodiments, the communication interfaces 1310a-b can be configured to provide a communication link between the system 1300 (i.e., the fluid transfer station and the weight sensor) and a remote location. The communication link can be provided by a wireless signal (e.g., using an antenna) or by one or more cables or a combination thereof. The communication link can make use of a network such as a WAN, a LAN, or the internet. In some embodiments, the communication interfaces 1310a-b can be configured to receive input (e.g., fluid transfer commands) from the remote location and/or can provide information (e.g., results or alerts) from the system to the remote location.

The fluid transfer station 1318 can be configured to transfer fluid from a vial 1320 to an IV bag 1324 using a peristaltic pump 1350. The fluid is transferred from the vial 1320 through a connector 1326, and into a hose assembly 1328. The peristaltic pump 1350 moves the fluid from the hose assembly 1330 through the connector 1328 and into the IV bag 1324. The operation of the peristaltic pump 1350 is controlled by the controller based on commands or information received from a user. An example of the fluidics assembly is described in additional detail below with additional reference to FIGS. 64 and 65. Operation of an embodiment of a peristaltic pump is described in additional detail below with reference to FIGS. 66 through 68.

The fluid transfer station 1328 can include a pole assembly 1342, which can be configured to hold fluid containers such as vials and fluid bags. A pole 1344 can extend upward from the housing 1302, and in some embodiments, the pole 1344 can be height adjustable and thumb screw 1346 can be tightened to hold the pole 1344 in place. The thumb screw 1346 can be loosened to enable adjustment of the height of the pole 1344, and in some embodiments, the pole 1344 can be lowered into a recess formed in the housing 1302 that is configured to receive the pole 1344. the pole 1344 can be entirely, substantially entirely, or mostly withdrawn into the housing 1302 when the pole 1344 is not in use (e.g., during storage or transportation or when not needed to support fluid containers). One or more support modules 1348 can be attached to the pole 1344 and can be configured to support fluid containers. The support modules 1348 can include thumb screws so that the positions of the support modules 1348 on the pole 1344 can be adjustable, and/or so that the support modules 1348 can be removable from the pole 1344. In the illustrated embodiment, the support module 1348 can have one or more curved arms for supporting a fluid container such as vial 1320.

In some embodiments, the weight sensor can include a housing 1316, a user interface, and a weighing surface 1321.

The user interface 1318 can be incorporated in the housing 1316. The user interface 1318 can provide a visual indication of weight, and other information. In some embodiments the weight sensor 1322 can receive commands or instructions through the user interface 1318 from a user. In some embodiments the weight sensor 1322 does not include a user interface 1318. The weighing surface 1321 is configured to provide a surface for the IV bag. The weighing surface 1321 can be sized so that the IV bag 1324 or other target container can be properly balanced and positioned on the weight sensor.

The weight sensor 1322 can provide information to (e.g., measurements, current state of operation, etc.) and receive commands (e.g., zeroing the weight sensor) from the fluid transfer station 1318 through the communication interface 1310b. The weight sensor 1322 is used to determine the amount of fluid transferred from the vial 1320 to the IV bag 1324.

Figure 65:
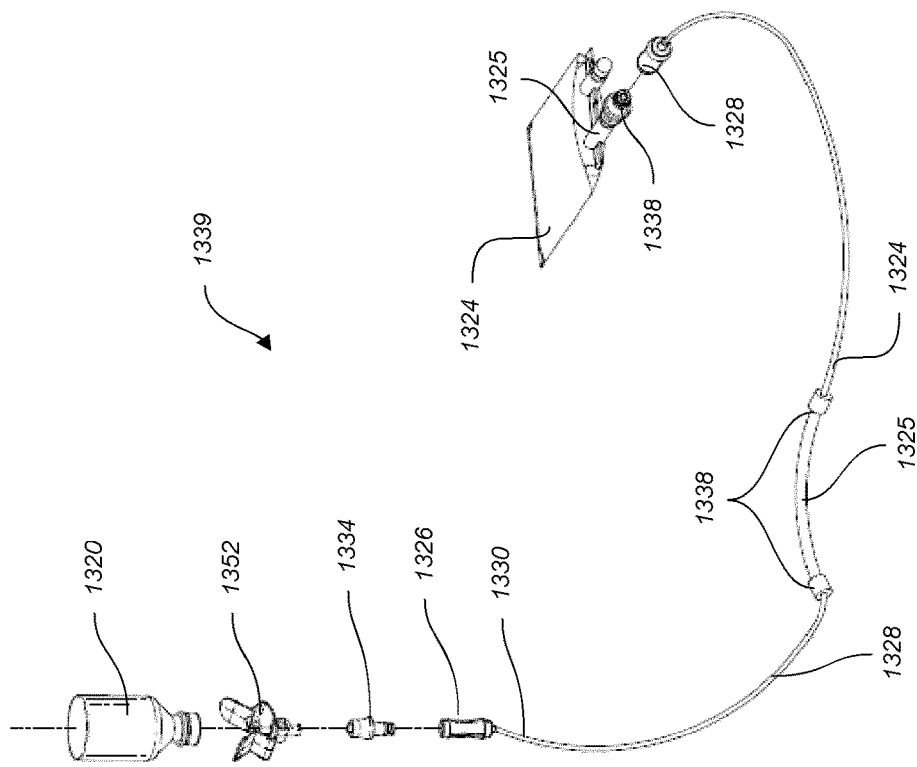
FIG. 65 is an exploded view of the fluidics assembly of FIG. 64.
Figure 64:
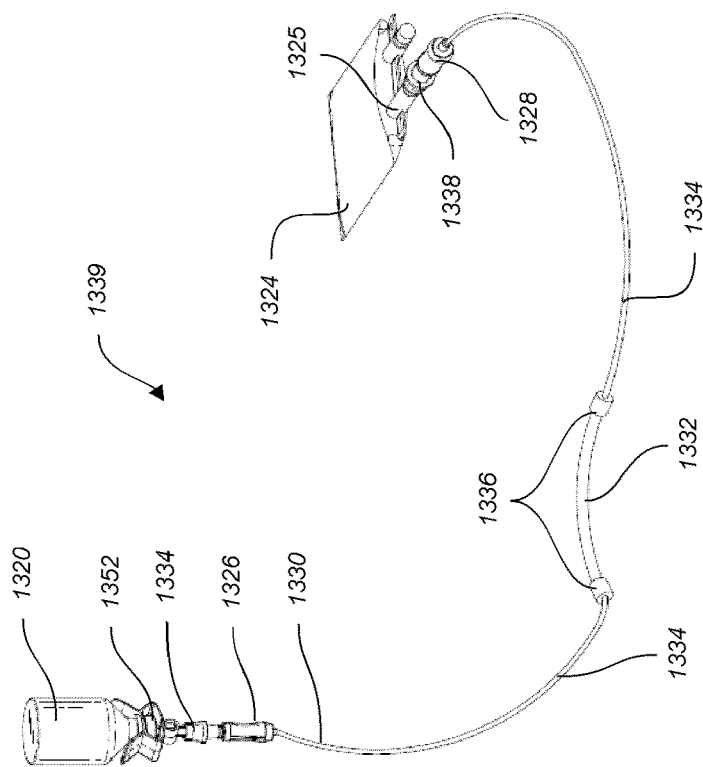
FIG. 64 is a perspective view of an example embodiment of a fluidics assembly that can be used to transfer fluid.

FIG. 64 is a perspective view of a fluidics assembly 1339 that can be used with the fluid transfer station 1318. FIG. 65 is a perspective exploded view of the fluidics assembly 1339 shown in FIG. 64. The fluid assembly 1339 can be used to transfer precise amounts of fluid from a vial 1320 to an IV bag 1324. The fluidics assembly 1339 includes a vial 1320, a vial adapter 1352 configured to provide fluid communication with the fluid (e.g., chemotherapy drug or other medication) contained within the vial 1320 to a connector 1326, a tubing assembly 1330, a connector 1328, and the IV bag assembly 1324. In some embodiments, the fluidics assembly 1339 can have features similar to, or the same as, those of the other fluidics systems disclosed herein. For example, the connector 1326 can be the same or substantially similar to the connector 1226a, also discussed herein. In some embodiments, the fluidics assembly 1339 can be configured to allow the vial 1320 and vial adapter 1352 to be replaced (e.g., when the vial runs out of fluid) without replacing the connector 1326 or the tubing assembly 1330. In some embodiments, the vial adapter 1352 can be configured to allow air to enter the vial 1320 via the vial adapter 1352, thereby substantially equalizing pressure in the vial 1320 as fluid is drawn out.

A tubing or hose assembly 1330 can extend between the connector 1326 and the connector 1328. The tubing assembly includes first tube portions 1334, a second tube portion 1332, and tubing connectors 1336. The second tube portion 1332 is configured to be inserted within the peristaltic pump 1350. In some embodiments the second portion 1332 can be configured to be more flexible than the first portion 1334. In some embodiments the second tube portion 1332 can be configured to have a lower durometer value than the first portions 1334. In some embodiments, the second portion 1332 can be more compressible than the first portion 1334 at a given force. In some embodiments, the tube 1332 can be formed from silicone rubber, or other appropriately formed elastomeric materials. The tube portions 1334 are positioned between the connectors 1326, 1328 and the tubing connectors 1336. In some embodiments the first tube portions 1334 can be smaller diameter tubing than is used for the second tube portion 1332. The tubing connectors 1336 are configured to create a fluid tight seal between the second tube portion 1332 and the first tube portions 1334. In some embodiments, there are no first tube portions 1334 or tubing connectors 1335 and the second tube portion 1332 is coupled to the connector 1326 and the connector 1328.

A connector 1326 (e.g., a Spiros® closeable male connector or a first Chemolock™ connector manufactured by ICU Medical, Inc., of San Clemente, Calif.) can be located at the end of the tubing assembly 1330 and can be used to connect to a corresponding connector 1334 (e.g., a Clave® connector or a second Chemolock™ connector manufactured by ICU Medical, Inc., of San Clemente, Calif.) that is attached to the fluid source container 1320. Additional details relating to Clave® connectors and some variations are disclosed in the '866 Patent. In various embodiments disclosed herein, other types of connectors can also be used, such as a MicroCLAVE® connector (manufactured by ICU Medical, Inc., of San Clemente, Calif.), or any other connector disclosed or described herein, including those in the '302 Application, including, for example, clear connectors. When the connectors 1326 and 1334 are engaged, a fluid connection exists between the fluid source container 1320 and the connector 1326. A tube 1330 can extend from an outlet of the connector 1326 to a connector 1328 (e.g., a Spiros® closable male connector) can be positioned at the opposite end of the tubing assembly 1330. A corresponding connector 1338 (e.g., a Clave® connector) can engage the connector 1328. The IV bag 1324 may have a supplemental line of tubing 1325 that can be configured to engage the connector 1338 to provide a fluid connection between the connector 1328 and the IV bag 1324.

Figure 67:
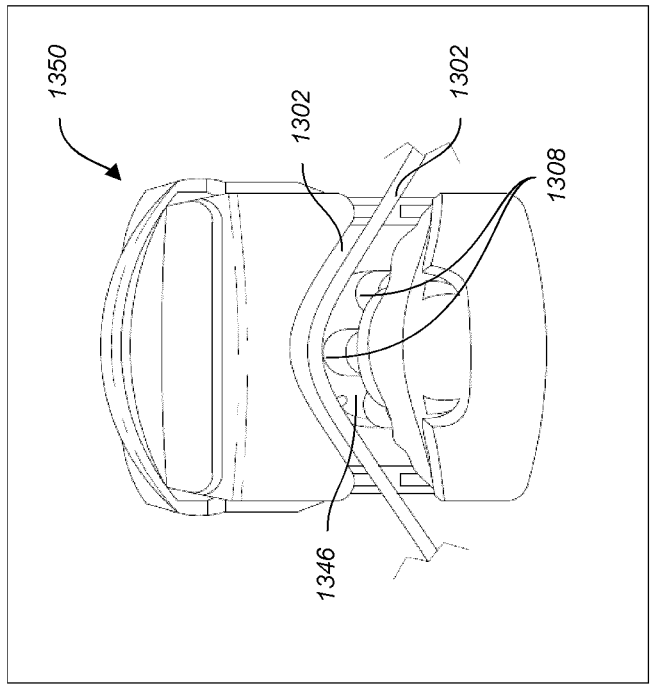
FIGS. 66 through 68 illustrate usage of an embodiment of a peristaltic pump.
Figure 66:
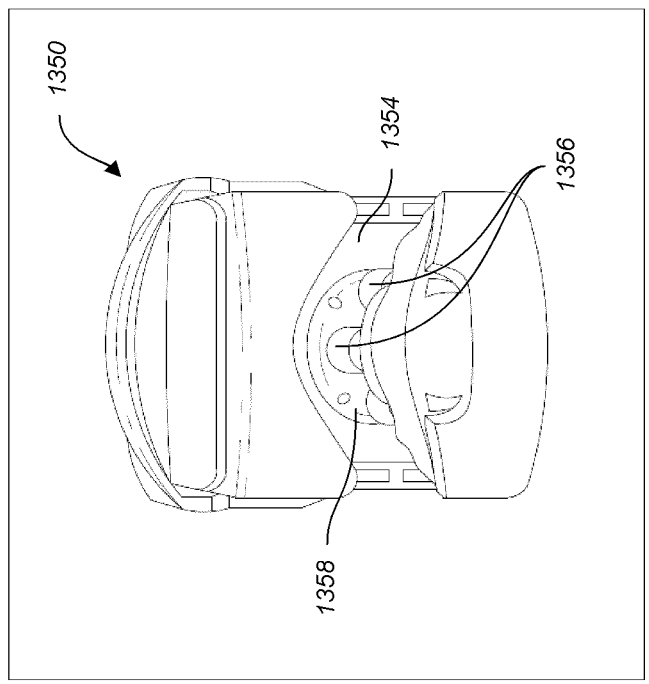
Figure 68:
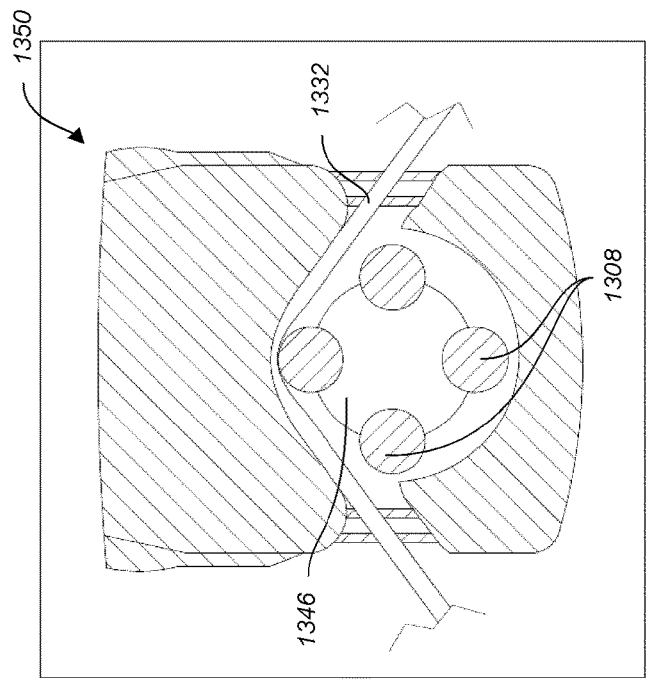

FIGS. 66 through 68 illustrate an embodiment of a peristaltic pump 1350 used by the fluid transfer station 1318. The peristaltic pump has a cover 1352, a mounting interface 1354, a plurality of lobes 1356, a rotor 1358, and a motor (not shown). The peristaltic pump is a positive displacement pump used for pumping fluid from the vial 1320 to the IV bag 1324. The fluid is transferred via a compressible tube 1332 fitted inside the mounting interface 1354. The rotor 1358 has a plurality of lobes 1356 attached to the external circumference of the rotor compresses the flexible tube. In some embodiments the lobes can be rollers, shoes, wipers, or other members that facilitate the operation of the pump. As the rotor turns, the part of tube under compression is compressed, or occludes, thus forcing the fluid to be pumped to move through the tube. As the tube 1332 opens to its natural state after the passing of the lobes 1356 fluid flow is induced.

In some embodiments of the pump 1350, as illustrated the cover 1352 is opened (see FIG. 66), the tube 1332 is positioned within the mounting interface 1354 (see FIG. 67), and the cover is closed. FIG. 68 illustrates the tubing 1332 mounted within the pump 1350 during operation. As shown the peristaltic pump lobes pinch the tube and compress the tubing, thereby moving fluid through the tube 1332.

The flow rate of the fluid through the pump 1350 can be controlled by the speed of the pump motor. The motor can be a variable speed motor and the fluid flow rate can be precisely controlled by varying the speed of the motor.

The peristaltic pump can operate at low pressures, and can avoid building up high pressures if the tubing is not connected to the IV bag. The pressures can be sufficiently low that the connector 1328 does not leak when it is closed and the pump is operating and connected to a fluid source, such as the vial 1320. In some embodiments, the system does not include sensors for detecting the presence of a target container.

Additionally, the system does not include sensors, in some embodiments, for detecting air bubbles because the system uses the weight of the target container to determine when the correct amount of fluid is transferred. The pump can continue to operate until the desired amount of fluid has been transferred to the target container.

Figure 69:
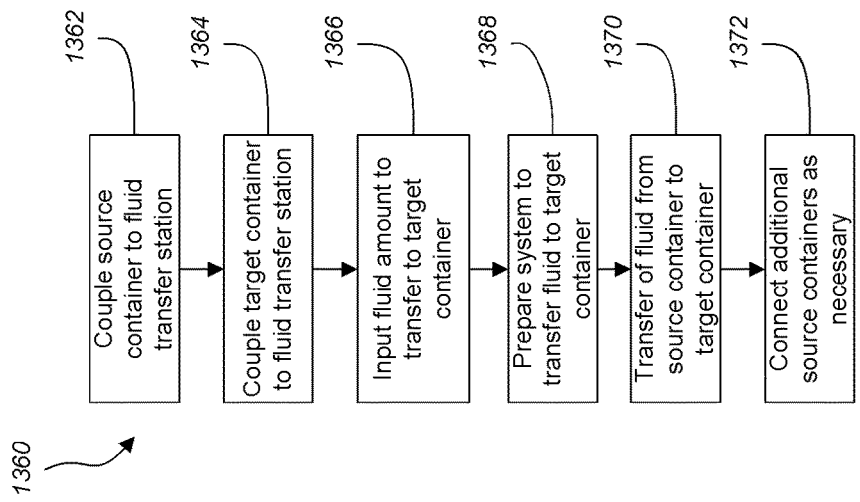
FIG. 69 is an example embodiment of a method for using an automated system for transferring fluid.

FIG. 69 is an example of a flowchart for a method of using a fluid transfer system to transfer fluid from a source container to a target container 1360. The fluid transfer system can use the same or similar components as the fluid transfer systems 1200 and 1300 described herein. At block 1362, source container (e.g., a medical vial or other suitable container such as a bag, a bottle, or a vat, etc.) is coupled to a fluid transfer station. The source container contains fluid (e.g., chemotherapy drug or other medical fluid). The source container can have a compatible adapter device. The source container is in fluid communication with a tubing assembly. The tubing assembly is in fluid communication with a target container (e.g., an IV bag, an elastomeric pump, a syringe, or other suitable container). The tubing assembly can be a closed system that retains substantially entirely, or entirely, all of the fluid within the assembly, permitting the fluid transfer to occur in a substantially entirely, or entirely, closed system. A closed system can reduce or eliminate the risk of injury, waste, or damage caused by liquid or vapor leakage when connecting and disconnecting the components of the fluidics system. The source container can be mounted on a fluid transfer station. The fluid transfer station can include a housing that incorporates a peristaltic pump, controller, user interface, and communication interface. The tubing assembly has a portion of tubing mounted within a peristaltic pump.

At block 1364 a target container (such as an IV bag, an elastomeric pump, a syringe, or other appropriate target container) is coupled to the opposite end of the tubing assembly. The target container is positioned on a weight sensor. The weight sensor is configured to weigh the target container to determine the amount of fluid that is transferred into the target container. The weight sensor can be incorporated in a separate housing from the fluid transfer station. The weight sensor can have a communication interface and can be in communication with the controller. The weight sensor can provide information to the controller and receive instructions from the controller.

At block 1366, the fluid transfer station receives a command to transfer a specific amount of fluid from the source container to the target container. A user can provide commands through the user interface on the fluid transfer station. In some embodiments the commands can be received by a remote source. The user can identify a specific amount of fluid that is to be transferred (e.g., 10 ml, 30, ml, 100 ml, etc.) to the target container. After determining the amount of fluid to be transferred, the user can instruct the fluid transfer system to proceed with the transfer. In some embodiments the fluid transfer system can verify that the user has entered in the correct amount of fluid to be transferred.

At block 1368, the fluid transfer station processes the commands and prepares the system to transfer the fluid to the target container. The controller zeros the weight sensor to compensate for other masses in the system, such as the weight of the target container assembly. This allows the scale to determine the amount of fluid that will be transferred to the target container. After the scale has been zeroed the controller can initiate the transfer of fluid to the target container.

At block 1370, the controller instructs the motor of the peristaltic pump to operate pumping until the weight of the scale meets the specified weight of transferred fluid in the target container. The motor can vary the speed of the peristaltic pump based on the amount of fluid to transfer to the target container. As the amount of fluid approaches the specified amount, the speed of the motor can slow down, thereby reducing the flow rate of fluid into the target container, in order to increase accuracy. The controller can use an algorithm to determine the appropriate speeds at which to operate the pump. In some embodiments the controller can determine the flow rate associated with different speeds of the motor. The controller will continue to operate the motor until the specified amount has been transferred to the target container.

At block 1372 additional source containers can be coupled to the fluid transfer station. The source containers can continue to be replaced until the specified amount of fluid has been transferred to the target container. In some embodiments the motor can stop when the controller detects that the source is disconnected. In other embodiments the pump continues to operate until the specified weight is achieved regardless of whether the source container is disconnected. In some embodiments the controller can determine that fluid is not being transferred from the source container to the target container. In some embodiments the controller can receive input from a sensor to determine whether the source container is empty. In some embodiments the controller can determine that fluid is not being transferred from the source container because the motor is operating but fluid is not being transferred. In such instances, the controller can provide an audible alarm to the user, stop the operation of the motor, and/or perform other appropriate actions. A reservoir container (as described in FIGS. 53 and 54) can be used to transfer the contents of multiple source containers to the reservoir container prior to transferring the fluid to the target container.

In some embodiments, the fluid transfer system can be configured to clear fluid out of the fluidics system, either automatically or upon instructions received from an operator (e.g., using a "clear" button). FIG. 70 is a flowchart showing an example method 1400 of a fluid clearing method. At block 1402, the system can transfer fluid. For example, the system can actuate a peristaltic pump to draw fluid out of a source container (e.g., vial) and to transfer the fluid into a target container (e.g., IV bag), as described herein. Once the specified amount of fluid has been transferred, the target container can be removed at block 1404. In some embodiments, another target container can be attached to the system and another fluid transfer procedure can be performed using the same type of fluid drawn from the same source container. In some embodiments, the source container can be removed at block 1406, for example, if no additional fluid transfers are to be performed or if the next fluid transfer is for a different type of fluid. In some embodiments, a volume of fluid remains in the connector after a fluid transfer. The fluid transfer system can flush the remaining fluid out of the connector so that the flushed fluid (which can be expensive) can be recovered for later use.

At block 1408, a new target container can be attached to receive the flushed fluid. For example, the vial (or other container) that was used as the source container for the fluid can be attached to the system as the target container so that the flushed fluid can be directed back into the container were it started. In some embodiments, the vial or associated vial adapter can be configured to regulate pressure in the vial as the flushed fluid is inserted therein, for example, by deflating a volume variable bag associated therewith, as described in the '157 Publication. In some embodiments, the vial and/or vial adapter does not have a variable volume component and the volume inserted into the vial can be small enough that the pressure in the vial is not raised beyond an acceptable threshold.

At block 1410, a new source attachment can be attached to the system. The source attachment can allow air to be drawn into the connector. For example, the new source attachment can be an empty vial and adapter similar to the vial 3907 and adapter 3908 of FIGS. 7 and 8. Air can enter through the filter 3948 and pass through the empty vial 3907, pass through the female connector 3944, and enter the connector to flush the fluid contained therein. In some embodiments, the source attachment does not include a vial or other container. For example, FIG. 46 shows an example embodiment of an air source attachment 770 that includes a connector 772 that is configured to engage the source connector portion of the connector being flushed. An air intake element 774 can be attached to the connector 772. The air intake element 774 can include a one-way air valve or filter 776 configured to allow air to enter the air intake element 774 and to prevent air from exiting through the filter 776. A pathway can lead from the filter 776 to the connector 772 to allow air to enter through the filter 776 and travel through the connector 772. In some embodiments, the air intake element can be integrally formed with the connector, for example, by placing the filter 776 at the male end of the connector 772 shown.

In some embodiments, the peristaltic pump does not produce enough pressure to flush the connectors and tubing assembly with the air intake valve 774 providing air at ambient pressure. The connector can be connected to a pressurized air source. The pressurized air source can provide sufficient pressure to flush the fluidics system.

In some embodiments, a fluid source container can be attached at block 1410, for example, to flush the fluid out of the connector using saline or water. However, in some embodiments, the fluid being flushed can become diluted or contaminated by the flushing fluid. It can be advantageous to use air in some embodiments. In some embodiments a flushing fluid can be used, such as a cleaning liquid, to flush the connector in order to clean the connector. In some embodiments, the connector can be cleaned for later use. In some embodiments, the connector can be disposable, and can be cleaned with a flushing fluid prior to being discarded, for example, if the transferred fluid is hazardous.

At block 1412, the system can flush fluid from the connector through a tubing assembly and into the target container (e.g., into the vial that had been used as the source container). For example, the peristaltic pump can draw air (or other flushing fluid) through the inlet of the connector and the peristaltic pump can then push the air out through the hosing assembly and the connector outlet towards the target container so that the air drives some or all the fluid into the target container (e.g., the vial that had been the source container). In some embodiments the peristaltic pump is connected to a pressurized air source to flush the connectors and tubing assembly. In some embodiments, the system can flush the connector at block 1412 in response to input received from a user or from an outside system, such as by pressing a user indicator, such as a "clear cassette" or "flush" button.

In some embodiments a workflow and/or data management system is used to monitor and track the preparation of medications using the fluid transfer systems. The workflow and/or data management system can provide a process for preparing and reporting medications. The workflow and/or data management system can provide a system that provides and stores processes, instructions, patient data, and monitoring procedures to help ensure that the correct medications, dosages, and diluents are used. This can increase patient safety, efficiency, and result in reduced drug waste and cost.

The workflow and/or data management system can be a distributed network-based system that provides remote access to the system. The system can provide a centralized processing system that maintains all of the information associated with the preparation of medications. Labs and workstations can communicate with the centralized system.

The workflow and/or data management system can include scanners, cameras, printers, and/or electronic storage systems for tracking and cataloguing the workflow process. The system can have a scanner for receiving information about fluid containers, medicaments, prescriptions, instructions, and or patients, such as by scanning bar codes, QR codes, or receiving data such as RFID data. Each medicine can have a code that is stored within the system that allows the system to keep track of them and verify that the proper medicine is being used in the process. The system can also utilize cameras to document one or more of the steps of the process. In some embodiments images can be captured of one or more medicines and components used in the process. In some embodiments, video can be used to record the portions of the preparation. In some embodiments a printer utilizing a real-time clock can be used to catalogue the timing of the workflow. The real-time clock can help ensure that the proper time is printed on each label.

FIG. 71 illustrates a method of using a workflow and/or data management system 1450. At block 1452 a dosage is selected for processing. The dosage can be provided to the user by a computer system that queues and stores the dosages that need to be prepared. In some embodiments the workflow and/or data management system can provide the dosages for processing based on one or more criteria. One criterion for processing dosages can be the need, urgency, or timing of the dosage for a patient. The workflow management system can also select dosages for processing based on efficiency. For example, the workflow system can group the processing of the same type of dosages. In some embodiments the user can select the dosage for processing from a list.

At block 1454, the selected dosage is prepared for processing. The workflow and/or data management system can provide instructions on preparation of the selected dosage. A dose label can be printed that will be placed on the completed dosage. The label can include information about the dosage, such as patient name, ingredients used in the application, and the time of processing. The label can also include a unique code, such as a bar code or QR code. The label can be placed onto the proper container and scanned by the workflow and/or data management system. In some embodiments the label for the completed dosage is prepared after the preparation is complete.

The workflow and/or data management system identifies each ingredient or component of the dosage. The workflow and/or data management system can also require that each component is scanned and photographed. This can help ensure that the correct ingredients with the correct concentrations are used for each medicine. If the incorrect component is scanned, the workflow and/or data management system can instruct the user to scan and use the correct component before proceeding.

At block 1456, the products used in the dosage can be compounded as necessary. The workflow and/or data management system can provide step by step instructions on compounding the dosages. The fluid transfer systems described herein can be used to compound the components. For example, the fluid from one or more source containers can be combined, or compounded, into a single target container.

In some embodiments the workflow and/or data management system can automate, control, and/or store information about the fluid transfer system. The user can couple the correct source and target containers to the fluid transfer system and instruct the workflow and/or data management system to proceed. In some embodiments the fluid transfer systems can have scanners that can be used to verify that the proper components are coupled to the system. The workflow and/or data management system can provide instructions to the fluid transfer systems to transfer the specified amount of fluid from the source container to the target containers. This process can help reduce error associated with the user entering the incorrect information into the fluid transfer system.

At block 1458, the dosage is verified. After the compounding procedures are complete, the dosage is removed from the fluid transfer system and verified by the workflow and/or data management system. The workflow and/or data management system can take a picture of the container and pictures of each of the components used to formulate the dosage and store one or more pictures of the process in a database. These pictures can be available for later retrieval by a user, and can be used to help verify that the proper amounts were transferred from each component. The workflow system can also scan labels on each component and the on the completed dosage. In some embodiments a label is printed after the process is complete and placed on the prepared medicine. In some embodiments, after all the information has been catalogued and processed, a user, such as a pharmacist, can access the information from a remote location. The user can review and either approve or reject the prepared medicine. Information regarding the timing, drug type, dosage, technician, patient identity, and/or patient diagnosis, or other stored information can be later retrieved from a database.

Embodiments have been described in connection with the accompanying drawings. However, it should be understood that the foregoing embodiments have been described at a level of detail to allow one of ordinary skill in the art to make and use the devices, systems, etc. described herein. A wide variety of variation is possible. Components, elements, and/or steps may be altered, added, removed, or rearranged. Additionally, processing steps may be added, removed, or reordered. While certain embodiments have been explicitly described, other embodiments will also be apparent to those of ordinary skill in the art based on this disclosure.

Some aspects of the systems and methods described herein can advantageously be implemented using, for example, computer software, hardware, firmware, or any combination of software, hardware, and firmware. Software can comprise computer executable code for performing the functions described herein. In some embodiments, computer-executable code is executed by one or more general purpose computers. However, a skilled artisan will appreciate, in light of this disclosure, that any module that can be implemented using software to be executed on a general purpose computer can also be implemented using a different combination of hardware, software, or firmware. For example, such a module can be implemented completely in hardware using a combination of integrated circuits. Alternatively or additionally, such a module can be implemented completely or partially using specialized computers designed to perform the particular functions described herein rather than by general purpose computers.

While certain embodiments have been explicitly described, other embodiments will become apparent to those of ordinary skill in the art based on this disclosure. Therefore, the scope of the invention is intended to be defined by reference to the claims as ultimately published in one or more publications or issued in one or more patents and not simply with regard to the explicitly described embodiments.

What is claimed is:

1. A fluid transfer module for use with an electronically controlled fluid dispensing system for the transfer of medical fluids between or among different medical fluid containers, the fluid transfer module comprising:
    a three-way connector comprising:
        a first interface configured to be connected in fluid communication with a fluid source container,
        a second interface configured to be connected in fluid communication with a fluid target container, and
        an intermediate interface configured to be in fluid communication with a syringe pump that is configured to transfer fluid through the three-way connector; and
    a fluid switch having a first configuration configured to open a first fluid pathway between the fluid source container and the intermediate interface, the fluid switch having a second configuration configured to close the first fluid pathway between the fluid source container and the intermediate interface and to open a second fluid pathway between the intermediate interface and the second interface, wherein the fluid switch is configured to interact with an actuator of the electronically controlled fluid dispensing system that is configured to move the fluid switch between the first configuration and the second configuration,
    wherein the fluid transfer module is configured to be removeably attachable by a user to the electronically controlled fluid dispensing system such that, when the fluid transfer module is connected to the electronically controlled fluid dispensing system, a camera on the electronically controlled fluid dispensing system can capture an image of at least a portion of the fluid transfer module, and
    wherein the fluid transfer module is configured to substantially prevent fluid within the fluid transfer module from escaping upon disconnection of the fluid transfer module from the fluid source container and the fluid target container.

2. A combination of the fluid transfer module of claim 1 with the electronically controlled fluid dispensing system.

3. A combination of the fluid transfer module of claim 1 with the syringe pump.

4. A combination of the fluid transfer module of claim 1 with the fluid target container.

5. The fluid transfer module of claim 1, wherein the fluid switch comprises a stopcock.

6. The fluid transfer module of claim 1, wherein the first interface comprises a first closable connector configured to removably couple to the fluid source container, and wherein the second interface comprises a second closable connector configured to removably couple to the fluid target container.

7. The fluid transfer module of claim 6, wherein the first closable connector is a closable male connector and the second closable connector is a closable male connector.

8. The fluid transfer module of claim 1, wherein the intermediate interface comprises a syringe interface configured to be connected to an intermediate container.

9. The fluid transfer module of claim 1, wherein the fluid transfer module further comprises a sensor region positioned between the fluid switch and the intermediate interface such that the sensor region is configured to permit a bubble sensor of the electronically controlled fluid dispensing system to detect air in the fluid passageway of the fluid transfer module.

10. The fluid transfer module of claim 1, wherein the fluid transfer module is configured to interact with a destination sensor of the electronically controlled fluid dispensing system, and wherein the destination sensor is configured to detect whether or not the fluid target container is connected to the second interface and to output information indicating whether or not the target container is connected.

11. The fluid transfer module of claim 10, wherein the destination sensor is configured to detect whether the second interface is open.

12. The fluid transfer module of claim 1, wherein the control system is configured to receive instructions from a remote source.

13. A fluid transfer system comprising:
    an electronically controlled fluid dispensing system; and
    the fluid transfer module of claim 1 removably attached to the electronically controlled fluid dispensing system.

14. The fluid transfer system of claim 13, wherein the electronically controlled fluid dispensing system comprises a beam emitter and a beam detector, and wherein the electronically controlled fluid dispensing system is capable of detecting air bubbles in the fluid transfer module.

15. The fluid transfer system of claim 13, wherein the electronically controlled fluid dispensing system comprises a bubble sensor configured to align with a sensor region of the fluid transfer module for detecting air in the fluid passageway of the fluid transfer module.

16. The fluid transfer system of claim 13, wherein the electronically controlled fluid dispensing system comprises:
    one or more sensors configured to detect whether or not the three-way connector is attached to the electronically controlled fluid dispensing system, wherein the control system is configured to not allow fluid transfer when the three-way connector is not detected; and
    a mounting module configured to align the three-way connector with the one or more sensors.

17. The fluid transfer system of claim 13, wherein the electronically controlled fluid dispensing system comprises one or more cameras configured to capture images of at least a portion of the fluid transfer module to document one or more steps of a fluid transfer process performed by the electronically controlled fluid dispensing system.

18. A method of enabling the transfer of fluid using a medical fluid transfer system, the method comprising:
    providing a fluid transfer module comprising:
        a three-way connector comprising:
            a first interface configured to be connected in fluid communication with a fluid source container,
            a second interface configured to be connected in fluid communication with a fluid target container, and
            an intermediate interface configured to be in fluid communication with a syringe pump that is configured to transfer fluid through the three-way connector; and
        a fluid switch having a first configuration configured to open a first fluid pathway between the fluid source container and the intermediate interface, the fluid switch having a second configuration configured to close the first fluid pathway between the fluid source container and the intermediate interface and to open a second fluid pathway between the intermediate interface and the second interface, wherein the fluid switch is configured to interact with an actuator of the medical fluid transfer system that is configured to move the fluid switch between the first configuration and the second configuration, wherein the fluid transfer module is configured to be removeably attachable by a user to the medical fluid transfer system such that, when the fluid transfer module is connected to the medical fluid transfer system, a camera on the medical fluid transfer system can capture an image of at least a portion of the fluid transfer module, and wherein the fluid transfer module is configured to substantially prevent fluid within the fluid transfer module from escaping upon disconnection of the fluid transfer module from the fluid source container and the fluid target container.

19. The method of claim 18, wherein the fluid switch comprises a stopcock.

20. The method of claim 18, wherein the first interface comprises a first closable connector configured to removably couple to the fluid source container, and wherein the second interface comprises a second closable connector configured to removably couple to the fluid target container.

21. The method of claim 18, wherein the intermediate interface comprises a syringe interface configured to be connected to an intermediate container.

22. The method of claim 18, wherein the fluid transfer module further comprises a sensor region positioned between the fluid switch and the intermediate interface such that the sensor region is configured to permit a bubble sensor of the electronically controlled fluid dispensing system to detect air in the fluid passageway of the fluid transfer module.

23. The method of claim 18 further comprising providing a medical fluid transfer system.

\* \* \* \* \*